(12) United States Patent
Haddach et al.

(10) Patent No.: US 6,514,982 B1
(45) Date of Patent: Feb. 4, 2003

(54) CRF RECEPTOR ANTAGONISTS AND METHODS RELATING THERETO

(75) Inventors: Mustapha Haddach, San Diego, CA (US); Brian P. Dyck, San Diego, CA (US); Charles Q. Huang, San Diego, CA (US); Jodie Nelson, San Diego, CA (US); Zhiqiang Guo, San Diego, CA (US); James R. McCarthy, Zionsville, IN (US)

(73) Assignee: Neurocrine Biosciences, Inc., San Diego, CA (US)

(*) Notice: Subject to any disclaimer, the term of this patent is extended or adjusted under 35 U.S.C. 154(b) by 0 days.

(21) Appl. No.: 09/439,840

(22) Filed: Nov. 12, 1999

Related U.S. Application Data

(63) Continuation-in-part of application No. 09/401,364, filed on Sep. 21, 1999, now abandoned, which is a continuation-in-part of application No. 09/370,837, filed on Aug. 9, 1999, now abandoned, which is a continuation-in-part of application No. 09/191,073, filed on Nov. 12, 1998, now abandoned.

(51) Int. Cl.$^7$ .................. C07D 487/04; A61K 31/517; A61K 31/519; A61K 31/706; A61K 31/7064

(52) U.S. Cl. .................. 514/267; 514/232.8; 514/241; 514/252.02; 514/259; 514/252.04; 514/292; 514/252.16; 514/256; 514/253.03; 514/248; 544/180; 544/115; 544/238; 544/250; 544/251; 544/284; 544/237; 544/333; 544/405; 544/235

(58) Field of Search .................. 546/82; 544/251, 544/180, 250, 237, 235; 514/293, 268, 267, 232.8, 252.04, 292, 253.03

(56) References Cited

U.S. PATENT DOCUMENTS

| | | | |
|---|---|---|---|
| 4,605,642 A | 8/1986 | Rivier et al. | 514/12 |
| 4,904,658 A | 2/1990 | Tseng et al. | 514/233.2 |
| 5,063,245 A | 11/1991 | Abreu et al. | 514/404 |
| 5,464,847 A | 11/1995 | Courtemanche et al. | 514/342 |
| 5,880,135 A | 3/1999 | Gully et al. | 514/307 |

FOREIGN PATENT DOCUMENTS

| | | |
|---|---|---|
| WO | WO 94/13643 | 6/1994 |
| WO | WO 94/13644 | 6/1994 |
| WO | WO 94/13661 | 6/1994 |
| WO | WO 94/13676 | 6/1994 |
| WO | WO 94/13677 | 6/1994 |
| WO | WO 95/10506 | 4/1995 |
| WO | WO 95/33750 | 12/1995 |
| WO | WO 95/34563 | 12/1995 |
| WO | WO 96/35689 | 11/1996 |
| WO | WO 97/00868 | 1/1997 |
| WO | WO 97/35539 | 10/1997 |
| WO | WO 97/35580 | 10/1997 |
| WO | WO 97/35846 | 10/1997 |
| WO | WO 97/44038 | 11/1997 |
| WO | WO 98/03510 | 1/1998 |
| WO | WO 98/05661 | 2/1998 |
| WO | WO 98/08846 | 3/1998 |
| WO | WO 98/08847 | 3/1998 |
| WO | WO 98/11075 | 3/1998 |
| WO | WO 98/15543 | 4/1998 |
| WO | WO 98/21200 | 5/1998 |
| WO | WO 98/29413 | 7/1998 |
| WO | WO 99/40091 | 8/1999 |
| WO | WO-00/27846 | * 5/2000 |

OTHER PUBLICATIONS

Boyer Acta Psychiatr. Scand. Suppl. 406 (2000) 24—29 (Medline abstract only).*
Smagin et al Eur. J. of Pharm. 405 (2000) 199—206.*
Gilligan et al Ann. Rep. Med. Chem. 32 (1997) 41—50.*
Wong et al Proc. Nat. Acad. Sci. 97 (2000) 325—330.*
Zobel et al J. Psychiatr. Res. 34 (2000) 171—181 (Medline abstract only).*
Rivier et al., "Synthetic Competitive Antagonists of Corticotropin–Releasing Factor: Effect on ACTH Secretion in the Rat," Science 224: 889–891, 1984.

* cited by examiner

Primary Examiner—John M. Ford
(74) Attorney, Agent, or Firm—Sed IP Law Group PLLC

(57) ABSTRACT

CRF receptor antagonists are disclosed which have utility in the treatment of a variety of disorders, including the treatment of disorders manifesting hypersecretion of CRF in a warm-blooded animals, such as stroke. The CRF receptor antagonists of this invention have the following structure:

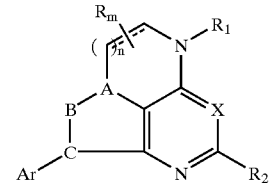

including stereoisomers and pharmaceutically acceptable salts thereof, wherein n, m, A, B, C, R, $R_1$, $R_2$ and Ar are as defined herein. Compositions containing a CRF receptor antagonist in combination with a pharmaceutically acceptable carrier are also disclosed, as well as methods for use of the same

32 Claims, No Drawings

* # CRF RECEPTOR ANTAGONISTS AND METHODS RELATING THERETO

CROSS REFERENCE TO RELATED APPLICATIONS

This application is a continuation-in-part of U.S. application No. 09/401,364, filed Sep. 21, 1999; now abandoned, which is a continuation-in-part of U.S. application Ser. No. 09/370,837, filed Aug. 9, 1999; now abandoned, which is a continuation-in-part of U.S. application Ser. No. 09/191,073, filed Nov. 12, 1998, now abandoned, (which applications are hereby incorporated by reference in their entirety).

TECHNICAL FIELD

This invention relates generally to CRF receptor antagonists, and to methods of treating disorders by administration of such antagonists to a warm-blooded animal in need thereof.

BACKGROUND OF THE INVENTION

The first corticotropin-releasing factor (CRF) was isolated from ovine hypothalmi and identified as a 41-amino acid peptide (Vale et al., *Science* 213:1394–1397, 1981). Subsequently, sequences of human and rat CRF were isolated and determined to be identical, but different from ovine CRF in 7 of the 41 amino acid residues (Rivier et al., *Proc. Natl. Acad Sci. USA* 80:4851, 1983; Shibahara et al., *EMBO J.* 2:775, 1983).

CRF has been found to produce profound alterations in endocrine, nervous and immune system function. CRF is believed to be the major physiological regulator of the basal and stress-release of adrenocorticotropic hormone ("ACTH"), β-endorphin, and other pro-opiomelanocortin ("POMC")-derived peptides from the anterior pituitary (Vale et al., *Science* 213:1394–1397, 1981). Briefly, CRF is believed to initiate its biological effects by binding to a plasma membrane receptor which has been found to be distributed throughout the brain (DeSouza et al., *Science* 224:1449–1451, 1984), pituitary (DeSouza et al., *Methods Enzymol.* 124:560, 1986; Wynn et al., *Biochem. Biophys. Res. Comm.* 110:602–608, 1983), adrenals (Udelsman et al., *Nature* 319:147–150, 1986) and spleen (Webster, E. L., and E. B. DeSouza, *Endocrinology* 122:609–617, 1988). The CRF receptor is coupled to a GTP-binding protein (Perrin et al., *Endocrinology* 118:1171–1179, 1986) which mediates CRF-stimulated increase in intracellular production of cAMP (Bilezikjian, L. M., and W. W. Vale, *Endocrinology* 113:657–662, 1983). The receptor for CRF has now been cloned from rat (Perrin et al., *Endo* 133(6):3058–3061, 1993), and human brain (Chen et al., *PNAS* 90(19):8967–8971, 1993; Vita et al., *FEBS* 335(1):1–5, 1993). This receptor is a 415 amino acid protein comprising seven membrane spanning domains. A comparison of identity between rat and human sequences shows a high degree of homology (97%) at the amino acid level.

In addition to its role in stimulating the production of ACTH and POMC, CRF is also believed to coordinate many of the endocrine, autonomic, and behavioral responses to stress, and may be involved in the pathophysiology of affective disorders. Moreover, CRF is believed to be a key intermediary in communication between the immune, central nervous, endocrine and cardiovascular systems (Crofford et al., *J. Clin. Invest.* 90:2555–2564, 1992; Sapolsky et al., *Science* 238:522–524, 1987; Tilders et al., *Regul. Peptides* 5:77–84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. For example, intracerebroventricular injection of CRF results in behavioral activation (Sutton et al., *Nature* 297:331, 1982), persistent activation of the electroencephalogram (Ehlers et al., *Brain Res.* 278:332, 1983), stimulation of the sympathoadrenomedullary pathway (Brown et al., *Endocrinology* 110:928, 1982), an increase of heart rate and blood pressure (Fisher et al., *Endocrinology* 110:2222, 1982), an increase in oxygen consumption (Brown et al., *Life Sciences* 30:207, 1982), alteration of gastrointestinal activity (Williams et al., *Am. J Physiol.* 253:G582, 1987), suppression of food consumption (Levine et al., *Neuropharmacology* 22:337, 1983), modification of sexual behavior (Sirinathsinghji et al., *Nature* 305:232, 1983), and immune function compromise (Irwin et al., *Am. J Physiol.* 255:R744, 1988). Furthermore, clinical data suggests that CRF may be hypersecreted in the brain in depression, anxiety-related disorders, and anorexia nervosa. (DeSouza, *Ann. Reports in Med. Chem.* 25:215–223, 1990). Accordingly, clinical data suggests that CRF receptor antagonists may represent novel antidepressant and/or anxiolytic drugs that may be useful in the treatment of the neuropsychiatric disorders manifesting hypersecretion of CRF.

The first CRF receptor antagonists were peptides (see, e.g., Rivier et al., U.S. Pat. No. 4,605,642; Rivier et al., *Science* 224:889, 1984). While these peptides established that CRF receptor antagonists can attenuate the pharmacological responses to CRF, peptide CRF receptor antagonists suffer from the usual drawbacks of peptide therapeutics including lack of stability and limited oral activity. More recently, small molecule CRF receptor antagonists have been reported. For example, substituted 4-thio-5-oxo-3-pyyrazoline derivatives (Abreu et al., U.S. Pat. No. 5,063,245) and substituted 2-aminothiazole derivatives (Courternanche et al., Australian Patent No. AU-A-41399/93) have been reported as CRF receptor antagonists. These particular derivatives were found to be effective in inhibiting the binding of CRF to.its receptor in the 1–10 μM range and 0.1–10 μM range, respectively.

More recently, numerous small molecule CRR receptor antagonists have been proposed, including the compounds disclosed in the following patent documents: WO 94/13643, WO 94/13644, WO 94/13661, WO 94/13676, WO 94/13677, WO 95/10506, WO 95/33750, WO 96/35689, WO 97/00868, WO 97,35539, WO 97/35580, WO 97,35846, WO 97/44038, WO 98/03510, WO 98/05661, WO 98/08846, WO 98/08847, WO 98/11075, WO 98/15543, WO 98/21200 and WO 98/29413.

Due to the physiological significance of CRF, the development of biologically-active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

SUMMARY OF THE INVENTION

In brief, this invention is generally directed to CRF receptor antagonists, and more specifically to CRF receptor antagonists having the following general structure (I):

(I)

including stereoisomers, prodrugs and pharmaceutically acceptable salts thereof, wherein n, m, A, B, C, X, R, $R_1$, $R_2$, and Ar are as defined below.

The CRF receptor antagonists of this invention have utility over a wide range of therapeutic applications, and may be used to treat a variety of disorders or illnesses, including stress-related disorders. Such methods include administering an effective amount of a CRF receptor antagonist of this invention, preferably in the form of a pharmaceutical composition, to an animal in need thereof. Accordingly, in another embodiment, pharmaceutical compositions are disclosed containing one or more CRF receptor antagonists of this invention in combination with a pharmaceutically acceptable carrier and/or diluent.

These and other aspects of the invention will be apparent upon reference to the following detailed description. To this end, various references are set forth herein which describe in more detail certain procedures, compounds and/or compositions, and are hereby incorporated by reference in their entirety.

DETAILED DESCRIPTION OF THE INVENTION

The present invention is directed generally to compounds useful as corticotropin-releasing factor (CRF) receptor antagonists.

In a first embodiment, the CRF receptor antagonists of this invention have the following structure (I):

(I)

including stereoisomers, prodrugs and pharmaceutically acceptable salts thereof, wherein:

n is 1 or 2;

A and C are each independently nitrogen, carbon or CH;

B is nitrogen or $CR_3$;

with the provisos that at least one of A, B and C is nitrogen; A, B and C are not all nitrogen; and either A—B or B—C is a double bond;

X is nitrogen or CH;

Ar is aryl, substituted aryl, heteroaryl, or substituted heteroaryl;

R is an optional substituent which, at each occurrence, is independently alkyl, alkylidenyl, arylalkyl or heteroarylalkyl, wherein m is 0, 1, 2 or 3 and represents the number of R substituents;

$R_1$ is —C(H)$_{0,1}$($R_4$)($R_5$) or —SO$_2R_5$;

$R_2$ is hydrogen or alkyl;

$R_3$ is hydrogen, alkyl or haloalkyl;

$R_4$ is hydrogen, keto, alkyl, alkylidenyl, or halo; and $R_5$ is a radical of the formula —Y—Z—$R_6$, wherein
  Y is an alkanediyl, substituted alkanediyl, or a direct bond,
  Z is NH, —N($R_7$), O, S, SO$_2$, C(=O), C(=O)O, OC(=O), NHC(=O), C(=O)NH, NH(SO$_2$), (SO$_2$)NH, $NR_8$C(=O)O, or a direct bond;
  $R_6$ is hydrogen, alkyl, substituted alkyl, aryl, substituted aryl, arylalkyl, substituted arylalkyl, heterocyle, substituted heterocycle, heterocyclealkyl, or substituted heterocylcealkyl; or
  $R_7$ and $R_8$ are the same or different and independently alkyl, substituted alkyl, aryl, substituted aryl, arylalkyl, substituted arylalkyl, heterocyle, substituted heterocycle, heterocyclealkyl, or substituted heterocylcealkyl; or
  $R_6$ and $R_7$ taken together with the nitrogen atom to which they are attached form a heterocyle ring or substituted heterocyle ring;

or $R_4$ and $R_5$ taken together form cycloalkyl, substituted cycloalkyl, cycloalkylcycloalkyl, substituted cycloalkylcycloalkyl, cycloalkylaryl, substituted cycloalkyaryl, cycloalkylheterocycle, or substituted cycloalkylheterocycle.

As used herein, the above terms have the following meaning:

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —CH$_2$cyclopropyl, —CH$_2$cyclobutyl, —CH$_2$cyclopentyl, —CH$_2$cyclohexyl, and the like; while unsaturated cyclic alkyls include cyclopentenyl and cyclohexenyl, and the like. Cyclic alkyls, also referred to as "homocyclic rings," and include di- and poly-homocyclic rings such as decalin and adamantyl, Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

"Alkylidenyl" represents a divalent alkyl from which two hydrogen atoms are taken from the same carbon atom, such as =CH$_2$, =CHCH$_3$, =CHCH$_2$CH$_3$, =C(CH$_3$)CH$^2$CH$_3$, and the like.

"Alkanediyl" means a divalent alkyl from which two hydrogen atoms are taken from the same carbon atom or from different carbon atoms, such as —CH$_2$—CH$_2$CH$_2$—, —CH$_2$CH$_2$CH$_2$—, —CH(CH$_3$)CH$_2$—, and the like.

"Aryl" means an aromatic carbocyclic moiety such as phenyl or naphthyl.

"Arylalkyl" means an alkyl having at least one alkyl hydrogen atoms replaced with an aryl moiety, such as benzyl, —CH$_2$-(1 or 2-naphthyl), —(CH$_2$)$_2$phenyl, —(CH$_2$)$_3$phenyl, —CH(phenyl)$_2$, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems.

Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —CH$_2$pyridinyl, —CH$_2$pyrimidinyl, and the like.

"Heterocycle" (also referred to herein as a "heterocycle ring") means a 5- to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydrothienyl, tetrahydropyrimidinyl, tetrahydrothiopyranyl, and the like.

"Heterocyclealkyl" means an alkyl having at least one alkyl hydrogen atom replaced with a heterocycle, such as —CH$_2$morpholinyl, and the like.

"Cycloalkyl" means a saturated or unsaturated (but not aromatic) carbocyclic ring containing from 3–8 carbon atoms, such as cyclopentane, cyclohexane, cycloheptane, cyclohexene, and the like.

"Cycloalkylcycloalkyl" means a cycloalkyl ring fused to a cycloalkyl ring, such as decalin.

"Cycloalkylaryl" means a cycloalkyl ring fused to aryl, such as tetralin.

"Cycloalkylheterocycle" means a cycloalkyl ring fused to a heterocycle ring.

The term "substituted" as used herein means any of the above groups (e.g., alkyl, aryl, arylalkyl, heteroaryl, heteroarylalkyl, heterocycle, heterocyclealkyl, etc.) wherein at least one hydrogen atom is replaced with a substituent. In the case of a keto substituent ("—C(=O)—") two hydrogen atoms are replaced. When substituted, "substituents" within the context of this invention include halogen, hydroxy, cyano, nitro, amino, alkylamino, dialkylamino, alkyl, alkoxy, alkylthio, haloalkyl, aryl, substituted aryl, arylalkyl, substituted arylalkyl, heteroaryl, substituted heteroaryl, heteroarylalkyl, substituted heteroarylalkyl, heterocycle, substitued heterocycle, heterocyclealkyl, substituted heterocyclealkyl, —NR$_a$R$_b$, —NR$_a$C(=O)R$_b$, —NR$_a$C(=O)NR$_a$NR$_b$, —NR$_a$C(=O)OR$_b$, —NR$_a$SO$_2$R$_b$, —OR$_a$, —C(=O)R$_a$, —C(=O)OR$_a$, —C(=O)NR$_a$R$_b$, —OC(=O)NR$_a$R$_b$, —SH, —SR$_a$, —SOR$_a$, —S(=O)$_2$R$_a$, —OS(=O)$_2$R$_a$, —S(=O)$_2$OR$_a$, wherein R$_a$ and R$_b$ are the same or different and independently hydrogen, alkyl, haloalkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocylealkyl or substituted heterocyclealkyl.

"Halogen" means fluoro, chloro, bromo and iodo.

"Haloalkyl" means an alkyl having at least one hydrogen atom replaced with halogen, such as trifluoromethyl and the like.

"Alkoxy" means an alkyl moiety attached through an oxygen bridge (i.e., —O-alkyl) such as methoxy, ethoxy, and the like.

"Alkylthio" means an alkyl moiety attached through a sulfur bridge (i.e., —S-alkyl) such as methylthio, ethylthio, and the like.

"Alkylsulfonyl" means an alkyl moiety attached through a sulfonyl bridge (i.e., —SO$_2$-alkyl) such as methylsulfonyl, ethylsulfonyl, and the like.

"Alkylamino" and "dialkylamino" mean one or two alkyl moiety attached through a nitrogen bridge (i.e.,—N-alkyl) such as methylamino, ethylamino, dimethylamino, diethylamino, and the like.

"Hydroxyalkyl" means an alkyl substituted with at least one hydroxyl group.

"Mono- or di(cycloalkyl)methyl" represents a methyl group substituted with one or two cycloalkyl groups, such as cyclopropylmethyl, dicyclopropylmethyl, and the like.

"Alkylcarbonylalkyl" represents an alkyl substitutedwith a —C(=O)alkyl group.

"Alkylcarbonyloxyalkyl" represents an alkyl substituted with a —C(=O)Oalkyl group or a —OC(=O)alkyl group.

"Alkyloxyalkyl" represents an alkyl substituted with a —O-alkyl group.

"Alkylthioalkyl" represents a alkyl substituted with a —S-alkyl group.

"Mono- or di(alkyl)amino represents an amino substituted with one alkyl or with two alkyls, respectively.

"Mono- or di(alkyl)aminoalkyl" represents a alkyl substituted with a mono- or di(alkyl)amino.

As used in the context of this invention,

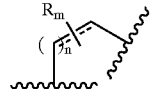

of structure (I) represents —CH$_2$CH$_2$— or —CH=CH— optionally substituted with 1 or 2 R substituents (i.e, when n=1 and m=1 or 2), or —CH₂CH₂CH₂— optionally substituted with 1, 2 or 3 R substituents (i.e., when n=2 and m=1, 2 or 3). Moieties in this regard are —CH₂CH(R)—, —CH(R)CH₂—, —CH(R)CH(R)—, —CH=C(R)—, —C(R)=CH—, —C(R)=C(R)—, —CH₂CH₂CH(R)—, —CH₂CH(R)CH₂—, —CH(R)CH₂CH₂—, —CH(R)CH₂CH(R), —CH(R)CH(R)CH₂ and —CH₂CH(R)CH(R)—, wherein each occurrence of R is the same or different and independently selected from the R groups as set forth above.

Thus, representative compounds of this invention include the following structures (Ia) through (In):

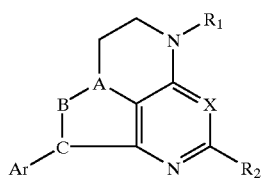
(Ia)

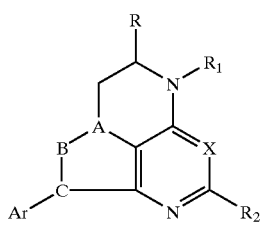
(Ib)

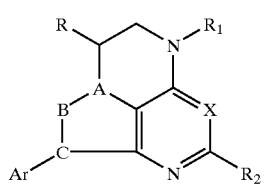
(Ic)

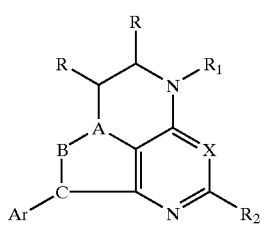
(Id)

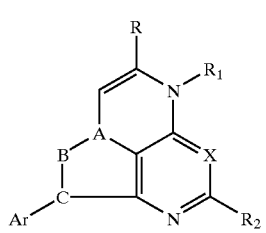
(Ie)

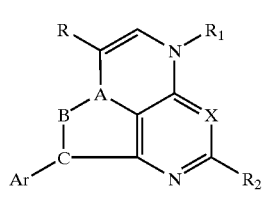
(If)

-continued

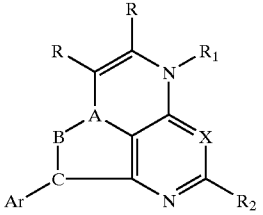
(Ig)

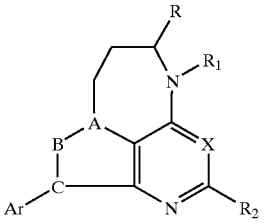
(Ih)

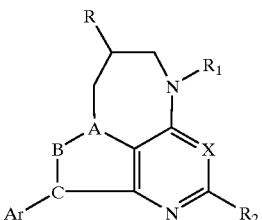
(Ii)

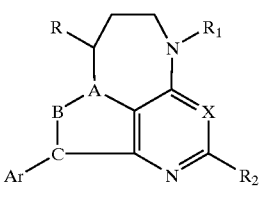
(Ij)

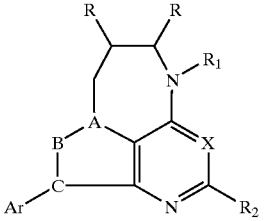
(Ik)

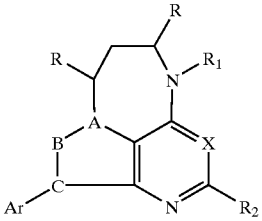
(Il)

(Im)

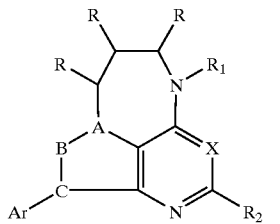
(In)

In one preferred embodiment, n is 1 and m is 0 and the CRF receptor antagonists of this invention have structure (Ia). In another preferred embodiment, n is 1 and m is 1 and the CRF receptor antagonists of this invention have structure (Ib) or (Ic).

Depending upon the choice of the A, B and C moieties, the CRF receptor antagonists of this invention include compounds having the following structures (I-1), (I-2), (I-3) and (I-4):

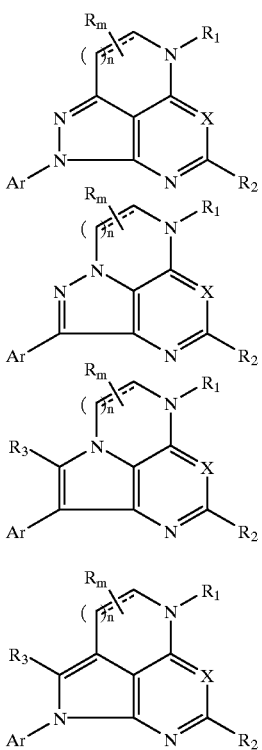

(I-1)

(I-2)

(I-3)

(I-4)

When X of compounds (I-1), (I-2), (I-3) and (I-4) is CH, representative compounds of this invention include the following compounds (I-1a), (I-2a), (I-3a), and (I-4a); and when X of compounds (I-1), (I-2), (I-3) and (I-4) is nitrogen, representative compounds of this invention include the following compounds (I-1b), (I-2b), (I-3b) and (I-4b):

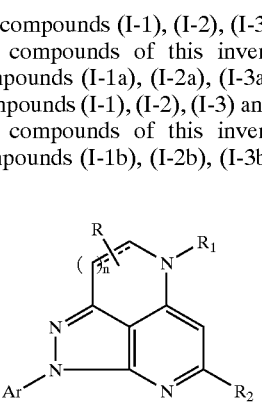

(I-1a)

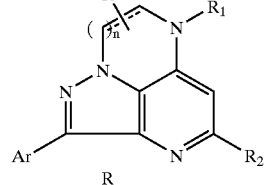
(I-2a)

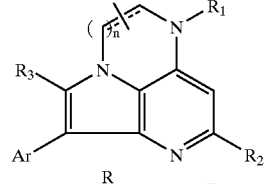
(I-3a)

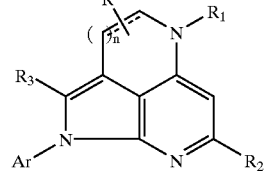
(I-4a)

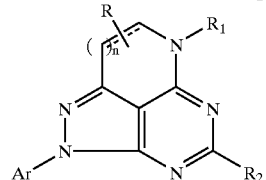
(I-1b)

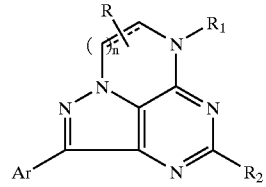
(I-2b)

(I-3b)

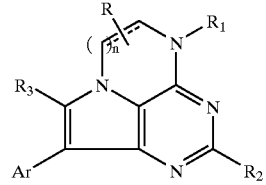
(I-4b)

In one embodiment, $R_1$ is —$SO_2R_5$, as represented by the following structure:

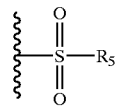

In another embodiment, $R_1$ is —$C(H)_{0,1}(R_4)(R_5)$ which represents both —$CH(R_4)(R_5)$ and —$C(R_4)(R_5)$. Representative embodiments in this regard include the following $R_1$ moieties (i), (ii) and (iii):

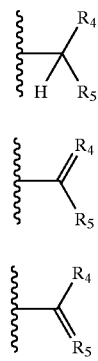

(i)

(ii)

(iii)

Representative $R_4$ moieties of this invention include, but are not limited to, hydrogen, keto (i.e., =O), halogen (fluoro, chloro, bromo and iodo), methyl, ethyl, n-propyl, n-butyl, n-penty, =CH$_2$, =CHCH$_3$, and =CHCH$_2$CH$_3$. Thus, representative $R_1$ moieties include (but are not limited to) the following:

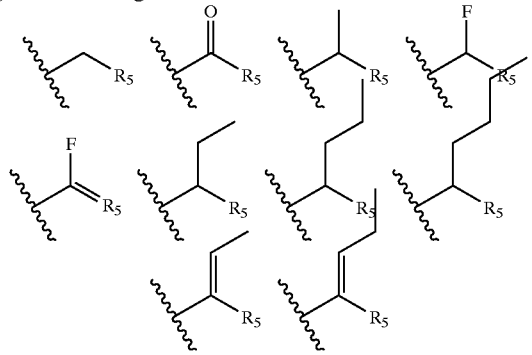

In the embodiment where the $R_4$ and $R_5$ groups of $R_1$ taken together form a cycloalkyl, the resulting $R_1$ group has the structure:

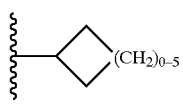

Cycloalkyls include cyclopropyl, cyclopentyl, cyclohexyl, and the like. Similarly, substituted cycloalkyls are cycloalkyls having one or more substituents as defined above. For example, in one embodiment, the cycloalkyl is substituted with one or more alkyl groups, and representative $R_1$ moieties include the following:

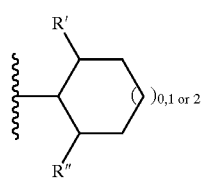

wherein R' and R" are the same or different and independently selected from, for example, alkyl such as methyl or ethyl.

In the embodiment where the $R_4$ and $R_5$ groups of $R_1$ taken together form a cycloalkylaryl, and the resulting $R_1$ group include compounds having the structure:

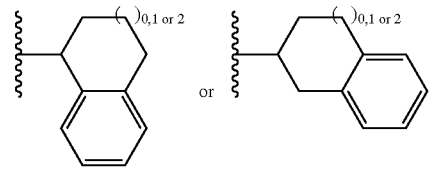

including optionally substituted analogs thereof as defined above.

In still further embodiments, $R_4$ and $R_5$ are taken together to form a cycloalkylcycloalky or cycloalkylheterocycle, and the resulting $R_1$ group include, for example, compounds having the structure:

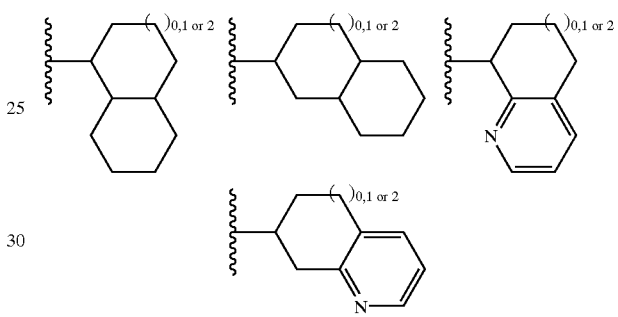

including optionally substituted analogs as defined above.

As noted above, in one embodiment, $R_5$ is a radical of the formula —Y—Z—$R_6$, wherein Y is an alkanediyl, substituted alkanediyl, or a direct bond, Z is NH, —N($R_7$), O, S, SO$_2$, C(=O), C(=O)O, OC(=O), NHC(=O), C(=O)NH, NH(SO$_2$), (SO$_2$)NH, NR$_8$C(=O)O, or a direct bond;

$R_6$ is hydrogen, alkyl, substituted alkyl, aryl, substituted aryl, arylalkyl, substituted arylalkyl, heterocyle, substituted heterocycle, heterocyclealkyl, or substituted heterocylcealkyl; or $R_7$ and $R_8$ are the same or different and independently alkyl, substituted alkyl, aryl, substituted aryl, arylalkyl, substituted arylalkyl, heterocyle, substituted heterocycle, heterocyclealkyl, or substituted heterocylcealkyl; or $R_6$ and $R_7$ taken together with the nitrogen atom to which they are attached form a heterocyle ring or substituted heterocyle ring.

In one embodiment, the $R_5$ moiety has Y as an alkanediyl, Z as a direct bond, and $R_6$ as hydrogen. Such $R_5$ moieties include alkyl, saturated alkyl, unsaturated alkyl, lower alkyl, lower saturated alkyl, lower unsaturated alkyl, saturated straight chain alkyls, saturated branched chain alkyls, saturated cyclic alkyl, unsaturated cyclic alkyl, alkenyl, straight chain alkenyl, branched chain alkenyl, alkynyl, straight chain alkynyl, and branched chain alkynyl. Representative examples are methyl, ethyl, n-propyl, iso-propyl, n-butyl, t-butyl, iso-butyl, 1-ethylpropyl (i.e., —CH(Et)$_2$) n-pentyl, n-hexyl, iso-hexyl, cyclopropyl, cyclobutyl, cyclopentyl, cyclohexyl, and ethynyl.

In another embodiment, the $R_5$ moiety has Y and Z being direct bonds while $R_6$ includes an aromatic ring, such as aryl, substituted aryl, arylalkyl, substituted arylalkyl. Representative examples are phenyl, and chlorophenyl.

In another embodiment, the $R_5$ moiety has Y being a direct bond, Z being NH and $R_6$ being as defined above. Thus, $R_6$ may be hydrogen such that $R_5$ is amino. Alternatively, $R_6$ may be alkyl, such that $R_5$ is an alkyl-substituted amino group, e.g., isopropylamino, and ethylamino. Alternatively, $R_6$ may be an aryl or substituted aryl, such that $R_5$ is an arylamino or substituted arylamino group, e.g., (methoxyphenyl)amino, ((trifluoromethoxy)phenyl)amino, (phenyl substituted phenyl)amino (also known as (biphenyl)amino), and (di(trifluoromethyl)phenyl)amino. Alternatively, $R_6$ may be arylalkyl or substituted arylalkyl, such that $R_5$ is an (arylalkyl)amino or (substituted arylalkyl)amino, e.g., (benzyl)amino (also known as (phenylmethyl)amino), (cyclopropylphenyl)amino, and (phenylethyl)amino. Accordingly to this embodiment, a preferred $R_4$ is carbonyl.

In another embodiment, the $R_5$ moiety has Y being alkanediyl, Z being $N(R_7)$ and $R_6$ being as defined above, where $R_7$ is also as defined above. Accordingly, $R_5$ is —Y—$N(R_7)(R_6)$, i.e., includes a disubstituted amino moiety. In one embodiment, Y is methylene, i.e., —$CH_2$—, so that $R_5$ is —$CH_2$—$N(R_7)(R_6)$. As defined above, $R_6$ and $R_7$ are each selected from alkyl, substituted alkyl, aryl, substituted aryl, arylalkyl, substituted arylalkyl, heterocycle, substituted heterocycle, heterocyclealkyl, or substituted heterocyclealkyl, where $R_6$ may additionally be hydrogen. In one embodiment, $R_6$ is hydrogen.

Either one or both of the $R_6$ and $R_7$ groups of —$N(R_6)(R_7)$ group may be alkyl or substituted alkyl, including saturated alkyl, unsaturated alkyl, lower alkyl, lower saturated alkyl, lower unsaturated alkyl, saturated straight chain alkyls, saturated branched chain alkyls, saturated cyclic alkyl, unsaturated cyclic alkyl, alkenyl, straight chain alkenyl, branched chain alkenyl, alkynyl, straight chain alkynyl, and branched chain alkynyl. Representative examples are methyl, ethyl, n-propyl, iso-propyl, n-butyl, t-butyl, iso-butyl, 1-ethylpropyl (i.e., —$CH(Et)_2$) n-pentyl, n-hexyl, iso-hexyl, cyclopropyl, cyclobutyl, cyclopentyl, cyclohexyl, and ethynyl.

Either one or both of the $R_6$ and $R_7$ groups of —$N(R_6)(R_7)$ group may include an aromatic ring, such as aryl, substituted aryl, arylalkyl, substituted arylalkyl. Representative examples are phenyl, and chlorophenyl.

Thus, —$N(R_6)(R_7)$ may be, for example, (propyl)(cyclopropylmethyl) amino, (2-cyanoethyl)(methyl)amino, (2-cyanoethyl)(benzyl)amino, (ethyl)((2-(dimethylamino)ethyl))amino, (2-hydroxyethyl)(benzyl)amino, di(2-hydroxyethyl)amino, (propyl)(2-hydoxyethyl)amino, (cyclohexyl)(ethyl)amino, (carboxymethyl)(methyl)amino, di(benzyl)amino, and ((2-hydroxy)(2-phenyl)ethyl))(methyl)amino.

As stated above, $R_6$ and $R_7$ taken together with the nitrogen atom to which they are both attached may form a heterocycle ring or substituted heterocycle ring. Thus, —$N(R_6)(R_7)$ may represent a heterocycle ring, such as aziridinyl, methyl-substituted aziridinyl, 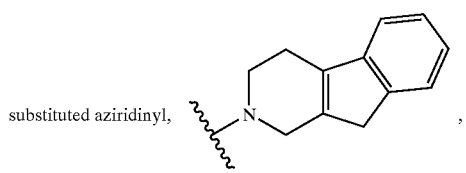 , -continued

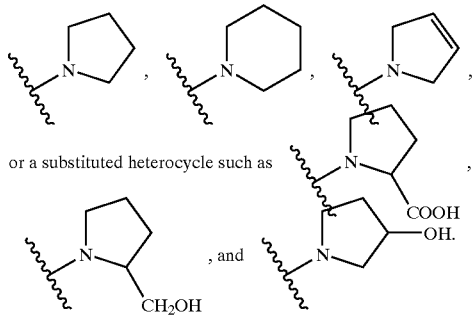

or a substituted heterocycle such as

A heterocycle, as defined above, may include more heteroatoms (i.e., non-carbon atoms) than the nitrogen of —$N(R_6)(R_7)$. For instance, the heterocycle may additionally include a second nitrogen, or an oxygen, or a sulfur. When a second nitrogen is present, the heterocycle will have two nitrogens, as in, e.g., piperazinyl. When an oxygen is present, the heterocycle will have both an oxygen and a nitrogen, as in, e.g., morpholinyl. When a sulfur is present, the heterocycle will have both a sulfur and a nitrogen, as in, e.g., thiomorpholinyl. These heterocycles having two or more heteroatoms may be substituted or non-substituted. For instance, the morpholinyl group may be substituted with two alkyl group, e.g, one methyl group on either side of the morpholinyl oxygen atom. When the heterocycle is a piperazinyl group, the nitrogen atom not explicitly shown in the formula —$N(R_6)(R_7)$ may be substituted, where exemplary substituents are, for example, alkyl (e.g., methyl), substituted alkyl (e.g., 2-hydroxyethyl), or arylalkyl (e.g., benzyl).

In another embodiment, Y is substituted alkanediyl, Z is a heteroatom or a direct bond, and $R_6$ is as defined above. In a preferred embodiment, $R_4$ is hydrogen. Thus, Y is an alkanediyl having a subsituent, where the substituent may be, for example, hydroxy. The alkanediyl may be, for example, ethylene (i.e., —$CH_2$—$CH_2$—), or n-propylene (i.e., —$CH_2CH_2CH_2$—), such that a substituted alkanediyl may be, e.g., —$CH(OH)$—$CH_2$—, or —$CH_2$—$CH(OH)$—$CH_2$—.

In another embodiment, Y is alkanediyl, e.g., methylene (—$CH_2$—), Z is amido, i.e., —$NHC(=O)$— or —$C(=O)NH$—, and $R_6$ is as defined above. In a preferred embodiment, R4 is hydrogen. Thus, in one embodiment, $R_5$ is —$CH_2$—$NHC(=O)$—$R_6$.

In another embodiment, Y is alkanediyl, e.g., methylene (—$CH_2$—), Z is sulfonylamido, i.e., —$NHSO_2$— or —$SO_2NH$—, and $R_6$ is as defined above. In a preferred embodiment, $R_4$ is hydrogen. Thus, in this embodiment, $R_5$ is —$CH_2$—$NHSO_2$—$R_6$.

In another embodiment, Y and Z are direct bonds and $R_6$ is as defined above. Thus, in this embodiment, $R_5$ is —$R_6$. In one embodiment, R4 is alkyl when $R_5$ is —$R_6$. In another embodiment, $R_4$ is carbonyl when $R_5$ is —$R_6$. The $R_6$ moiety may be alkyl, saturated alkyl, unsaturated alkyl, lower alkyl, lower saturated alkyl, lower unsaturated alkyl, saturated straight chain alkyls, saturated branched chain alkyls, saturated cyclic alkyl, unsaturated cyclic alkyl, alkenyl, straight chain alkenyl, branched chain alkenyl, alkynyl, straight chain alkynyl, and branched chain alkynyl. Representative examples are methyl, trifluoromethyl, ethyl, n-propyl, iso-propyl, n-butyl, t-butyl, iso-butyl, 1-ethylpropyl (i.e., —$CH(Et)_2$) n-pentyl, n-hexyl, iso-hexyl, cyclopropyl, cyclobutyl, cyclopentyl, cyclohexyl, and ethynyl. The $R_6$ may be substituted alkyl, where a substituted alkyl may have one, two, or more substituents.

In another embodiment, Y and Z are direct bonds and $R_6$ is as defined above. Thus, in this embodiment, $R_5$ is —$R_6$. In one embodiment, $R_4$ is hydrogen when $R_5$ is —$R_6$. In another embodiment, $R_4$ is alkyl when $R_5$ is —$R_6$.

In another embodiment, Y is a direct bond, Z is an ester group, i.e., —C(=O)O— or —OC(=O)—, and $R_6$ is as defined above. In this embodiment, $R_5$ is -ester-$R_6$, and preferably $R_5$ is —C(=O)—O—$R_6$. In a one embodiment, $R_4$ is hydrogen. The $R_6$ moiety may be alkyl, preferably lower saturated alkyl, e.g., methyl, ethyl, propyl, etc.

In another embodiment, Y is substituted alkanediyl, Z is a direct bond or oxygen, and $R_6$ is as defined above. In this embodiment, $R_4$ is preferably H. In an alternative embodiment, $R_4$ is preferably alkyl. The alkanediyl may be a $C_1$–$C_6$ alkanediyl, e.g., methylene, ethylene, propylene, etc., and the substituent on the alkanediyl may be, e.g, hydroxy, halogen, amino, alkyl, etc. Accordingly, Y may be —CH(OH)— or —CH(OH)—CH$_2$—, etc. In one embodiment, $R_6$ is aryl or substituted aryl, e.g., phenyl or chlorophenyl. In another embodiment, $R_6$ is alky or substituted alkyl, e.g, methyl or fluoromethyl.

In another embodiment, $R_1$ is SO$_2$R$_5$, where Y is a direct bond, Z is a direct bond, and $R_6$ is as defined above. Accordingly, in this embodiment, $R_1$ is —SO$_2$—$R_6$.

In another embodiment, Y is alkanediyl, Z is O or S, and $R_6$ is as defined above. For example, $R_5$ may be —CH$_2$—O—CH$_3$ where Y is methylene, Z is O, and $R_6$ is an alkyl and specifically methyl. In a preferred embodiment, $R_4$ is carbonyl. In another preferred embodiment, $R_4$ is hydrogen. In yet another preferred embodiment, $R_4$ is alkyl.

In another embodiment, Y is a direct bond, Z is a direct bond, and $R_6$ is alkyl or substituted alkyl of the formula =CH$_2$, =CH—CH$_3$, =CH—CH$_2$—CH$_3$, =CH—CH(CH$_3$)—CH$_3$, and homologs thereof. The substituent on the substituted alkyl may be, for example, hydroxyl or halogen (e.g., fluoro).

The $R_6$ moiety may be alkyl, saturated alkyl, unsaturated alkyl, lower alkyl, lower saturated alkyl, lower unsaturated alkyl, saturated straight chain alkyls, saturated branched chain alkyls, saturated cyclic alkyl, unsaturated cyclic alkyl, alkenyl, straight chain alkenyl, branched chain alkenyl, alkynyl, straight chain alkynyl, and branched chain alkynyl. Representative examples are methyl, ethyl, n-propyl, iso-propyl, n-butyl, t-butyl, iso-butyl, 1-ethylpropyl (i.e., —CH(Et)$_2$) n-pentyl, n-hexyl, iso-hexyl, cyclopropyl, cyclobutyl, cyclopentyl, cyclohexyl, and ethynyl.

The $R_6$ moiety may be substituted alkyl, where substituted alkyls may have one or may substituents. Suitable substituents include trifluoromethyl, hydroxy, and halogen (i.e., fluoro, chloro, bromo, iodo).

The $R_6$ moiety may include an aromatic ring, such as aryl, substituted aryl, arylalkyl, substituted arylalkyl. Representative examples are phenyl, methoxyphenyl, and chlorophenyl.

The $R_6$ moeity may be heterocycle, heterocyclealkyl, substituted heterocycle, substituted heterocyclealkyl, e.g., furanyl, furanylmethyl, and thienyl, thienymethyl.

In a preferred embodiment, $R_4$ is hydrogen when $R_5$ is —$R_6$ and $R_6$ is alkyl as set forth above. In another embodiment, $R_4$ is alkyl when $R_5$ is —$R_6$ and $R_6$ is alkyl as set forth above. In a preferred embodiment, $R_4$ is hydrogen when $R_5$ is —$R_6$ and $R_6$ includes an aromatic ring as set forth above. In another embodiment, $R_4$ is alkyl when $R_5$ is —$R_6$ and $R_6$ includes an aromatic ring as set forth above.

Representative $R_1$ groups of this invention specifically include each of the $R_1$ groups disclosed in the Examples, as well as methyl, ethyl, n-propyl, iso-propyl, n-butyl, iso-butyl, tert-butyl, n-pentyl, iso-pentyl, neo-pentyl, —CH(ethyl)$_2$, —CH(n-propyl)$_2$, —CH(n-butyl)$_2$, —CH$_2$CH$_2$OCH$_3$, —CH(methyl)(CH$_2$OCH$_3$), —CH(ethyl)(CH$_2$OCH$_3$), —CH(n-propyl)(CH$_2$OCH$_3$), —CH(n-butyl)(CH$_2$OCH$_3$), —CHC≡CH, —CH(methyl)(ethyl), —CH(methyl)(n-propyl), —CH(methyl)(n-butyl), —CH(methyl)(n-pentyl), —CH(methyl)(CH$_2$CH$_2$CH$_2$CH(CH$_3$)$_2$), —CH(ethyl)(n-propyl), —CH(ethyl)(n-butyl), —CH(ethyl)(n-pentyl), ), —CH(n-propyl)(n-butyl), —CH(n-propyl)(n-pentyl), cyclopropyl, cyclobutyl, cyclohexyl, 2-methylcyclohexyl, 3-methylcyclohexyl, 1,2,3,4-tetrahydronaphthyl (1 and 2), benzyl, 2-chlorobenzyl, —CH(methyl)(benzyl), —CH(ethyl)(benzyl), —CH(n-propyl)(benzyl), —CH(n-butyl)(benzyl), —CH$_2$(cyclopropyl), —CH$_2$(cyclobutyl), —CH$_2$CH(methyl)CH$_2$CH$_3$, —CH$_2$CH(ethyl)CH$_2$CH$_3$, —CH$_2$C(CH$_3$)$_3$, —CH$_2$C≡CH, —CH$_2$C(=O)CH$_2$CH$_3$, —C(=O)cyclopropyl, —C(=O)NHbenzyl, Representative optional R groups of this invention include, when present, methyl, ethyl, n-propyl, iso-propyl, iso-butyl, =CH$_2$ and =CHCH$_3$.

In more specific embodiments of this invention, representative Ar groups of this invention include (but are not limited to) the Ar groups identified in the Examples, as well as 2,4-dichlorophenyl, 2,4-dimethyl-phenyl, 2-chloro-4-methylphenyl, 2-methyl-4-chlorophenyl, 2,4,6-trimethylphenyl, 2-chloro-4-methoxyphenyl, 2-methyl-4-methoxyphenyl, 2,4-dimethoxyphenyl, 2-trifluoromethyl-4-chlorophenyl, 3-methoxy-4-chlorophenyl, 2,5-dimethoxy-4-chlorophenyl, 2-methoxy-4-trichloromethylphenyl, 2-methoxy-4-isopropylphenyl, 2-methoxy4-trifluoromethylphenyl, 2-methoxy-4-isopropylphenyl 2-methoxy-4-methylphenyl, 4-methyl-6-dimethylaminopyridin-3-yl, 4-dimethylamino-6-methyl-pyridin-3-yl, 6-dimethylamino-pyridin-3-yl and 4-dimethylamino-pyridin-3-yl.

In another embodiment, compounds of this invention have structure (I) above, wherein $R_4$ is hydrogen, keto, $C_{1-6}$alkyl, mono- or di($C_{3-6}$cycloalkyl)methyl, $C_{3-6}$cycloalkyl, $C_{3-6}$alkenyl, hydroxy$C_{1-6}$alkyl. $C_{1-6}$alkylcarbonyloxy$C_{1-6}$alkyl, or $C_{1-6}$alkyloxy$C_{1-6}$alkyl; $R_5$ is hydrogen, Ar, $C_{1-6}$alkylAr, OAr, $C_{1-3}$alkyl, $C_{3-6}$cycloalkyl, O($C_{1-8}$alkyl), mono- or di($C_{3-6}$cycloalkyl) methyl, $C_{3-6}$alkenyl, $C_{3-6}$alkynyl, $C_{1-6}$alkyloxy$C_{1-6}$alkyl, $C_{1-6}$alkyloxyAr, hydroxy$C_{1-6}$alkyl, thienyl$C_{1-6}$alkyl, furanyl$C_{1-6}$alkyl, $C_{1-6}$alkylthio$C_{1-6}$alkyl, morpholinyl, mono- or di($C_{1-6}$alkyl)amino$C_{1-6}$alkyl, amino, ($C_{1-6}$alkyl)amino, di($C_{1-6}$alkyl)amino, ($C_{1-6}$alkylAr)amino, ($C_{1-6}$alkyl)(Ar)amino, $C_{1-6}$alkylcarbonyl$C_{1-6}$alkyl, sulfonyl($C_{1-8}$alky), —C(=O)$C_{1-6}$alkyl, C,alkyl substituted with imidazolyl, or a radical of the formula —($C_{1-6}$alkanediyl)—O—(CO)$_{0-1}$—Ar; or $R_4$ and Rs taken together form a $C_{3-8}$cycloalkyl or a $C_{5-8}$cycloalkyl fused to Ar optionally substituted with one or more substituents independently selected from $C_{1-6}$alkyl; and Ar is, at each occurrence, independently phenyl or naphthyl, optionally substituted with 1, 2 or 3 substituents independently selected from halo, $C_{1-6}$alkyl, triflouromethyl, cyano, $C_{1-6}$alkyloxy, benzyloxy, $C_{1-6}$alkylthio, nitro, amino, and mono- or di($C_{1-6}$alkyl) amino; or an aromatic $C_{3-12}$heterocycle optionally substituted with 1, 2 or 3 substituents independently selected from halo, $C_{1-6}$alkyl, triflouromethyl, hydroxy, cyano, $C_{1-6}$alkyloxy, benzyloxy, $C_{1-6}$alkylthio, nitro, amino, mono- or di($C_{1-6}$alkyl)amino, and piperidinyl.

The compounds of the present invention may be prepared by known organic synthesis techniques, including the methods described in more detail in the Examples, and may generally be utilized as the free base. Alternatively, the compounds of this invention may be used in the form of acid addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of structure (I) is intended to encompass any and all acceptable salt forms.

In general, the compounds of structure (I) may be made according to the organic synthesis techniques known to those skilled in this field, as well as by the representative methods set forth in the Examples. For example, the synthesis of structure (I) will generally proceed by synthesis of the desired sub-structure (I-1), (I-2), (I-3) or (I-4), as represented below. In turn, synthesis of each of these sub-structures is exemplified in the Examples.

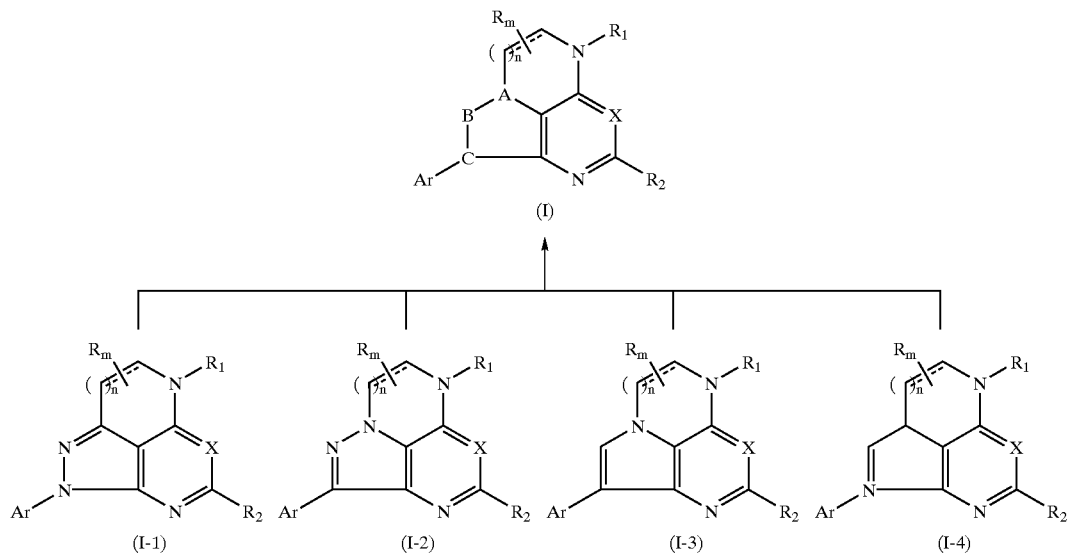

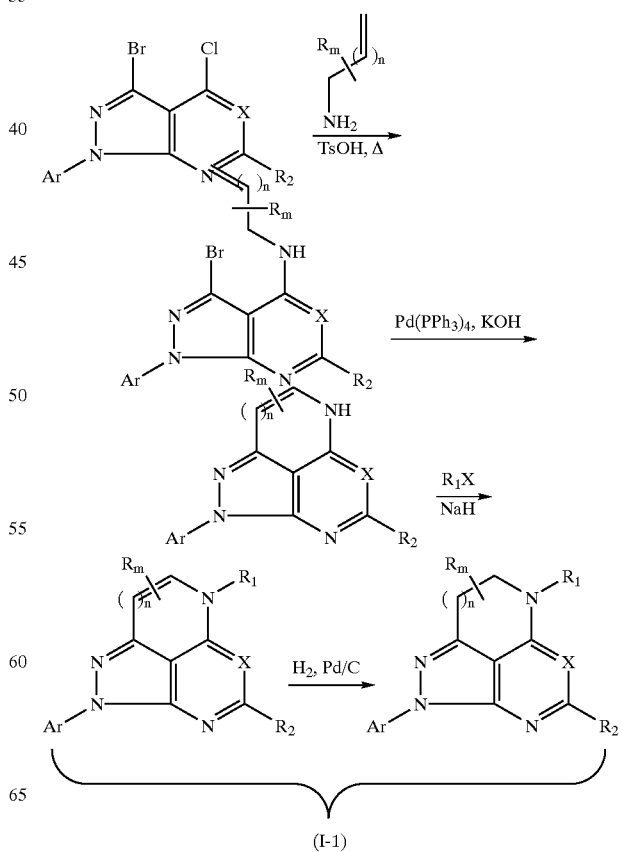

General Synthesis of Structure (I-2)
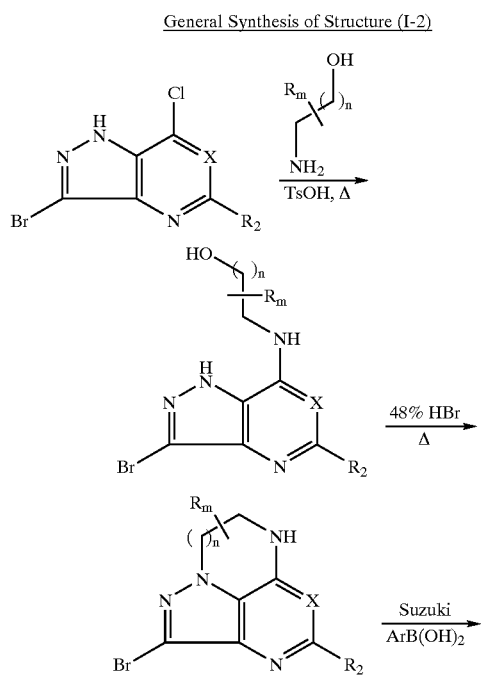
(I-2)
General Synthesis of Structure (I-3)
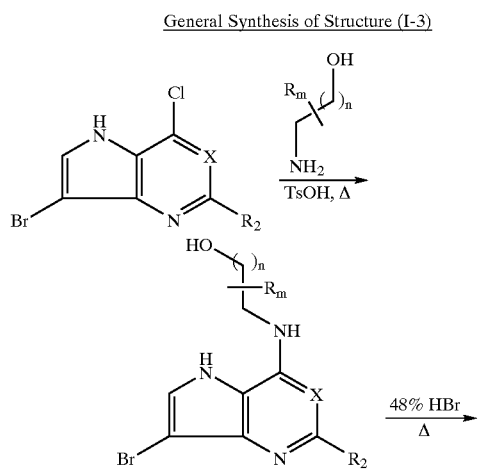
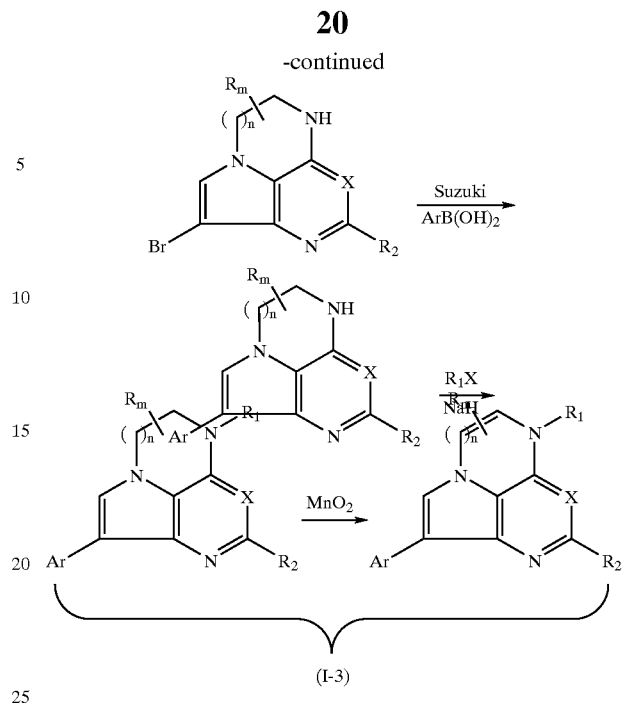
(I-3)
General Synthesis of Structure (I-4)
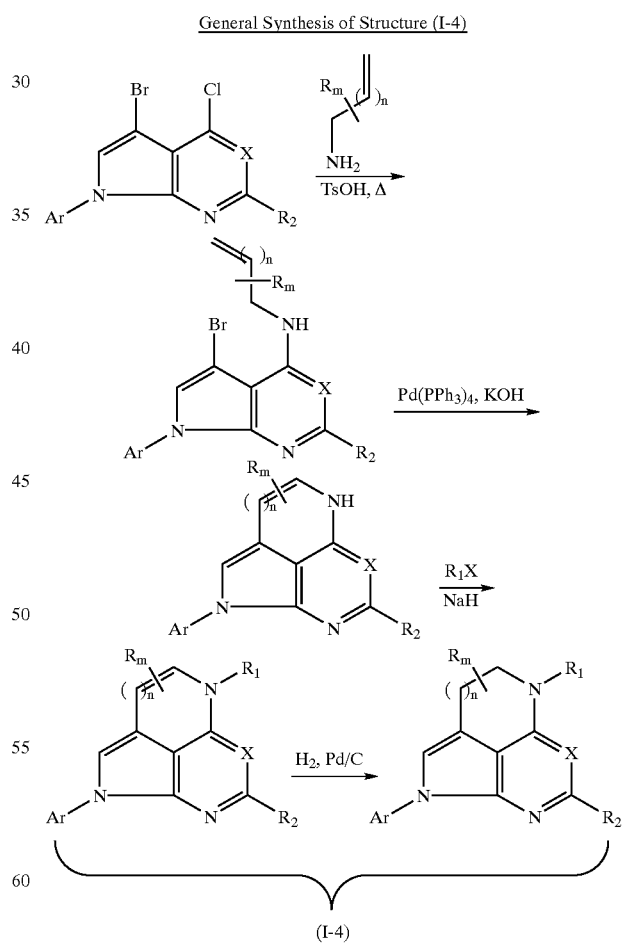
(I-4)
In addition, compounds of structure (I-1) and (I-4) may be made by the following Reaction Scheme A by synthesis of intermediate 4, which is then converted to the corresponding structure (I-1) (structure "10") or (I-4) (structure "8"):

Reaction Scheme A
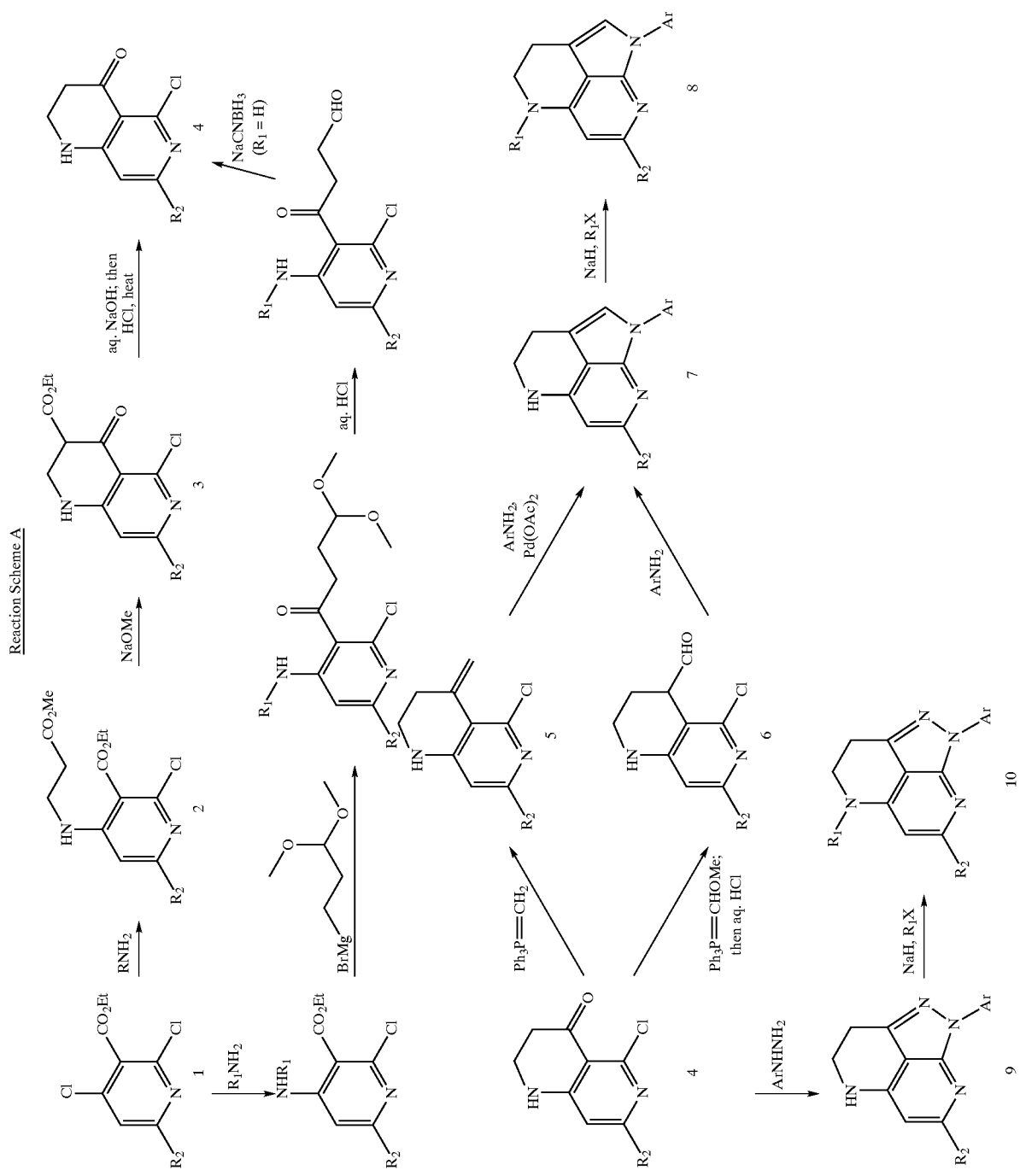

Compounds of structutres (1-1) and (1-4) may also be made according to the following Reaction Schemes B and C:

Reaction Scheme B

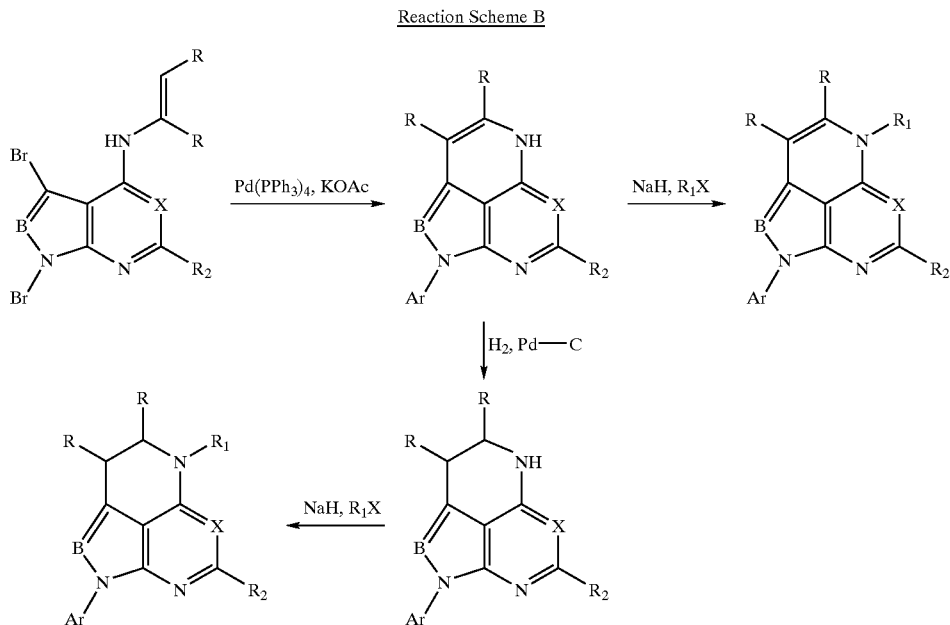

Reaction Scheme C

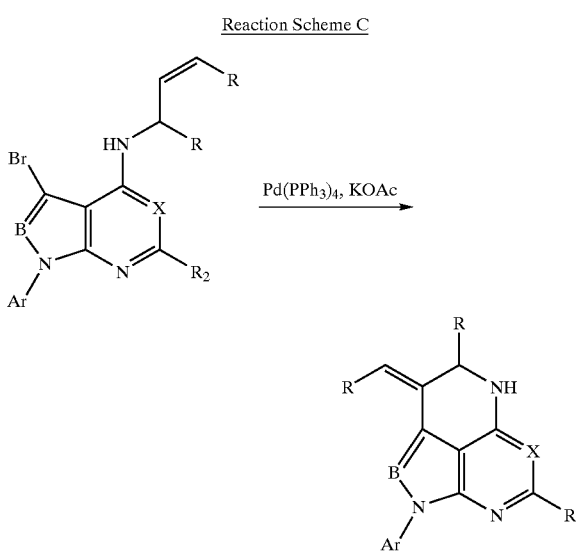

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse* 1:572, 1987). As mentioned above, suitable CRF antagonists include compounds which demonstrate CRF receptor affinity. CRF receptor affinity may be determined by binding studies that measure the ability of a compound to inhibit the binding of a radiolabeled CRF (e.g., [$^{125}$I]tyrosine-CFR) to its receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)).

With reference to CRF receptor binding affinities, CRF receptor antagonists of this invention have a $K_i$ of less than 10 μM. In a preferred embodiment of this invention, a CRF receptor antagonist has a $K_i$ of less than 1 μM, and more preferably less than 0.25 μM (i.e., 250 nM). As set forth in greater detail below, the $K_i$ values of representative compounds of this invention were assayed by the methods set forth in Example 9. Preferred compounds having a $K_i$ of less than 1 μM are compound numbers I-2a-1 to I-2a-6, I-2a-8. I-2a-9, I-2a-12 to I-2a-25, I-2a-27 to I-2a-44, I-2a-46 to I-2a-76, I-4b-1 and I-4b-2. More preferred compounds having a $K_i$ of less than 250 nM are compound numbers I-2a-1 to I-2a-4, I-2a-6, I-2a-8, I-2a-9, I-2a-12 to I-2a-18, I-2a-20 to I-2a-25, I-2a-28 to 1-2a-36, I-2a-38 to I-2a-43, I-2a-46 to I-2a-73, I-2a-76, I-4b-1 and I-4b-2.

The CRF receptor antagonists of the present invention demonstrate activity at the CRF receptor site, and may be used as therapeutic agents for the treatment of a wide range of disorders or illnesses including endocrine, psychiatric, and neurologic disorders or illnesses. More specifically, the CRF receptor antagonists of the present invention may be useful in treating physiological conditions or disorders arising from the hypersecretion of CRF. Because CRF is believed to be a pivotal neurotransmitter that activates and coordinates the endocrine, behavioral and automatic responses to stress, the CRF receptor antagonists of the present invention can be used to treat neuropsychiatric disorders. Neuropsychiatric disorders which may be treatable by the CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF antagonists may also be useful in treating stress-induced immune suppression associated with various diseases states, as well as stroke. Other uses of the CRF antagonists of this invention include treatment of inflammatory conditions (such as rheumatoid arthritis, uveitis, asthma, inflammatory bowel disease and G.I. motility), Cushing's disease, infantile spasms, epilepsy and other seizures in both infants and adults, and various substance abuse and withdrawal (including alcoholism).

In another embodiment of the invention, pharmaceutical compositions containing one or more CRF receptor antagonists are disclosed. For the purposes of administration, the compounds of the present invention may be formulated as pharmaceutical compositions. Pharmaceutical compositions of the present invention comprise a CRF receptor antagonist of the present invention (i.e., a compound of structure (I)) and a pharmaceutically acceptable carrier and/or diluent. The CRF receptor antagonist is present in the composition in an amount which is effective to treat a particular disorder— that is, in an amount sufficient to achieve CRF receptor antagonist activity, and preferably with acceptable toxicity to the patient. Preferably, the pharmaceutical compositions of the present invention may include a CRF receptor antagonist in an amount from 0.1 mg to 250 mg per dosage depending upon the route of administration, and more preferably from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain in addition to a CRF receptor antagonist, diluents, dispersing and surface active agents, binders, and lubricants. One skilled in this art may further formulate the CRF receptor antagonist in an appropriate manner, and in accordance with accepted practices, such as those disclosed in *Remington's Pharmaceutical Sciences*, Gennaro, Ed., Mack Publishing Co. Easton, Pa. 1990.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of an carboxylic acid (—COOH), esters may be employed, such as methyl esters, ethyl esters, and the like.

With regard to stereoisomers, the compounds of structure (I) may have chiral centers and may occur as recemates, reacemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

In another embodiment, the present invention provides a method for treating a variety of disorders or illnesses, including endocrine, psychiatric and neurologic disorders or illnesses. Such methods include administering of a compound of the present invention to a warm-blooded animal in an amount sufficient to treat the disorder or illness. Such methods include systemic administration of a CRF receptor antagonist of this invention, preferably in the form of a pharmaceutical composition. As used herein, systemic administration includes oral and parenteral methods of administration. For oral administration, suitable pharmaceutical compositions of CRF receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the CRF receptor antagonist, buffers, antioxidants, bacteriostats, and other additives commonly employed in such solutions.

As mentioned above, administration of a compound of the present invention can be used to treat a wide variety of disorders or illnesses. In particular, the compounds of the present invention may be administered to a warm-blooded animal for the treatment of depression, anxiety disorder, panic disorder, obsessive-compulsive disorder, abnormal aggression, unstable angina, reactive hypertension, anorexia nervosa, bulimia, irritable bowel syndrome, stress-induced immune suppression, stroke, inflammation, Cushing's disease, infantile spasms, epilepsy, and substance abuse or withdrawal.

The following examples are provided for purposes of illustration, not limitation.

EXAMPLES

The CRF receptor antagonists of this invention may be prepared by the methods disclosed in Examples 1–12. Example 13 presents a method for determining the receptor binding activity (KC), and Example 14 discloses an assay for screening compounds of this invention for CRF-stimulated adenylate cyclase activity.

Example 1
Synthesis of Representative Compounds of Structure (I-1)
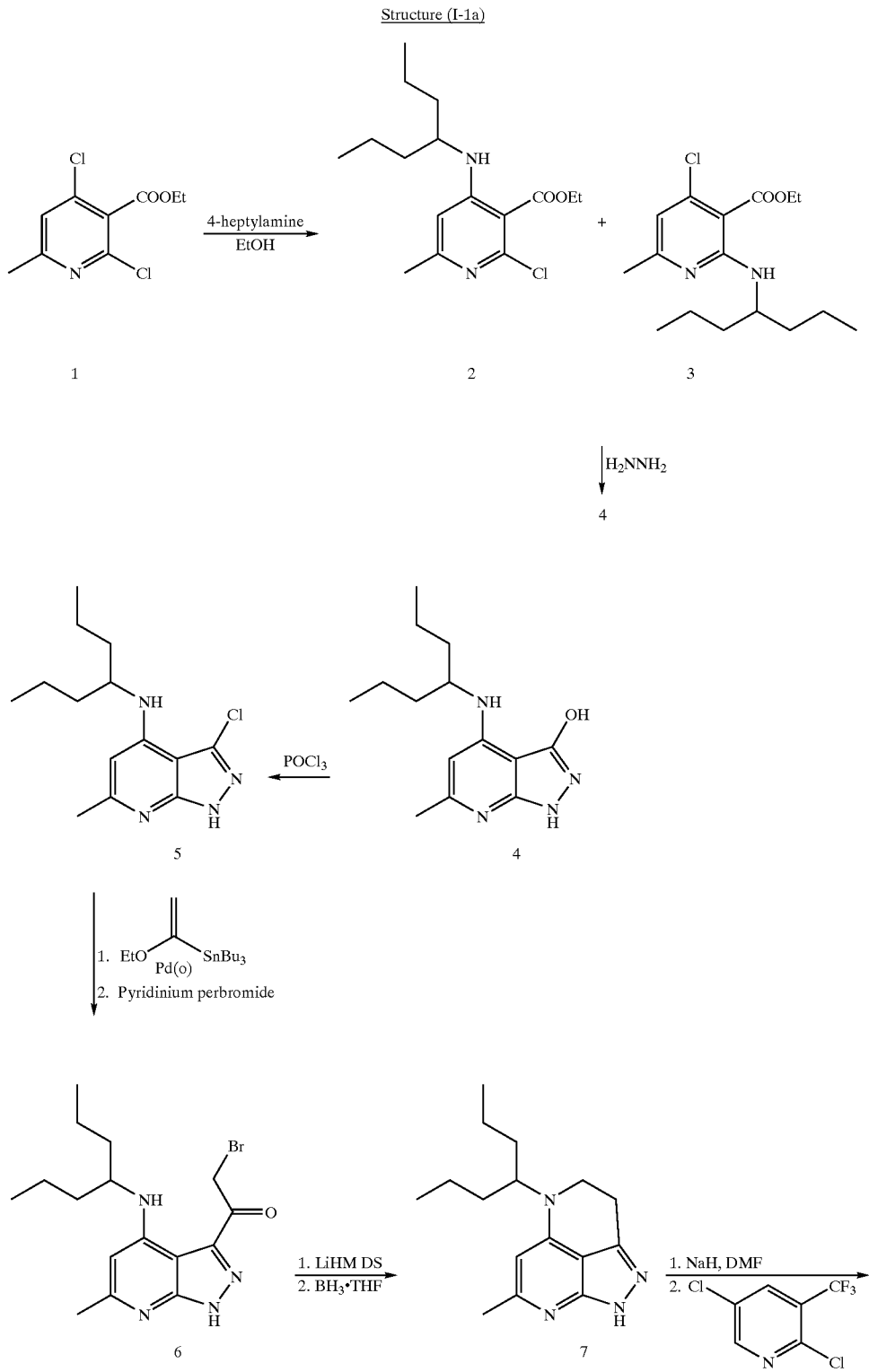

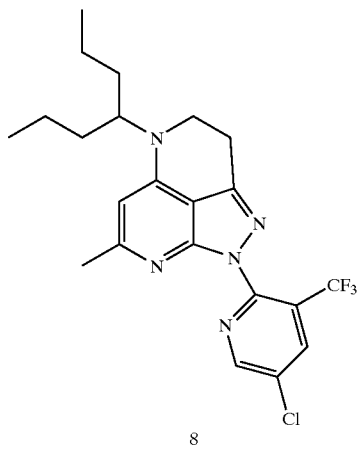

8

Compound (2)

2,4-dichloro-6-methyl-3-ethylester pyridine (1) (5.0 g, 21.36 mmoles), 4-heptylamine (21.36 mmoles) and triethyl amine (2.97 ml, 21.36 mmole) in ethanol were heated at reflux over night. Ethanol was evaporated and the residue was dissolved in ethyl acetate, washed with saturated solution of bicarbonate and brine. The organic layer was dried over sodium carbonate and concentrated in vacuum. Compound (2) was separated from (1) and (3) by silica gel column eluting with ethyl acetate-hexane.

Compound (4)

Compound (2) (20.0 mmoles) and hydrazine (25.0 mmoles) in ethanol was refluxed over night. Ethanol was evaporated and the residue was dissolved in ethyl acetate, washed with water, dried over sodium sulfate and concentrated in vacuum to give compound (4) which was used in the next step without further purification.

Compound (5)

A mixture of compound (4) (15.0 mmoles) and phosphorus oxychloride (15 ml) was refluxed for 3 hours, cooled, poured onto ice and neutralized by 1N NaOH. The aqueous layer was extracted by ethyl acetate. The organic layer was washed with brine, dried under sodium sulfate, and concentrated to yield the desired compound (5).

Compound (6)

To a solution of compound (5) (15.0 mmoles) in THF were added tri-n-butyl (1-ethoxy) vinyl tin (10.0 mmoles) and bis(triphenylphosphine) palladium (II) chloride (10% mole). The mixture was refluxed for 24 hours. The solution was partitioned between ethyl acetate and water. The organic phase washed with brine dried over sodium sulfate and concentrated in vacuum. The residue was dissolved in $CCl_4$ and added at ice bath temperature to a suspension of pyridinium perbromide (75.0 mmoles) in $CCl_4$. The temperature was raised to room temperature and stirred for 4 hours. The mixture was diluted with chloroform and washed successively with brine, hydrochloric acid solution (10%), saturated solution of bicarbonate, dried over sodium carbonate and concentrated in vacuum. Compound (6) was purified by silica gel column.

Compound (7)

To a solution of compound (6) (10.0 mmoles) in THF was added 1 M lithium hexamethyldisilizane in THF (11.0 mmoles) and the mixture was stirred at room temperature over night. The mixture was neutralized by 1N HCl diluted with ethyl acetate. The organic layer was washed with brine, dried over sodium sulfate and concentrated in vacuum. The residue was dissolved in THF and $BH_3$-THF (1M) was added and the reaction was refluxed for 8 hours. The mixture was hydrolyzed with 1N HCl and diluted with ethyl acetate, the organic layer was washed with saturated solution of sodium bicarbonate and brine then concentrated in vacuum to give compound (7).

Compound (8)

To a solution of compound (7) (0.5 mmoles) in DMF was added NaH (0.6 mmoles) followed by 2,3-chloro-5-trifluomethyl-pyridine (0.6 mmoles). The mixture was heated at 90° C. over night. The reaction mixture was neutralized with 1N HCl and partitioned between water and ethyl acetate. The organic layer was washed with saturated solution of sodium bicarbonate and brine and concentrated in vacuum. Compound (8) was purified by silica gel column eluting with ethyl acetate-hexane.

Compounds of structure (I-1b) may be made in the same manner, but using 2,4-dichloro-6-methyl-3-ethylester pyrimidine (1') in place of the corresponding pyridine (1), as illustrated by the following reaction scheme.

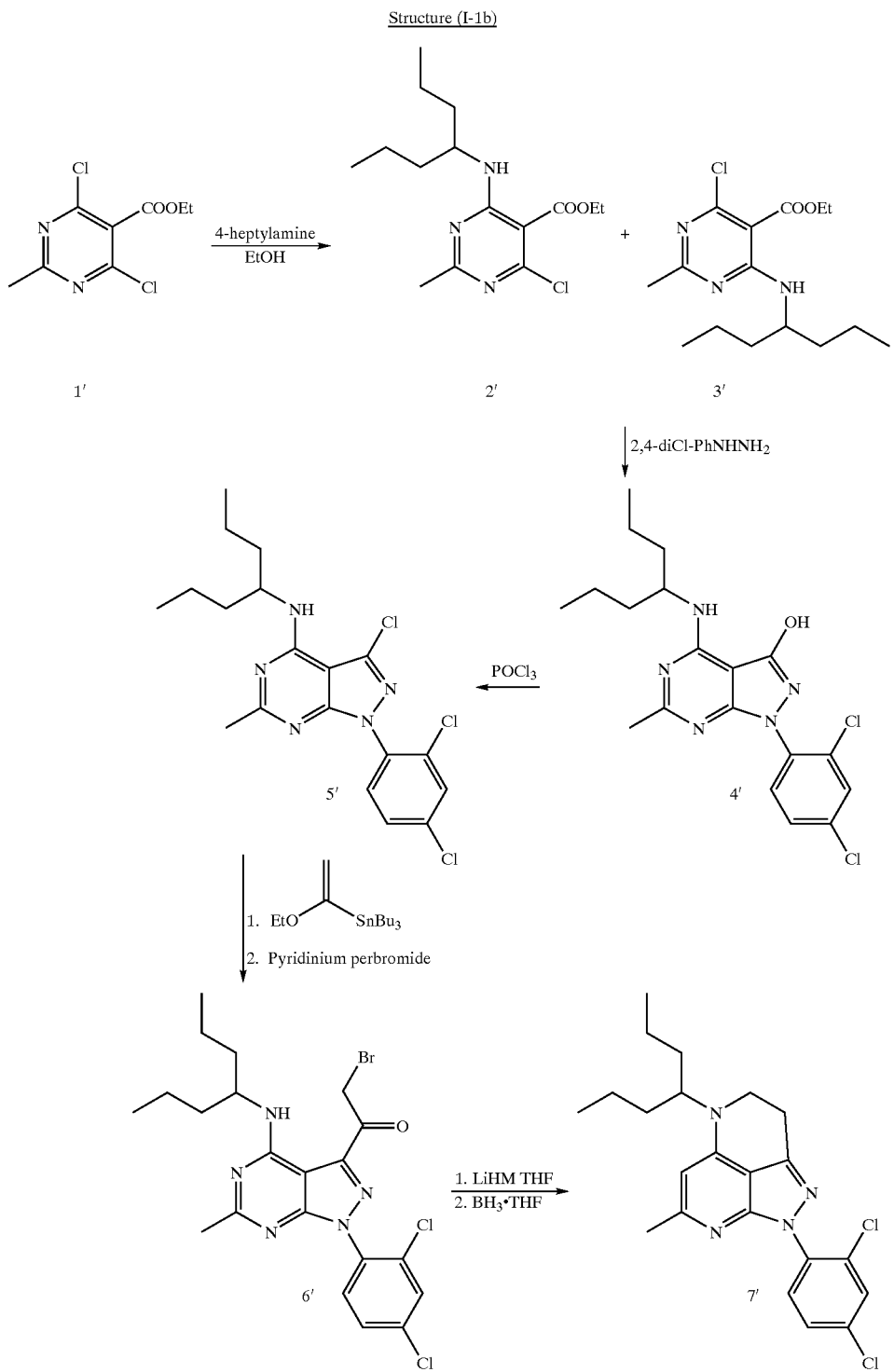

Compound (4')

Compound (2') (20.0 mmoles) and 2,4-dichlorophenlyhydrazine (25.0 mmoles) in ethanol was refluxed overnight. Ethanol was evaporated and the residue was dissolved in ethyl acetate, washed with water, dried over sodium sulfate and concentrated in vacuum to give compound (4') which was used in the next step without further purification.

Compound (5')

A mixture of (4') (15.0 mmoles) and phosphorus oxychloride (15 ml) was refluxed for 3 hours, cooled, poured onto ice and neutralized by 1N NaOH. The aqueous layer was extracted by ethyl acetate. The organic layer was washed with brine, dried under sodium sulfate, concentrated to yield the desired product (5').

Compound (6')

To a solution of compound (5') (15.0 mmoles) in THF were added tri-n-butyl (1-ethoxy) vinyl tin (10.0 mmoles) and bis(triphenylphosphine) palladium (II) chloride (10.0% mole). The mixture was refluxed for 24 hours. The solution was partitioned between ethyl acetate and water. The organic phase washed with brine dried over sodium sulfate and concentrated in vacuum. The residue was dissolved in CC14 and added at ice bath temperature to a suspension of pyridinium perbromide (75.0 mmoles) in CC14. The temperature was rised to room temperature to a suspension of pyridinium perbromide (75.0 mmoles) in CC14. The temperature was rised to room temperature and stirred for 4 hours. The mixture was diluted with chloroform and washed successively with brine, hydrochloric acid solution (10%), saturated solution of bicarbonate, dried over sodium carbonate and concentrated in vacuum. The compound (6') was purified by silica gel column.

Compound (7')

To a solution of (6') (10.0 mmoles) in THF was added sodium hydride (11.0 mmoles) and the mixture was stirred at room temperature overnight. The mixture was neutralized by 1N HCl diluted with ethyl acetate. The organic layer was washed with brine, dried over sodium sulfate and concentrated in vacuum. The residue was dissolved in THF and $BH_3$-THF (1M) was added and the reaction was refluxed for 8 hours. The mixture was hydrolyzed with 1N HCl and diluted with ethyl acetate, the organic layer was washed with saturated solution of sodium bicarbonate and brine then concentrated in vacuum to give compound (7').

Example 2

Synthesis of Representative Compounds of Structure (I-2)

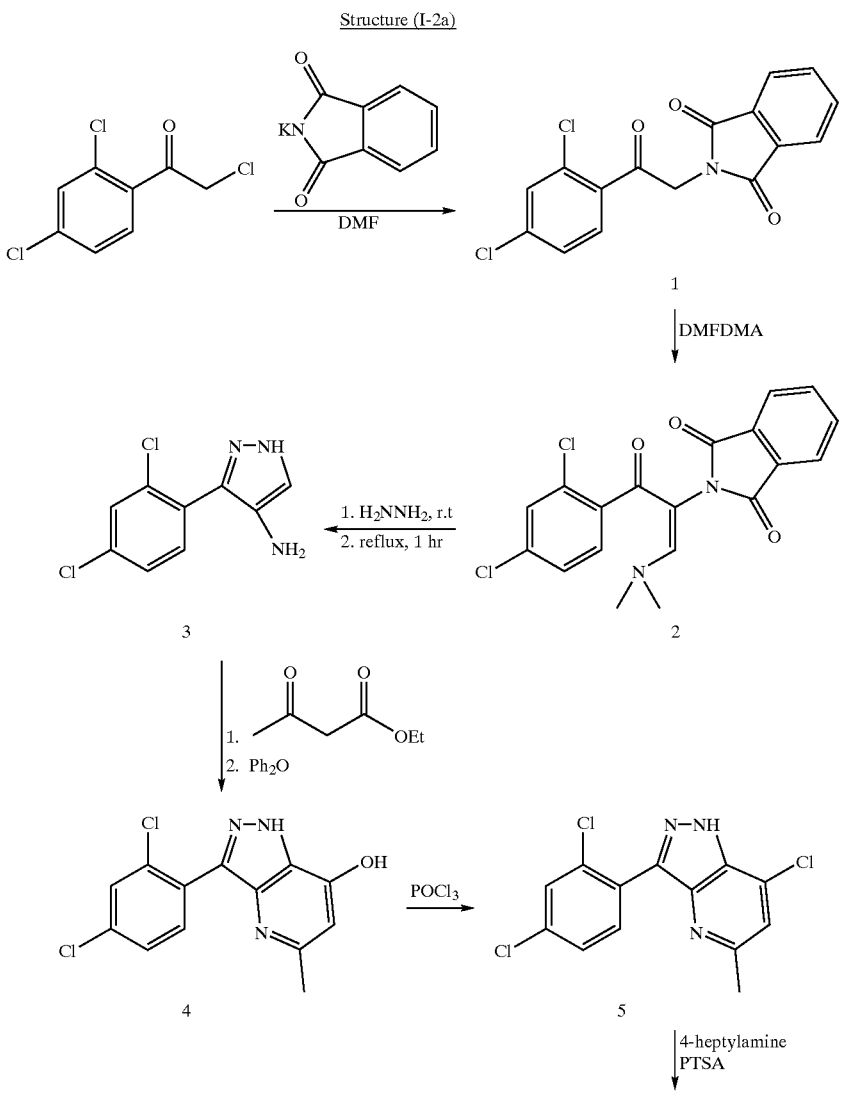

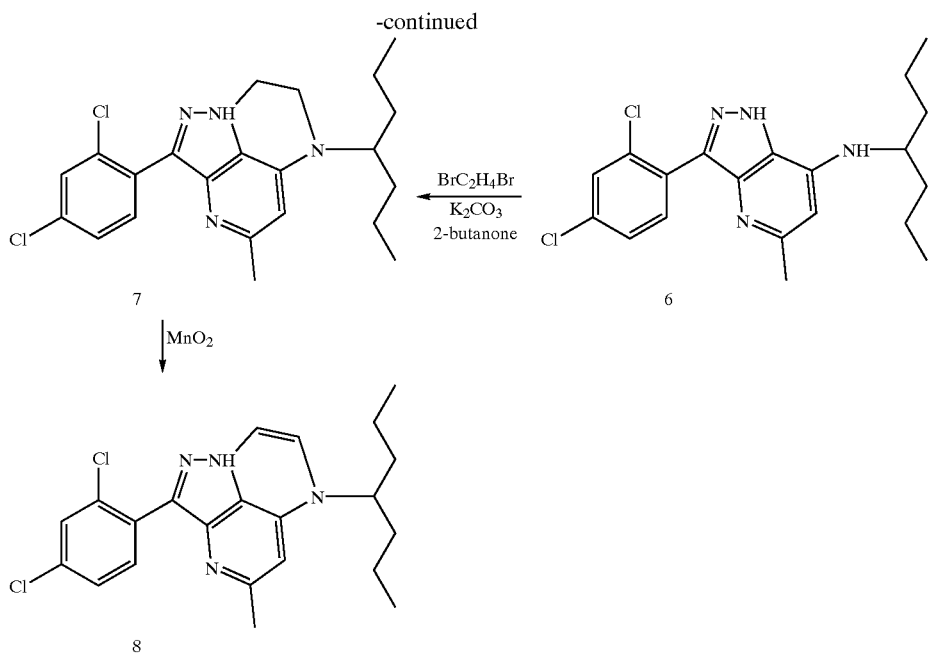

α-phthalimide-2,4-trichloroacetophenone (1)

α-2,4-trichloroacetophenone (15 gms, 67 mmol) was added with stirring to a suspension of potassium phtalimide (16 gms, 86 mmol) in N,N-dimethylformamide (70 ml) at 5° C. After 5 min., the resulting solution was allowed to warm to room temperature, followed by heating for 0.5 hr at 50° C. After heating the solution was concentrated on pump and the resulting solid was partitioned between ethyl acetate/sodium bicarbonate solution and the resulting organic layers were combined. These were dried and all solvent removed to yield solid. This solid was recrystallized from methylene chloride and ether to yield compound (1), 9.6 gms.
Compound (2)

A solution of α-phthalimide-2,4-trichloroacetophenone (1) (9.6 gms) in dimethylformamide dimethyl acetal (30 ml) and refluxed for 1 hour. After reflux, t.l.c. indicate the completion of the reaction and all solvent was removed on high vacuum to yield tan solid (2).

2-(2',4'-Dichlorophenyl)-3-aminopyrazole (3)

To a suspension of compound (2) (14 g, 36 mmol) in dry ethanol (300 mL) was added anhydrous hydrazine (1.2 g, 36 mmol). The tan suspension slowly turned into a clear dark brown solution. The solution was stirred at room temperature for 1 hr and more anhydrous hydrazine (1.2 g, 36 mmol) was added. The solution was heated to reflux for 2 hrs and a white solid formed. The reaction mixture was cooled to room temperature and the solid was filtered off. The filtrate was concentrated and partitioned between aqueous saturated sodium bicarbonate solution and ethyl acetate. The ethyl acetate layer was washed with Brine, dried -by sodium sulfate, filtered, and concentrated. The residue was purified by flash chromatography on silica gel to provide the desired product (3) as a brown sticky solid (7.7 g, 33.8 mmol, 94%), which was confirmed by GC/MS.

2-Methyl-4-Hydroxy-7-(2',4'-Dichlorophenyl)-pyrrozolepyridine (4)

A solution of compound (3) (7.7 g, 33.8 mmol), ethyl acetoacetate (8.4 g, 65 mmol) and 120 mg of p-tolunesulfonic acid monohydrate in 200 mL of benzene was refluxed for 2 hrs. The reaction mixture was concentrated and dissolved in 20 mL of diphenylether. The diphenylether was heated to 240° C. for 10 minutes, cooled and the solid was collected by filtration, and rinsed with diethyl ether. The product (4) was obtained as a brown solid (2.5 g, 8.4 mmol, 25%), which was confirmed by $^1$H NMR.

2-Methyl-4-Chloro-7-(2',4'-Dichlorophenyl)-pyrrozolepyridine (5)

A mixture of compound (4) (2.0 g, 6.8 mmol) and phosphorous oxychloride (10 mL) as refluxed for 2 hr, cooled, poured onto a crack ice, neutralized by 1N NaOH. The aqueous layer was extracted by ethyl acetate. The organic layer was washed with brine, dried under sodium sulfate, concentrated to yield a yellow solid which was triturated in ether. The desired product (5) was obtained as a pale yellow solid (1.1 g, 3.2 mmol, 47%), which was identified by GC/MS, Elemental Analysis and $^1$H NMR.

2-Methyl-4-(N-4-heptyl)-7-(2',4'-Dichlorophenyl)-pyrrozolepyridine (6)

A mixture of (5) (0.3 g, 0.96 mmol) and p-toluenesulfonic acid monohydrate (250 m g) in 0.8 mL of 4-heptylamine in a 5 mL Reacti-Vials was refluxed at 180° C. for 6 hours. The reaction mixture was cooled, partitioned between ethyl acetate and water. The organic layer was washed with Brine, dried under sodium sulfate, concentrated, purified by flash chromatography on silica gel (Hexane/EtOAc, 1:1) to provide the desired product (6) as a yellow oil (140 mg, 0.36 mmol, 37%), which was identified by GC/MS and $^1$H NMR.
Compound (7) (I-2a-1)

A mixture of 2-Methyl-4-(N-4-heptyl)-7-(2',4'-Dichlorophenyl)-pyrrozolepyridine (6) (43.9 mgs, 0.11 mmoles), potassium carbonate (31.0 mgs, 0.22 mmoles) and 1,2-dibromoethane in butanone (2 ml) was heated to 85° C. overnight. The solvent was removed in vacuum and the residue was partitioned between ethyl acetate and water, the organic layer was dried over magnesium sulfate, filtered and concentrated in vacuum. Compound (7) was purified by silica gel column eluting with dichloromethane-methanol (10-1), and identified by LC/MS. ¹H NMR (CDCl₃, TMS) :0.93 (t, 6H); 1.37 (m, 4H); 1.61 (m, 4H); 2.58 (5, 3H); 3.67 (t, 24); 3.82 (m, 1H); 4.45 (t, 2H); 6.22 (s, 1H); 7.35 (d, 1H); 7.53 (s, 1H); 7.86 (d, 1H).

Compound (8)

A solution of compound (7) (43 mg, 0.1 mmol) in toluene (2 ml) was treated with activated manganese dioxide catalyst (100 mg) at reflux for 16 hrs. The catalyst was removed by filtration through a Celite pad and the filtrate was evaporated to dryness and purified by Prepative TLC (silica gel) with ethyl acetate:hexane (1:1) to provide compound (8).

Alternatively, compounds of structure (I-2a) may be prepared by the following procedure.

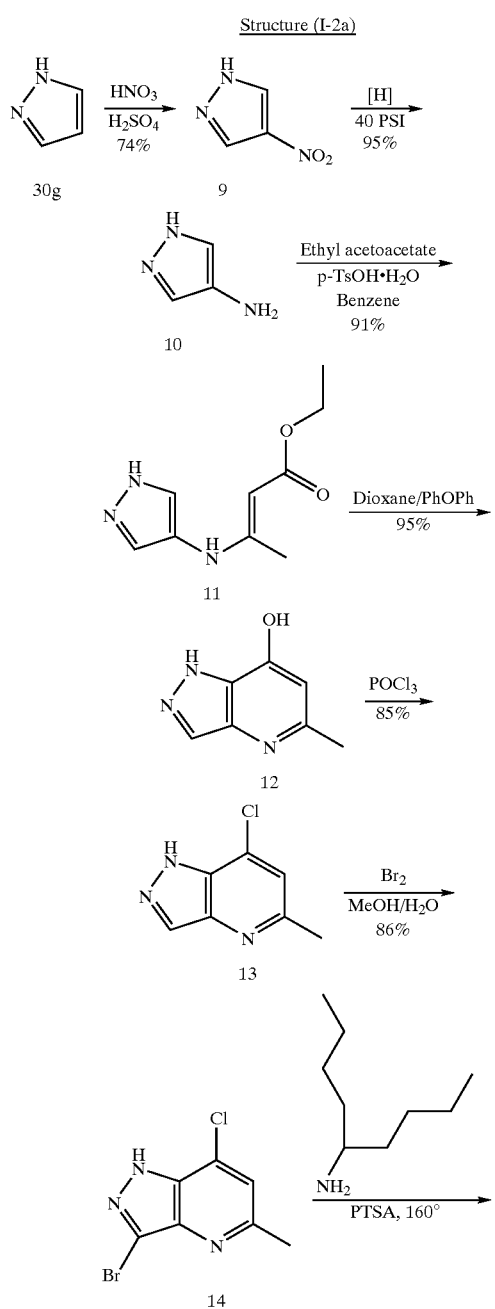

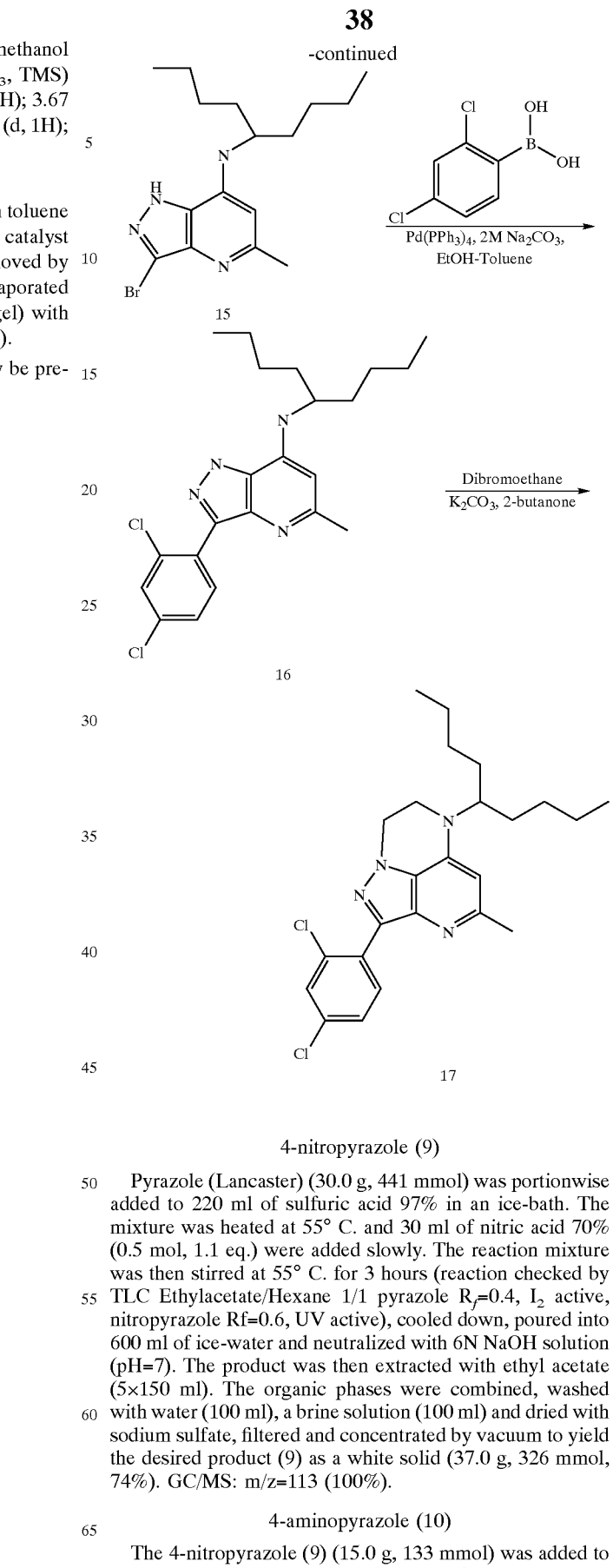

4-nitropyrazole (9)

Pyrazole (Lancaster) (30.0 g, 441 mmol) was portionwise added to 220 ml of sulfuric acid 97% in an ice-bath. The mixture was heated at 55° C. and 30 ml of nitric acid 70% (0.5 mol, 1.1 eq.) were added slowly. The reaction mixture was then stirred at 55° C. for 3 hours (reaction checked by TLC Ethylacetate/Hexane 1/1 pyrazole R$_f$=0.4, I₂ active, nitropyrazole Rf=0.6, UV active), cooled down, poured into 600 ml of ice-water and neutralized with 6N NaOH solution (pH=7). The product was then extracted with ethyl acetate (5×150 ml). The organic phases were combined, washed with water (100 ml), a brine solution (100 ml) and dried with sodium sulfate, filtered and concentrated by vacuum to yield the desired product (9) as a white solid (37.0 g, 326 mmol, 74%). GC/MS: m/z=113 (100%).

4-aminopyrazole (10)

The 4-nitropyrazole (9) (15.0 g, 133 mmol) was added to a suspension of palladium on carbon 10% (7.0 g, 6.65 mmol, 5% mmol) in ethanol (100 ml). The mixture was shaken for 3 hours under hydrogen pressure (40 psi) at room temperature. The end of reaction checked by TLC (Ethylacetate/Hexane 1/1, 4-nitropyrazole $R_f$=0.6, UV active, 4-aminopyrazole $R_f$ 0.1, UV active). The catalyst was removed by filtration through a pad of Celite and the solvent was evaporated. The product (10) was obtained as a burgundy oil (10.5 g, 126 mmol, 95%), which was used in the following step without purification. GC/MS: m/z=83 (100%).

Imine (11).

A solution of 4-aminopyrazole (10) (10.5 g, 126 mmol), ethylacetoacetate (18.0 g, 140 mmol, 1.05 eq.) and a catalytic amount of para-toluenesulfonic acid monohydrate (1.3 g, 6.65 mmol, 5%) in 100 mL of benzene was refluxed with a Dean-Stark trap for about 1 hour. The end of reaction checked by TLC (Ethylacetate/Hexane 1/1, 4-aminopyrazole $R_f$=0.1, imine $R_f$=0.5, UV active, brown after overnight). Solvents were removed under vacuum and the imine was purified by running through a short silica chromatography column to give the desired product (11) as a tan solid (22.4 g, 125 mmol, 91%). GC/MS: m/z=195 (100%).

5-Methyl-7-hydroxy-pyrazolo[4,3-b]pyridine (12)

The imine (11) (7.03 g, 35.9 mmol) was added to a boiling solution of dioxane (30 mL) and diphenyl ether (30 mL). The mixture was heated until solid formed (5 min). The reaction mixture was continued heating for 2 more minutes. Heating was stopped. The end of the cylcization was checked by LC/MS (disappearance of 196). After cooling down at room temperature, 300 ml of diethyl ether were added the reaction mixture was stirred for 15 minutes. The solid was rinsed with diethyl ether. The desire product (12) was obtained as a tan crystalline solid (5.09 g, 34.1 mmol, 95%). LC/MS: [M+H]'=150.

5-Methyl-7-chloro-pyrazolo[4,3-b]pyridine (13)

The cyclized compound (12) (4.58 g, 30.7 mmol) in phosphorus oxychloride (30 mL) was heated at 110° C. for 30 minutes. The end of the reaction was checked by LC/MS (disappearance of 150, appearance of 168). After cooling down at room temperature, the reaction mixture was poured on ice and pH was adjusted with a 6N NaOH solution to pH=5. The solid was collected with filtration and the mother aqueous layer was extracted with ethyl acetate (3×250 ml). The above solid was dissovled in the combined organic phases, washed with a brine solution (1×250 ml) and dried with sodium sulfate, filtered and concentrated. The crude product was purified by running through a short silica gel chromatography column to give the desired product (13) as a pale yellow solid (4.50 g, 26.8 mmol, 87%). GC/MS: m/z=167 (100%);. LC/MS: [M+H]'=168.

3-Bromo-5-methyl-7-chloro-pyrazolo[4,3-b]pyridine (14)

The chloro compound (13) (600 mg, 3.58 mmol) was dissolved in a mixture of water/methanol (12 mL/12mL) in an ice-bath. A solution of bromine (629 mg, 3.94 mmol, 1.1 eq.) in a solution of $H_2O$/MeOH 1 mL/1 mL) was added dropwise to the cooled mixture. After 10 minutes, the solution was clearer and the LC/Ms showed no more chloro compound. The reaction mixture was concentrated to remove the MeOH. The crude reaction mixture was extracted with ethyl acetate (3×50 ml). The organic phases were combined, washed with a brine solution (1×100 ml) and dried with sodium sulfate, filtered and concentrated by vacuum. The desired product (14) was obtained as a pale yellow solid. GC/MS: m/z=245, 247 (100%); LC/MS: [M+H]'=246, 248.

3-Bromo-5-methyl-7-(5-aminononane)-pyrazolo[4,3b]pyridine (15)

Compound (14) (1.0 g; 0.4 mmol) and 5-aminononane (1.7 g; 12 mmol) and p-toluenesulfonic acid (1.5 g, 8 mmol) were heated in reaction vial at 160° C. over night. The residue was dissolved in ethyl acetate, washed with saturated solution of sodium bicarbonate, brine, dried with MgSO4 and concentrated in vacuum. The residue was triturated with toluene and the solid formed was isolated and dried in vacuum to give 912 mg of product (15) as a white solid. LCMS: (M+H)=353, 354.

3-(2,4-dichlorophenyl)-5-methyl-7-(5-aminononane)-pyrazolo[4,3b]pyridine (16)

A mixture of compound (15) (100 mg, 0.27 mmol), 2,4-dichlorophenylboronic acid (63.7 mg), ethanol (0.6 ml), 2M solution of sodium carbonate (0.6 ml), Pd(PPh$_3$)$_4$ (10 mg) and toluene (1.6 ml) was heated at 160° C. over night. The solution was partitioned between EtOAc and water. The organic layer was dried with MgSO$_4$ and concentrated in vacuum. The residue was purified by chromatography on silica gel to give 34 mg of product (16). LCMS (M+H)=419, 420.

Compound (17) (I-2a-2)

To compound (16) (34 mg, 0.08 mmol) in 2-butanone (3 ml) was added potassium carbonate (67.18 mg, 0.48 mmol) and dibromoethane (30.48 mg, 0.16 mmol) and the mixture was heated at reflux over night. The mixture was partitioned between ethyl acetate and water. The organic layer was dried with magnesium sulfate and concentrated in vacuum. The crude product was purified by chromatography on silica gel eluting with ethyl acetate-hexane (1-1) to give 10 mg of product (17) (referred in Table 2 below as "Cpd. No. (I-2a-1)". LC/MS (M+H)=445, 446

Further representative compounds of this invention were prepared by the procedures set forth in the above examples, the analytical data for which are set forth in the following Table 1.

TABLE 1
Analytical Data for Representative Compounds
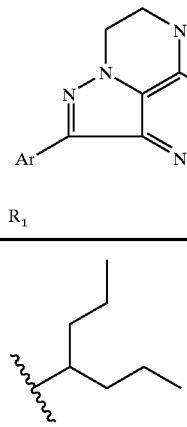
| Cpd. No. | Ar | R₁ | Analytical Data |
|---|---|---|---|
| (I-2a-1) | 2,4-dichlorophenyl | 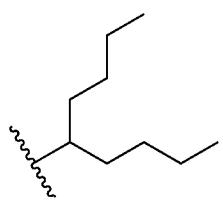 | 0.93 (t, 6H); 1.37 (m, 4H); 1.61 (m, 4H); 2.58 (5, 3H); 3.67 (t, 24); 3.82 (m, 1H); 4.45 (t, 2H); 6.22 (s, 1H); 7.35 (d, 1H); 7.53 (s, 1H); 7.86 (d, 1H). |
| (I-2a-2) | 2,4-dichlorophenyl | 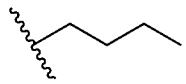 | LC/MS (M + H) = 445, 446 |
| (1-2a-3) | 2,4-dichlorophenyl | 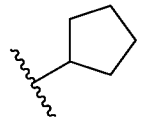 | LC/MS (M + H) = 376 |
| (I-2a-4) | 2,4-dichlorophenyl | 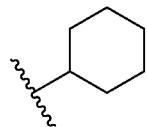 | LC/MS (M + H) = 387 |
| (I-2a-5) | 2,4-dichlorophenyl | 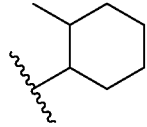 | LC/MS (M + H) = 401 |
| (I-2a-6) | 2,4-dichlorophenyl | 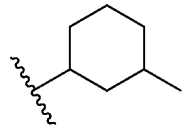 | LC/MS (M + H) = 415 |
| (I-2a-7) | 2,4-dichlorophenyl | 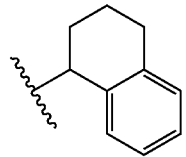 | LC/MS (M + H) = 415 |
| (I-2a-8) | 2,4-dichlorophenyl |  | LC/MS (M + H) = 449 |

TABLE 1-continued

Analytical Data for Representative Compounds

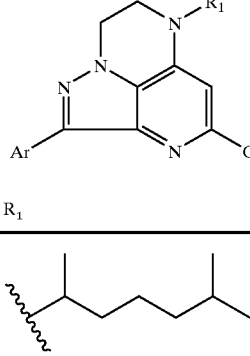

| Cpd. No. | Ar | R₁ | Analytical Data |
|---|---|---|---|
| (I-2a-9) | 2,4-dichlorophenyl | 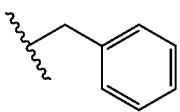 | LC/MS (M + H) = 431 |
| (I-2a-10) | 2,4-dichlorophenyl | 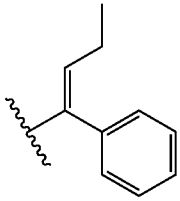 | LC/MS (M$^+$ + 1) = 409 |
| (I-2a-11) | 2,4-dichlorophenyl | 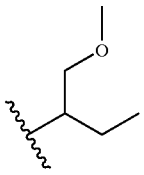 | 7.87 (d, J=8.4 Hz, 1 H), 7.54 (d, J=2.1 Hz, 1 H), 7.42-7.29 (m, 6 H), 6.29 (s, 1 H), 5.83 (t, J=7.7 Hz, 1 H) 4.51 (dd, J=5.7, 5.1 Hz, 2 H), 3.86 (dd, J=5.4, 4.8 Hz, 2 H), 2.51 (s, 3 H), 2.41-2.31 (m, 2 H), 1.14 (t, J=7.7 Hz, 3 H); LCMS (M$^+$ + 1) = 449. |
| (I-2a-12) | 2,4-dichlorophenyl | 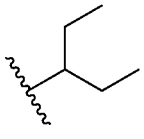 | LC/MS 405 (MH+) |
| (I-2a-13) | 2,4-dichlorophenyl | 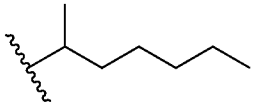 | LC/MS (MH+) = 390 |
| (I-2a-14) | 2,4-dichlorophenyl | 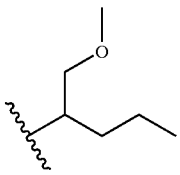 | LC/MS (MH+) = 418 |
| (I-2a-15) | 2,4-dichlorophenyl | 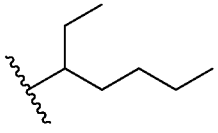 | LC/MS (MH+ = 419 |
| (I-2a-16) | 2,4-dichlorophenyl |  | LC/MS 417 (MH+) |

TABLE 1-continued
Analytical Data for Representative Compounds
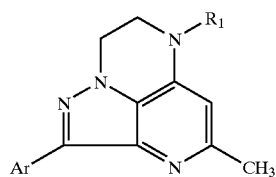
| Cpd. No. | Ar | R₁ | Analytical Data |
|---|---|---|---|
| (I-2a-17) | 2-chloro-4-methylphenyl | | LC/MS (MH+) = 397 |
| (I-2a-18) | 2-chloro-4-methylphenyl | | LC/MS (MH+) = 397 |
| (I-2a-19) | 2-chloro-4-methoxyphenyl | | LC/MS (MR+) = 413 |
| (I-2a-20) | 2-chloro-4-methylphenyl | | LC/MS (MH+) = 385 |

Alternatively, compounds of structure (I-2b) may be made by the following reaction scheme:

Structure (I-2b)

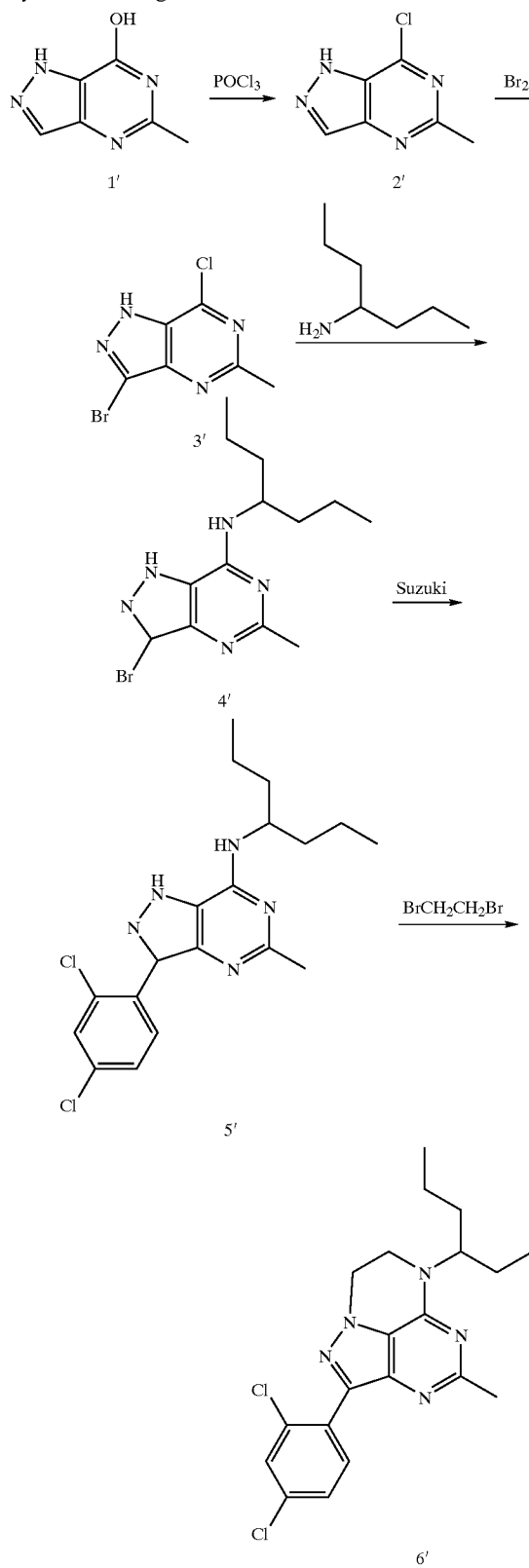

Compound (2')
A mixture of (1') (4.50 g, 30 mmol)(T. Huynh-Dinh et al., *J. Org. Chem.* 40: 2825–2830, 1975) and phosphorous oxychloride (15 mL) was refluxed for 3 hrs, cooled, poured onto a crack ice, neutralized by 1N NaOH. The aqueous layer was extracted by ethyl acetate. The organic layer was washed with brine, dried under sodium sulfate, concentrated to yield the desired product (2').

Compound (3')
To a mixture of (2') (3.37 g, 20 mmol) in methanol (20 mL) and water (20 mL) was added bromine (3.84 g, 24 mmol) in methanol (10 mL) and water (10 mL). The reaction mixture was stirred at room temperature for 2 hrs. The reaction mixture was washed with sodium thiosulfate aqueous solution, extracted with ethyl acetate. The residue was purified by flash chromatography on silica gel to provide the desired product (3').

Compound (4')
A mixture of (3') (2.50 g, 10 mmol) and p-toluenesulfonic acid monohydrate (100 mg) in 3 mL of 4-heptylamine was refluxed by 120° C. for 5 hours. The reaction mixture was cooled, partitioned between ethyl acetate and sodium bicarbonate aqueous solution. The organic layer was washed with brine, dried under sodium sulfate, concentrated, purified by flash chromatography on silica gel to provide the desired product (4').

Compound (5')
To a stirring solution of (4') (1.63 g, 5 mmol) in 10 mL of toluene was added tetrakis(triphenylphosphine)-(palladium (0) (578 mg, 0.5 mmol, 10% mol) and 2.0M aqueous sodium carbonate solution (8 mL) followed by addition of 2,4-dichloro-benzeneboronic acid (1.14 g, 6 mmol) in ethyl alcohol (8 mL). The resulting mixture was refluxed under nitrogen overnight. The reaction mixture was cooled, diluted with ethyl acetate and washed with saturated ammonium chloride solution once. The organic layer was dried by sodium sulfate, filtered, concentrated. The residue was purified by flash chromatography on silica gel to provide the desired product (5').

Compound (6')
A mixture of (5') (390 mg, 1 mmol), 1,2-dibromoethane (1 mL) and potassium carbonate (276 mg, 2 mmol) in 10 ML 2-butanol was refluxed for 4 hours. The reaction mixture was cooled, partitioned between ethyl acetate and sodium bicarbonate aqueous solution. The organic layer was washed with brine, dried under sodium sulfate, concentrated, purified by flash chromatography on silica gel to provide the desired product (6').

Example 3

Synthesis of Representative Compounds of Structure (I-3)

Structure (I-3a)

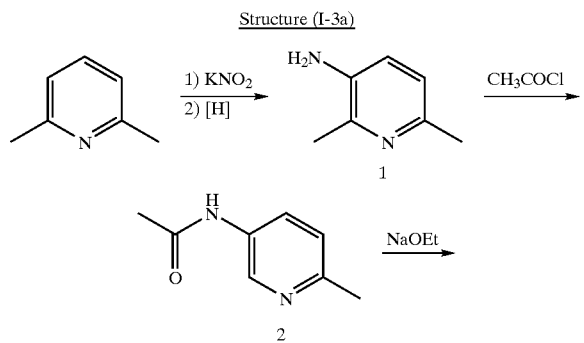

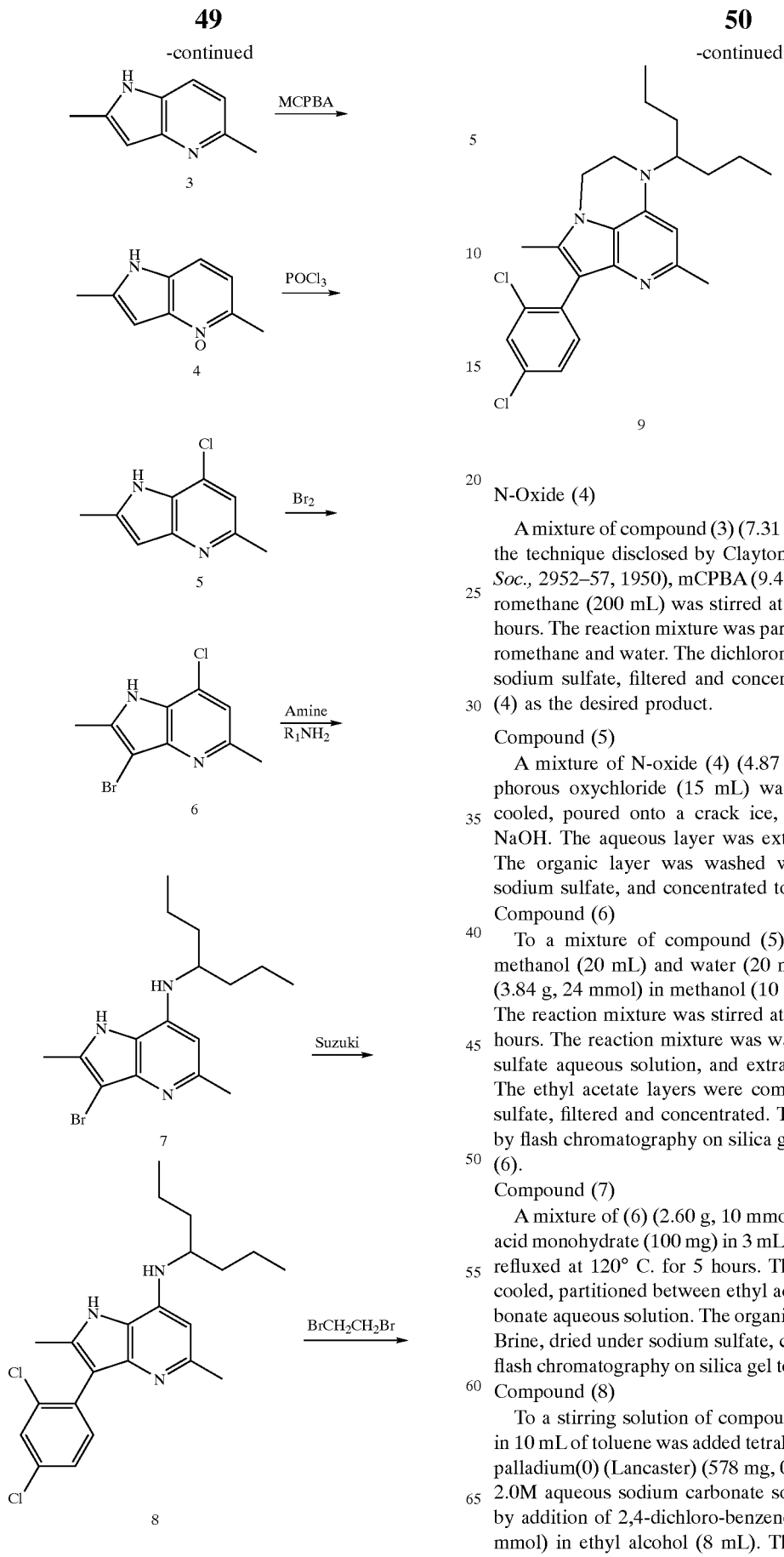

N-Oxide (4)

A mixture of compound (3) (7.31 g, 50 mmol) prepared by the technique disclosed by Clayton and Kenyon (*J. Chem. Soc.*, 2952–57, 1950), mCPBA (9.49 g, 55 mmol) in dichloromethane (200 mL) was stirred at room temperature for 2 hours. The reaction mixture was partitioned between dichloromethane and water. The dichloromethane was dried under sodium sulfate, filtered and concentrated to yield N-oxide (4) as the desired product.

Compound (5)

A mixture of N-oxide (4) (4.87 g, 30 mmol) and phosphorous oxychloride (15 mL) was refluxed for 3 hours, cooled, poured onto a crack ice, and neutralized by 1N NaOH. The aqueous layer was extracted by ethyl acetate. The organic layer was washed with brine, dried under sodium sulfate, and concentrated to yield compound (5).

Compound (6)

To a mixture of compound (5) (3.61 g, 20 mmol) in methanol (20 mL) and water (20 mL) was added bromine (3.84 g, 24 mmol) in methanol (10 mL) and water (10 mL). The reaction mixture was stirred at room temperature for 2 hours. The reaction mixture was washed with sodium thiosulfate aqueous solution, and extracted with ethyl acetate. The ethyl acetate layers were combined, dried by sodium sulfate, filtered and concentrated. The residue was purified by flash chromatography on silica gel to provide compound (6).

Compound (7)

A mixture of (6) (2.60 g, 10 mmol) and p-toluenesulfonic acid monohydrate (100 mg) in 3 mL of 4-amino-heptane was refluxed at 120° C. for 5 hours. The reaction mixture was cooled, partitioned between ethyl acetate and sodium bicarbonate aqueous solution. The organic layer was washed with Brine, dried under sodium sulfate, concentrated, purified by flash chromatography on silica gel to provide compound (7).

Compound (8)

To a stirring solution of compound (7) (1.69 g, 5 mmol) in 10 mL of toluene was added tetrakis(triphenylphosphine)-palladium(0) (Lancaster) (578 mg, 0.5 mmol, 10% mol) and 2.0M aqueous sodium carbonate solution (8 mL) followed by addition of 2,4-dichloro-benzeneboronic acid (1.14 g, 6 mmol) in ethyl alcohol (8 mL). The resulting tan mixture was refluxed overnight. The reaction mixture was cooled, diluted with ethyl acetate and washed with saturated ammonium chloride solution once. The organic layer was dried by sodium sulfate, filtered, concentrated. The residue was purified by flash chromatography on silica gel to provide compound (8).

Compound (9)

A mixture of compound (8) (404 mg, 1 mmol), 1,2-dibromoethane (1 ml) and potassium carbonate (276 mg, 2 mmol) in 10 mL 2-butanol was refluxed for 4 hours. The reaction mixture was cooled, partitioned between ethyl acetate and sodium bicarbonate aqueous solution. The organic layer was washed with Brine, dried under sodium sulfate, concentrated, purified by flash chromatography on silica gel to provide compound (9).

Alternatively, compounds of structure (I-3b) may be made by the following reaction scheme.

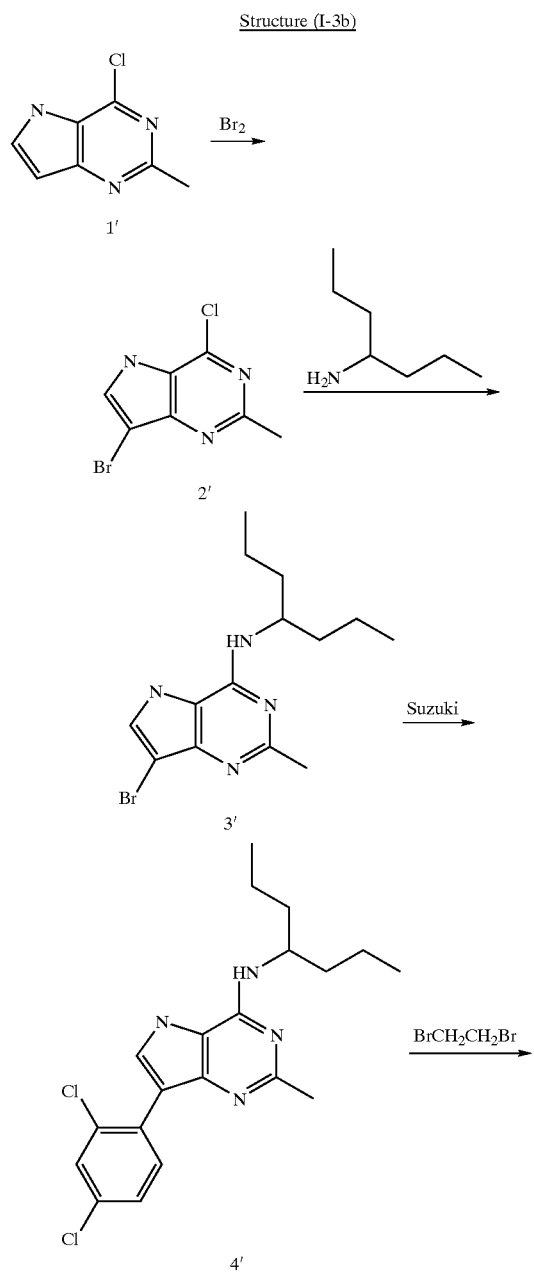

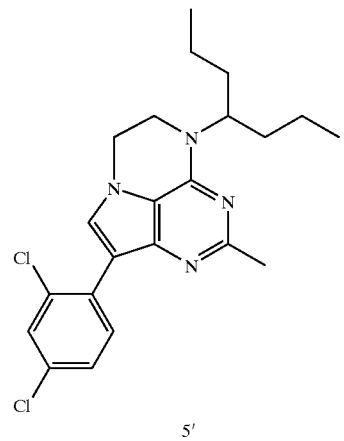

Compound (2')

To a mixture of (1')(Imai, *Chem Pharm. Bull.* 12:1030–1039, 1964) (3.34 g, 20 mmol) in methanol (20 mL) and water (20 mL) was added bromine (3.84 g, 24 mmol) in methanol (10 mL) and water (10 mL). The reaction mixture was stirred at room temperature for 2 hrs. The reaction mixture was washed with sodium thiosulfate aqueous solution, extracted with ethyl acetate. The ethyl acetate layers were combined, dried by sodium sulfate, filtered and concentrated. The residue was purified by flash chromatography on silica gel to provide the desired product (2').

Compound (3')

A mixture of (2') (2.48 g, 10 mmol) and p-toulenesulfonic acid monohydrate (100 mg) in 3 mL of 4-heptylamine was refluxed at 120° C. for 5 hours. The reaction mixture was cooled, partitioned between ethyl acetate and sodium bicarbonate aqueous solution. The organic layer was washed with brine, dried under sodium sulfate, concentrated, purified by flash chromatography on silica gel to provide the desired product (3').

Compound (4')

To a stirring solution of (3') (1.63 g, 5 mmol) in 10 mL of toluene was added tetrakis(triphenylphosphine)-(palladium (0) (578 mg, 0.5 mmol, 10% mol) and 2.0M aqueous sodium carbonate solution (8 mL) followed by addition of 2,4-dichloro-benzeneboronic acid (1.14 g, 6 mmol) in ethyl alcohol (8 mL). The resulting mixture was refluxed under nitrogen overnight. The reaction mixture was cooled, diluted with ethyl acetate and washed with saturated ammonium chloride solution once. The organic layer was dried by sodium sulfate, filtered, concentrated. The residue was purified by flash chromatography on silica gel to provide the desired product (4').

Compound (5')

A mixture of (4') (390 mg. 1 mmol), 1,2-dibromoethane (1 mL) and potassium carbonate (276 mg, 2 mmol) in 10 ML 2-butanol was refluxed for 4 hours. The reaction mixture was cooled, partitioned between ethyl acetate and sodium bicarbonate aqueous solution. The organic layer was washed with brine, dried under sodium sulfate, concentrated, purified by flash chromatography on silica gel to provide the desired product (5').

Example 4

Synthesis of Representative Compounds of Structure (I-4)

Structure (I-4b)

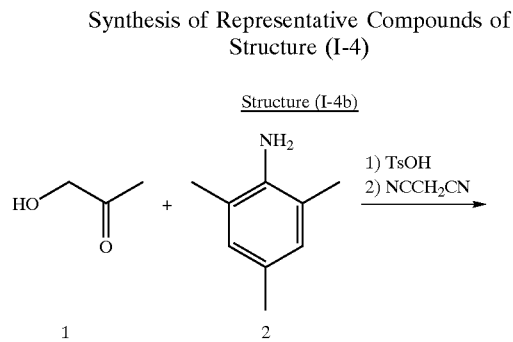

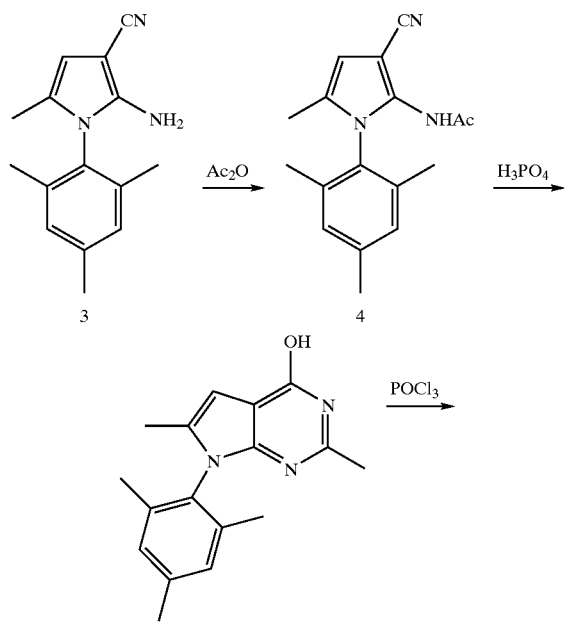

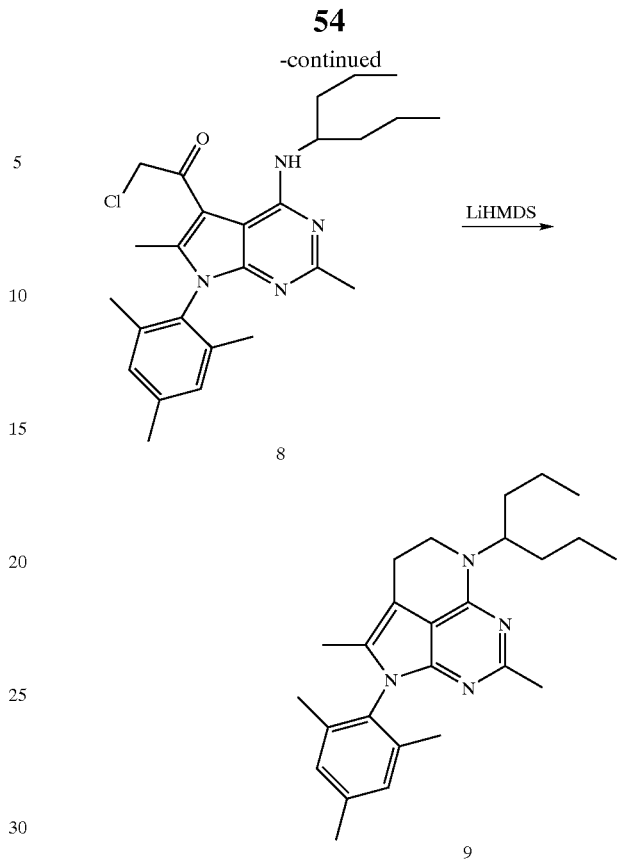

2-Amino-5-methyl-1-(2,4,6-trimethylphenyl)-1H-pyrrole-3-carbonitrile (3)

A solution of acetol (1) (20.0 mL, 0.260 mol), 2,4,6-trimethylaniline (2) (36.5 mL, 0.260 mol), and 4-toluenesulfonic acid monohydrate (0.20 g) were refluxed in benzene (115 mL) using a Dean-Stark trap to remove water. After 2 hours, malonitrile (16.4 mL, 0.260 mol) was added and heating was continued for 14 hours. The mixture was cooled to room temperature, concentrated, and the residue chromatographed (elution with 15% ethyl acetate in hexanes) to afford 27.0 g (43%) of compound (3) as a brown oil.

N-[3-Cyano-5-methyl-1-(2,4,6-trimethylphenyl)-1H-pyrrol-2-yl]acetamide (4)

A mixture of compound (3) (25.3 g, 0.106 mol) and acetic anhydride (11.0 mL, 0.117 mol) were refluxed in acetic acid (25 mL) for 45 minutes, cooled to room temperature, poured onto crushed ice and extracted with ethyl acetate. The organic layer was washed with aqueous sodium bicarbonate, dried, and concentrated to give 33.6 g (100%) of compound (4) as a yellow foam.

2,6-Dimethyl-7-(2,4,6-trimethylphenyl)-3,7-dihydro-pyrrol[2,3-d]pyrimidin-4-one (5)

A mixture of compound (4) (32.1 g, 0.144 mol) and 85% phosphoric acid (30 mL) was heated at 130° C. for 30 minutes. The resulting mixture was cooled to room temperature, poured into ice water with vigorous stirring, and the resulting precipitate was filtered and dried under vacuum to afford 21.6 g (67%) of compound (5) as a pink solid.

4-Chloro-2,6-dimethyl-7-(2,4,6-trimethylphenyl)-3,7-dihydro-pyrrol[2,3-d]pyrimidine (6)

A mixture of compound (5) (18.3 g, 65.0 mmol) in POCl3 (30 mL) was refluxed for 3 hours, cooled to room temperature, poured into ice water, and extracted with ethyl acetate. The combined organic extracts were washed with aqueous sodium bicarbonate, dried, and concentrated under vacuum. The residue was chromatographed (elution with 10% ethyl acetate in hexanes) to afford 16.3 g (84%) of compound (6) as a tan powder.

4-Chloro-2,6-dimethyl-7-(2,4,6-trimethylphenyl)-5-(2-chloroacetyl)-3,7-dihydropyrrolo[2,3-d]pyrimidine (7)

Compound (6) (11.2 g, 37.4 mmol) was added to a chloroform solution (150 ml) or 20 equivalents of aluminum chloride and 25 equivalents of chloracetyl chloride. The solution was heated at reflux for 16 hrs. The organic layer was departed and the water layer extracted with methylene chloride. The combined organic layers were dried over sodium sulfate and evaporated in vacuo to yield compound (7).

4-(4-heptylamino)-2,6-dimethyl-7-(2,4,6-trimethylphenyl)-5-(2-chloroacetyl)-3,7-dihydropyrrolo[2,3-d]pyrimidine (8)

A mixture of compound (7) (730 mg, 2 mmol), 4-aminoheptane (250 mg, 2.2 mmol) and triethylamine (250 mg, 2.5 mmol) were stirred at ambient temperature for 16 hours. The solution was diluted with ethyl acetate and washed with brine. The organic layer was dried over sodium sulfate and evaporated to dryness to provide compound (8).

Compound (9)

A solution of (8) (440 mg, 1 mmol) in THF (10 ml) was cooled to 0° C. and a 1M solution of lithium hexamethyldisilizane in THF (1 ml) was slowly added. The reaction was heated at reflux for 16 hrs, evaporated to dryness, and purified by flash chromatography with ethyl acetate and hexane to provide compound (9).

Alternatively, compounds of structured (I-4a) may be made by the following reaction scheme.

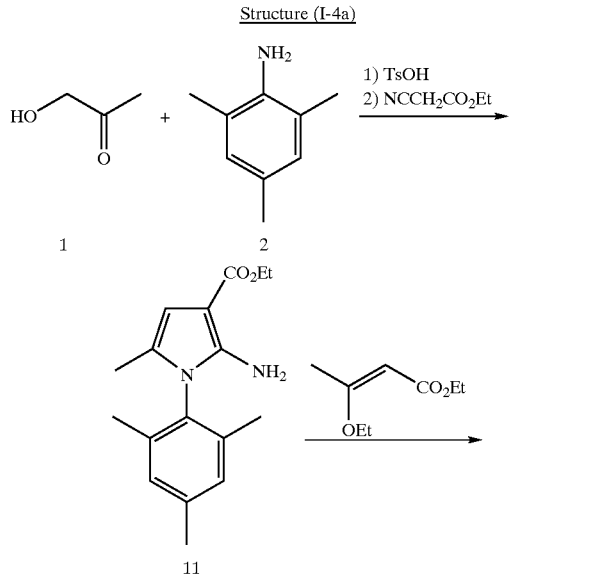

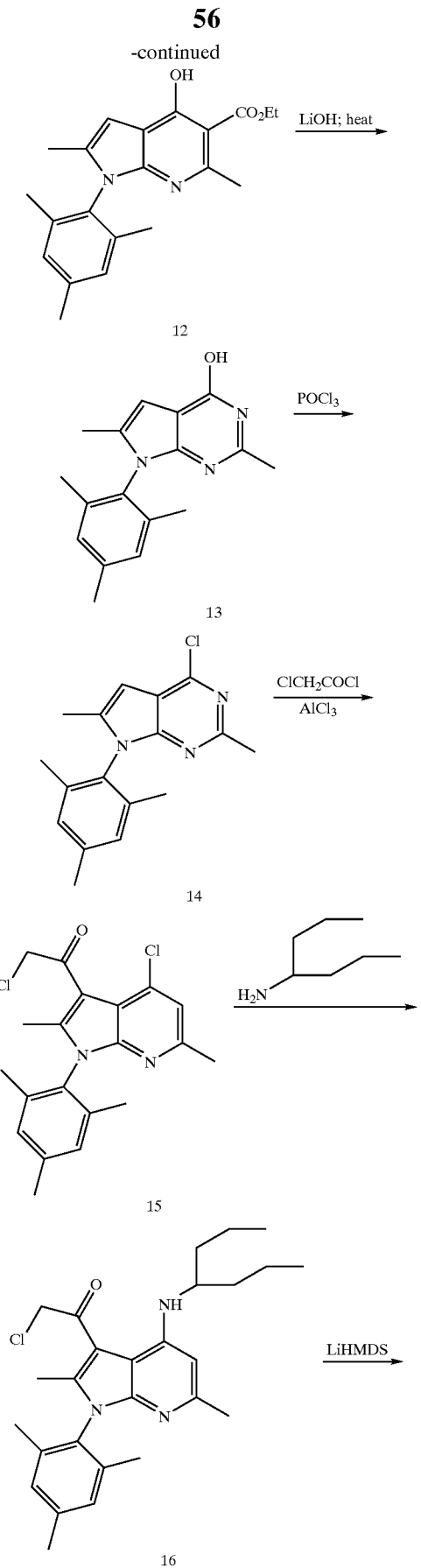

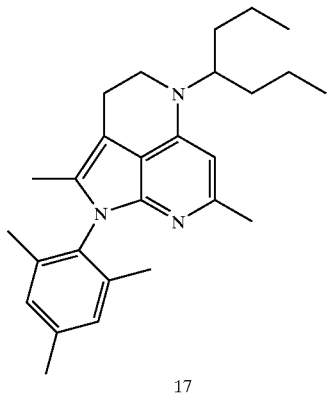

17

Ethyl 2-Amino-5-methyl-1-(2,4,6-trimethylphenyl)-1H-pyrrole-3-carboxylate (11)

A solution of acetol (1) (20 mL, 0.26 mol), 2,4,6-trimethylaniline (2) (36.5 mL, 0.260 mol), and 4-toluenesulfonic acid monohydrate (0.21 g) were refluxed in benzene (115 mL) using a Dean-Stark trap to remove water. After 2 hours, ethyl cyanoacetate (27.7 mL, 0.26 mol) was added and heating was continued for 14 hours. The mixture was cooled to room temperature, concentrated, and the residue chromatographed (elution with 15% ethyl acetate in hexanes) to afford 21.4 g (29%) of compound (11) as a yellow oil.

3-Carboethoxy-4-hydroxy-2,6-dimethyl-7-(2,4,6-trimethylphenyl)-1H-pyrrolo[2,3-b]pyridine (12)

A solution of compound (11) (12.3 g, 43.0 mmol), ethyl 3-ethoxycrotonate (6.79 g, 43.0 mmol) and 4-toluenesulfonic acid monohydrate (0.50 g) in xylene (100 mL) were refluxed for 30 minutes. The solvent was distilled off over an additional 30 minutes, and the mixture was cooled to room temperature. Potassium t-butoxide (4.82 g, 43.0 mmol) in absolute ethanol (50 mL) was added and the mixture was heated at 80° C. for 3 hours, cooled to room temperature, treated with acetic acid (2.50 mL) and concentrated under vacuum. The residue was taken up in ethyl acetate, and treated with diethyl ether to precipitate 6.91 g (46%) of compound (12) as a white powder.

4-Hydroxy-2,6-dimethyl-7-(2,4,6-trimethylphenyl)-1H-pyrrolo[2,3-b]pyridine (13)

Compound (12) (4.11 g, 11.7 mmol) in 1.0 M lithium hydroxide (25 mL) and ethanol (15 mL) was heated at reflux for 17 hours. The mixture was cooled to room temperature, neutralized with dilute aqueous hydrochloric acid, and extracted with ethyl acetate. The combined organic extracts were washed with aqueous sodium chloride, dried, and concentrated under vacuum. This material was heated at 200° C. for 2 hours in diphenyl ether (2.5 mL), cooled to room temperature, and crystallized from methanol-ethyl acetate to afford 1.41 g (43%) of compound (13) as a white powder.

4-Chloro-2,6-dimethyl-7-(2,4,6-trimethylphenyl)-1H-pyrrolo[2,3-b]pyridine (14)

Compound (14) was prepared from compound (13) according to the same procedure as above used in the preparation of compound (6).

4-Chloro-2,6-dimethyl-7-(2,4,6-trimethylphenyl)-5-(2-chloroacetyl)-1H-pyrrolo[2,3-b]pyridine (15)

Compound (15) was prepared from compound (14) according to the same procedure as disclosed above in the preparation of compound (7).

4-(4-heptylamino)-2,6-dimethyl-7-(2,4,6-trimethylphenyl)-5-(2-chloroacetyl)-1H-pyrrolo[2,3-b]pyridine (16)

Compound (16) was prepared from compound (15) according to the same procedure as disclosed above in the preparation of compound (8).

Compound 17

Compound (17) was prepared from compound (16) according to the same procedure as used above in the preparation of compound (9).

Compounds of structure (I-4b) may also be prepared according to the following reaction.

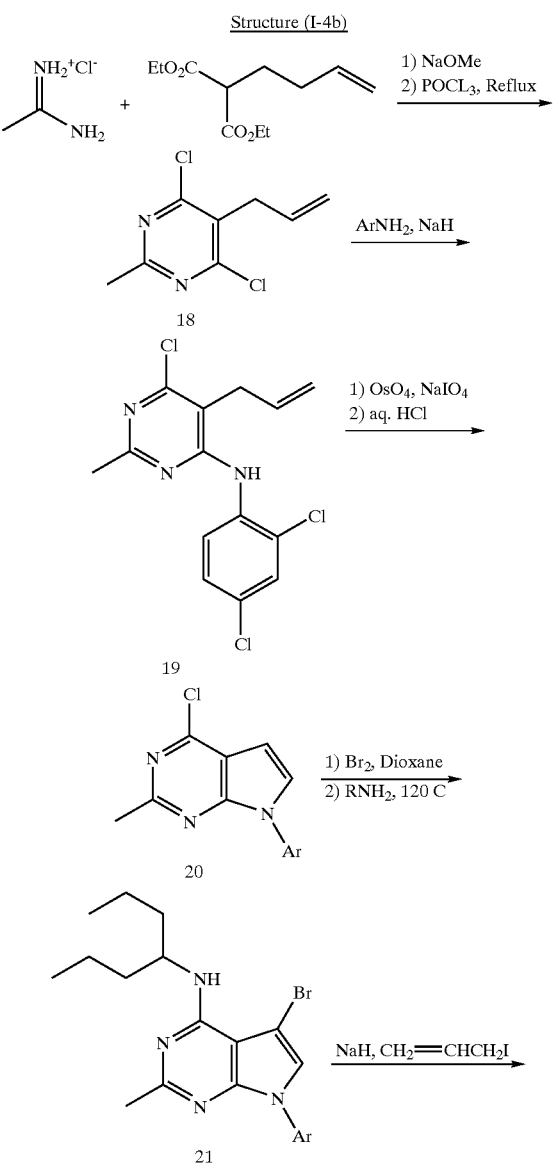

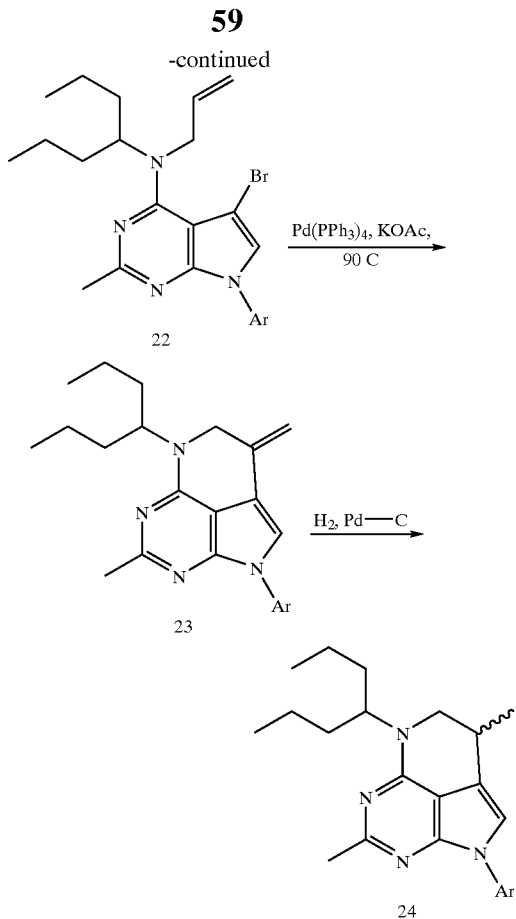

5-Allyl-4,6-dichloro-2-methylpyrimidine (18)

Acetamidine hydrochloride (11.2 g, 119 mmol) was added to a stirred solution of sodium methoxide (6.41 g, 119 mmol) in methanol (180 mL). After 5 min, diethyl allylmalonate (18 mL, 91 mmol) was added and the mixture was heated to reflux for 15 h, cooled to rt, and concentrated under vacuum to afford 20 g of the crude pyridinone as a white solid. This material was heated to reflux in phosphorus oxychloride (100 mL) for 5 h. The mixture was cooled to rt, poured over crushed ice (200 mL), neutralized with powdered NaHCO$_3$, and extracted with ethyl acetate. The combined extracts were dried (MgSO$_4$), concentrated in vacuo, and the residue was chromatographed (elution with 10% ethyl acetate in hexanes) to afford 7.32 g (30%) of pyrimidine (18) as a pale yellow oil.

5-Allyl-4-chloro-6-(2,4-dichloroanilino)-2-methylpyrimidine (19)

Sodium hydride mineral oil dispersion (60%, 1.38 g, 34.5 mmol) was added to a stirred solution of pyrimidine (18) (3.50 g, 17.2 mmol) and 2,4-dichloroaniline (3.07 g, 18.9 mmol) in DMF (40 ml,). After 25 min, the mixture was poured into water (100 mL) and extracted with dichloromethane. The combined extracts were dried (MgSO$_4$), concentrated under vacuum, and the residue was chromatographed (elution with dichloromethane) to afford 2.09 g (37%).of pyrimidine (19) as a white powder.

4-Chloro-1-(2,4-dichlorophenyl)-6-methyl-5,7-diazaindole (20).

Sodium periodate (3.83 g, 17.9 mmol) was added to a stirred solution of (19) (1.94 g, 5.90 mmol) in 3:1 acetone-water (55 mL). The mixture was heated briefly to obtain homogeneity, and a 2.5% solution of osmium tetroxide in t-butanol (0.4 mL) was added. After 20 h, the mixture was diluted with water (50 mL) and saturated sodium thiosulfate (50 mL), and extracted with ethyl acetate. The combined extracts were concentrated under vacuum, and the residue was stirred in dichloromethane (40 mL) and 4 N HCl (5 mL) for 4 h. The mixture was poured into saturated NaHCO$_3$, extracted with dichloromethane, dried (MgSO$_4$), and concentrated in vacuo. The residue was chromatographed (elution with dichloromethane) to afford 0.929 g (50%) of diazaindole (20) as a white solid.

3-Bromo-1-(2,4-dichlorophenyl)-4-(4-heptylamino)-6-methyl-5,7-diazaindole (21).

Bromine (0.077 mL, 1.5 mmol) was added to a stirred solution of (20) (214 mg, 0.685 mmol) in dioxane (21 mL). After 4 hours, the mixture was diluted with aqueous NaCl, and extracted with ethyl acetate. The combined extracts were dried (MgSO$_4$) and concentrated under vacuum to afford the crude bromide. This material was taken up 4-heptylamine (3 mL) and heated at 90° C. for 45 min. The resulting mixture was cooled to room temperature, concentrated under vacuum, and the residue was purified by preparative TLC (elution with 15% ethyl acetate in hexanes) to afford 227 mg (70%) of (21) as a yellow oil which solidified on standing.

N-Allyl-3-bromo-1-(2,4-dichlorophenyl)-4-(4-heptyl)amino-6-methyl-5,7-diazaindole (22).

Sodium hydride mineral oil dispersion (60%, 80 mg, 2.0 mmol) was added to a stirred solution of (21) (186 mg, 0.396 mmol) in DMF (5 mL). After 10 min, allyl iodide (0.15 mL, 1.6 mmol) was added, and stirring was continued for 90 min. The mixture was diluted with water and aqueous NaCl, and extracted with ethyl acetate. The combined extracts were dried (MgSO$_4$), concentrated under vacuum, and the residue was purified by preparative TLC (elution with 5% ethyl acetate in hexanes) to afford 117 mg (58%) of (22) as a white solid.

Compound (23) (I-4b-1)

Tetrakis(triphenylphosphine)palladium(0) (22 mg, 0.019 mmol) was added to a stirred solution of 5 (83 mg, 0.16 mmol) and potassium acetate (85 mg, 0.87 mmol) in DMF (3 ml), and the resulting mixture was heated at 83° C. for 45 min. The mixture was cooled to room temperature, poured into aqueous NaCl, and extracted with ethyl acetate. The combined extracts were concentrated under vacuum, and the residue was purified by preparative TLC (elution with 15% ethyl acetate in hexanes) to afford 59 mg (86%) of (23) as a colorless oil. $^1$H-NMR (300 MHz, CDCl$_3$) δ7.57 (d, J=2.4 Hz, 1 H), 7.49 (d, J=8.4 Hz, 1 H), 7.38 (dd, J=8.6, 2.3 Hz, 1 H), 6.98 (s, 1 H), 5.38 (br s, 1 H), 5.12 (br s, 1 H), 4.93 (h, J=5.0 Hz, 1 H), 4.03 (br s, 2 H), 2.54 (s, 3 H), 1.71–1.48 (m, 4 H), 1.38–1.26 (m, 4 H), 0.92 (t, J=7.4 Hz, 6 H); LCMS (MH$^+$, 429).

Compound (24) (I-4b-2)

Olefin (23) (9.4 mg, 0.022 mmol) and 10% palladium on activated charcoal (3 mg) were stirred in ethyl acetate (2 mL) under a balloon of hydrogen for 5 h. The mixture was filtered through a plug of Celite, concentrated under vacuum, and the residue was purified by preparative TLC (elution with 15% ethyl acetate in hexanes) to afford 4.9 mg (52%) of (24) as a colorless oil: $^1$H-NMR (300 MHz, CDCl$_3$) δ7.55 (d, J=2.7 Hz, 1 H), 7.48 (d, J=8.4 Hz, 1 H), 7.36 (dd, J=8.7, 2.7 Hz, 1 H), 6.63 (br s, 1 H), 4.85 (h, J=4.9

Hz, 1 H), 3.43 (dd, J=12.3, 4.8 Hz, 1 H), 3.23–3.19 (m, 1 H), 3.22 (dd, J=12.0, 9.6 Hz, 1 H), 2.54 (s, 3 H), 1.68–1.43 (m, 4 H), 1.39–1.25 (m, 7 H), 0.95–0.89 (m, 6 H); LCMS (MH+, 431).

Example 5

Synthesis of Further Representative Compounds of Structure (I-2A)

Additional representative compounds of this invention were made by the following reaction scheme.

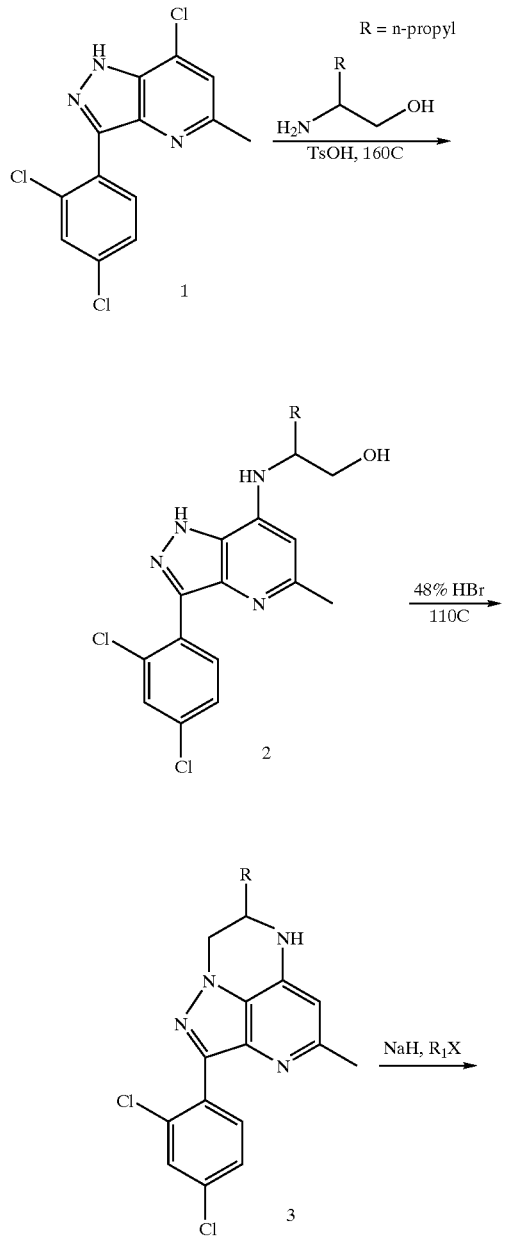

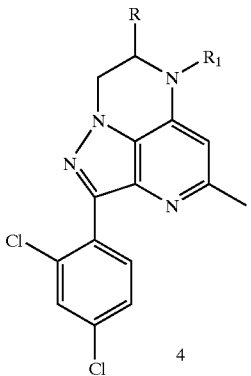

Compound (2)

Compound (1) (270 mg, 0.86 mmol), p-toluenesulfonic acid monohydrate (225 mg, 1.18 mmol) and DL-2-amino-1-pentanol (1 mL) were heated at 160° C. for 3 hours. The mixture was cooled to room temperature, diluted with dichloromethane, and purified on a silica gel column (elution with 10% methanol in dichloromethane) to afford 408 mg (100%) of compound (2) as a yellow solid: $^1$H NMR (300 MHz, CDCl$_3$) δ7.76 (d, J=4.8 Hz. 1H), 7.53 (br s, 1H), 7.24–7.12 (m, 2H), 7.20 (d, J=7.8 Hz, 1H), 6.12 (s, 1H), 3.76–3.67 (m, 3H), 2.49 (s, 3H), 1.63–1.56 (m, 2H), 1.45–1.32 (m, 3H), 0.89 (t, J=7.1 Hz, 3H); LC/MS (MH+, 379).

Compound (3)

Compound (2) (478 mg, 0.86 mmol) was dissolved in 48% HBr (5 mL) and heated at 110° C. for 4 days. The mix was cooled to room temperature, cautiously basified with solid NaOH, and extracted with ethyl acetate. The combined extracts were dried (MgSO$_4$) and concentrated under vacuum to afford 159 mg (51%) of compound (3) as a yellow foam: $^1$H NMR (300 MHz, CDCl$_3$) δ7.86 (d, J=8.4 Hz. 1H), 7.52 (d, J=2.1 Hz, 1H), 7.34 (dd, J=8.1, 2.1 Hz, 1H), 6.30 (s, 1H), 4.69 (br s, 1H), 4.60 (dd, J=12.0, 3.6 Hz, 1H), 4.10 (dd, J=12.2, 8.6 Hz, 1H), 3.88–3.85 (m, 1H), 2.58 (s, 3H), 1.78–1.55 (m, 4H), 1.05 (t, J=7.4 Hz, 3H); LC/MS (MH+, 361).

Compound (4)

Sodium hydride mineral oil dispersion (60%, 10 mg, 0.25 mmol) was added to a stirred solution of compound (3) (16 mg, 0.044 mmol) in DMF (0.5 mL). After 5 min, 1-bromopropane (0.050 mL, 0.55 mmol) was added and stirring was continued for 10 minutes. The mixture was cautiously diluted with saturated sodium bicarbonate, and extracted with ethyl acetate. The combined extracts were concentrated under vacuum, and the residue was purified by preparative TLC (elution with 10% methanol in dichloromethane) to afford 7 mg (40%) of compound (4) where R$_1$ is n-propyl as a yellow oil.

This technique is representative of the synthesis of the compounds presented in Table 2.

TABLE 2

Analytical Data for Representative Compounds

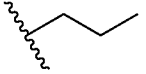

| Cpd. No. | R | R₁ | Analytical Data |
|---|---|---|---|
| (I-2a-21) | n-propyl | 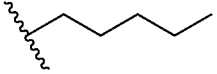 | 7.91 (d, J=8.4 Hz, 1 H), 7.53 (d, J= 2.1 Hz, 1 H), 7.35 (dd, J=8.4, 2.1 Hz, 1 H), 6.14 (s, 1 H), 4.52 (dd, J=12.2, 1.2 Hz, 1 H), 4.34 (dd, J=12.3, 3.9 Hz, 1 H), 3.80-3.74 (m, 1 H), 3.63-3.54 (m, 1 H), 3.21-3.11 (m, 1 H), 2.59 (s, 3 H), 1.86-1.60 (m, 4 H), 1.56-1.34 (m, 2 H), 1.01 (t, J=7.4 Hz, 3 H), 0.94 (t, J=7.2 Hz, 3 H); LCMS (MH+, 403) |
| (I-2a-22) | n-propyl | 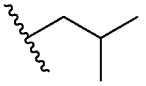 | 7.91 (d, J=8.4 Hz, 1 H), 7.53 (d, J= 2.1 Hz, 1 H), 7.36 (dd, J=8.4, 2.1 Hz, 1 H), 6.13 (s, 1 H), 4.52 (dd, J=12.2, 2.0 Hz, 1 H), 4.33 (dd, J=12.3, 4.2 Hz, 1 H), 3.80-3.74 (m, 1 H), 3.65-3.56 (m, 1 H), 3.23-3.14 (m, 1 H), 2.59 (s, 3 H), 1.80-1.60 (m, 5 H), 1.55-1.34 (m, 5 H), 0.97-0.91 (m, 6 H); LCMS (MH+, 431). |
| (I-2a-23) | n-propyl | 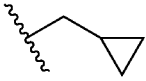 | 7.91 (d, J=8.4 Hz, 1 H), 7.54 (d, J= 2.4 Hz, 1 H), 7.36 (dd, J=8.4, 2.1 Hz, 1 H), 6.11 (s, 1 H), 4.54 (dd, J=12.5, 1.4 Hz, 1 H), 4.37 (dd, J=12.5, 4.1 Hz, 1 H), 3.76-3.70 (m, 1 H). 3.48 (dd, J= 14.4, 6.3 Hz, 1 H), 2.90 (dd, J=14.1, 8.7 Hz, 1 H), 2.59 (s, 3 H), 2.13-2.04 (m, 1 H), 2.0-1.25 (m, 4 H), 1.01 (d, J= 6.3 Hz, 3 H), 0.99 (d, J=6.9 Hz, 3 H), 0.93 (t, J=7.2 Hz, 3 H); LCMS (MH+, 417) |
| (I-2a-24) | n-propyl | 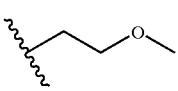 | 7.91 (d, J=8.4 Hz, 1 H), 7.53 (d, J= 2.1 Hz, 1 H), 7.35 (dd, J=8.3, 2.0 Hz, 1 H), 6.18 (s, 1 H), 4.56 (dd, J=12.6, 1.8 Hz, 1 H), 4.36 (dd, J=12.5, 4.1 Hz, 1 H), 4.02-3.96 (m, 1 H), 3.57 (dd, J= 14.4, 6.0 Hz, 1 H), 3.05 (dd, J=14.6, 7.4 Hz, 1 H), 2.59 (s, 3 H), 1.86-1.34 (m, 4 H), 1.13-1.09 (m, 1 H), 0.94 (t, J= 7.2 Hz, 3 H), 0.70-.61 (m, 2 H), 0.37-0.27 (m, 2 H); LCMS (MH+, 415) |
| (I-2a-25) | n-propyl |  | 7.90 (d, J=8.1 Hz, 1 H), 7.54 (d, J= 2.4 Hz, 1 H), 7.36 (dd, J=8.4, 2.1 Hz, 1 H), 6.15 (s, 1 H), 4.50 (dd, J=12.2, 1.7 Hz, 1 H), 4.34 (dd, J=12.2, 4.1 Hz, 1 H), 3.92-3.88 (m, 1 H), 3.78-3.72 (m, 1 H), 3.64-3.60 (m, 2 H), 3.51-3.42 (m, H), 3.37 (s, 3 H), 2.59 (s, 3 H), 1.69-1.25 (m, 4 H), 0.94 (t, J=7.4 Hz, 3 H); LCMS (MH+, 419). 7.90 (d, J=8.1 Hz, 1 H), 7.54 (d, J=2.4 Hz, 1 H), 7.36 (dd, J=8.4, 2.1 Hz, 1 H), 6.15 (s, 1 H), 4.50 (dd, J=12.2, 1.7 Hz, 1 H), 4.34 (dd, J=12.2, 4.1 Hz, 1 H), 3.92-3.88 (m, 1 H), 3.78-3.72 (m, 1 H), 3.64-3.60 (m, 2 H), 3.51-3.42 (m, 1 H), 3.37 (s, 3 H), 2.59 (s, 3 H), 1.69-1.25 (m, 4 H), 0.94 (t, J=7.4 Hz, 3 H); LCMS (MH+, 419) |

TABLE 2-continued

Analytical Data for Representative Compounds

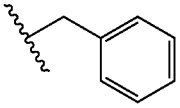

| Cpd. No. | R | R₁ | Analytical Data |
|---|---|---|---|
| (I-2a-26) | n-propyl | 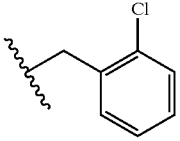 | 7.93 (d, J=8.4 Hz, 1 H), 7.54 (d, J= 2.1 Hz, 1 H), 7.41-7.30 (m, 6 H), 6.23 (m, 1 H), 4.86 (d, J=15.6 Hz, 1 H), 4.51 (dd, J=12.6, 2.1 Hz, 1 H), 4.37 (d, J=16.2 Hz, 1 H), 4.33 (dd, J= 12.0, 4.2 Hz, 1 H), 3.75-3.71 (m, 1 H), 2.57 (s, 3 H), 1.71-1.32 (m, 4 H), 0.91 (t, J=7.2 Hz, 3 H); LCMS (MH+, 451) |
| (I-2a-27) | n-propyl | 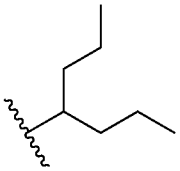 | 7.55 (d, J=2.4 Hz, H), 7.48-7.20 (m, 5 H), 6.16 (s, 1 H), 4.85 (d, J=16.5 Hz, 1 H), 4.58-4.51 (m, 2 H), 4.40 (dd, J=12.6, 3.9 Hz, 1 H), 3.82-3.74 (m, 1 H), 2.56 (s, 3 H), 1.76-1.25 (m, 4 H), 0.94 (t, J=7.4 Hz, 3 H); LCMS (MH+, 485) |
| (I-2a-28) | n-propyl | 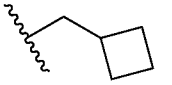 | 7.92 (dd, J=8.1 Hz, 1 H), 7.53 (d, J= 1.8 Hz, 1 H), 7.35 (dd, J=8.6, 2.3 Hz, 1H), 6.18 (s, 1 H), 4.59 (dd, J=12.2, 1.4 Hz, 1 H), 4.10 (dd, J=12.5, 3.5 Hz, 1 H), 3.83 (d, J=10.8 Hz, 1 H), 3.70 (pent, J=7.0 Hz, 1 H), 2.59 (s, 3 H), 1.81-1.18 (m, 12 H), 1.01 (t, J=7.2 Hz, 3 H), 0.93 (t, J=7.1 Hz, 3 H), 0.89 (t, J=7.2 Hz, 3 H); LCMS (MH+, 459) |
| (I-2a-29) | n-propyl | 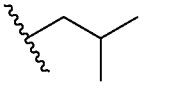 | 7.90 (d, J=8.4 Hz, 1 H), 7.53 (d, J= 2.1 Hz, 1 H), 7.36 (dd, J=8.3, 2.2 Hz, 1 H), 6.15 (s, 1 H), 4.53 (dd, J=12.5, 1.7 Hz, 1 H), 4.32 (dd, J=12.5, 4.1 Hz, 1 H), 3.80-3.72 (m, 1 H), 3.63 (dd, J= 14.6, 6.6 Hz, 1 H), 3.23 (dd, J=14.3, 8.0 Hz, 1 H), 2.77-2.70 (m, 1 H), 2.61 (s, 3 H), 2.16-1.26 (m, 6 H), 0.94 (t, J= 7.2 Hz, 3 H), 1.01-0.83 (m, 4 H); LCMS (MH+, 429). |
| (I-2a-30) | ethyl(S) | 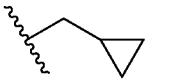 | 7.90 (d, J=8.1 Hz, 1 H), 7.53 (d, J= 2.1 Hz, 1 H), 7.36 (dd, J=8.3, 2.3 Hz, 1 H), 6.12 (s, 1 H), 4.58 (dd, J=12.5, 1.4 Hz, 1 H), 4.36 (dd, J=12.8, 3.5 Hz, 1 H), 3.68-3.65 (m, 1 H), 3.50 (dd, J= 14.0, 6.2 Hz, 1 H), 2.92 (dd, J=14.0, 8.6 Hz, 1 H), 2.59 (s, 3 H), 2.11-2.06 (m, 1 H), 1.80-1.57 (m, 2 H), 1.04-0.98 (m, 9 H), LCMS (MH+, 403). |
| (I-2a-31) | ethyl(S) | | 7.91 (d, J=8.4 Hz, 1 H), 7.53 (d, J= 2.1 Hz, 1 H), 7.34 (dd, J=8.3, 2.3 Hz, 1 H), 6.19 (s, 1 H), 4.59 (dd, J=12.5, 2.0 Hz, 1 H), 4.36 (dd, J=12.3, 3.6 Hz, 1 H), 3.94-3.90 (m, 1 H), 3.59 (dd, J= 14.3, 5.9 Hz, 1 H), 3.06 (dd, J=14.4, 7.2 Hz, 1 H), 2.59 (s, 3 H), 1.78-1.74 (m, 1 H), 1.67-1.59 (m, 1 H), 1.13-1.11 (m, 1 H), 1.02 (t, J=7.5 Hz, 3 H), 0.70-0.61 (m, 2 H); 0.34-0.30 (m, 2 H); LCMS (MH⁺, 401). |

TABLE 2-continued

Analytical Data for Representative Compounds

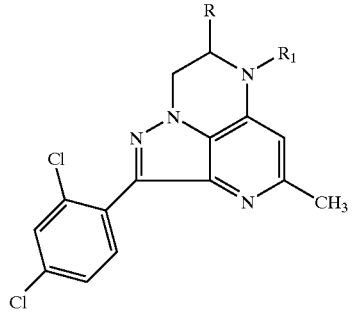

| Cpd. No. | R | R₁ | Analytical Data |
|---|---|---|---|
| (I-2a-32) | ethyl(R) | isobutyl | 7.90 (d, J=8:1 Hz, 1 H), 7.53 (d, 1= 2.1 Hz, 1H), 7.36 (dd, J=8.3, 2.3 Hz, H), 6.12 (s, 1 H), 4.58 (dd, J=12.5, 1.4 Hz, 1 H), 4.36 (dd, J=12.8, 3.5 Hz, 1 H), 3.68-3.65 (m, 1 H), 3.50 (dd, J= 14.0, 6.2 Hz, 1 H), 2.92 (dd, J=14.0, 8.6 Hz, 1 H), 2.59 (s, 3 H), 2.11-2.06 (m, 1 H), 1.80-1.57 (m, 2 H), 1.04-0.98 (m, 9 H), LCMS (MH⁺, 403). |
| (I-2a-33) | ethyl(R) | cyclopropylmethyl | 7.91 (d, J=8.4 Hz, 1 H), 7.53 (d, J= 2.1 Hz, 1 H), 7.34 (dd, J=8.3, 2.3 Hz, 1 H), 6.19 (s, 1 H), 4.59 (dd, J=12.5, 2.0 Hz, 1 H), 4.36 (dd, J=12.3, 3.6 Hz, 1 H), 3.94-3.90 (m, 1 H). 3.59 (dd, J= 14.3, 5.9 Hz, 1 H), 3.06 (dd, J=14.4, 7.2 Hz, 1 H), 2.59 (s, 3 H), 1.78-1.74 (m, 1 H), 1.67-1.59 (m, 1 H), 1.13-1.11 (m, 1 H), 1.02 (t, J=7.5 Hz, 3 H), 0.70-0.61 (m, 2 H), 0.34-0.30 (m, 2 H); LCMS (MH⁺401). |
| (I-2a-34) | iso-propyl | cyclopropylmethyl | 7.90 (d, J=8.4 Hz, 1 H), 7.53 (d, J= 2.1 Hz, 1 H), 7.36 (dd, J=8.4, 2.1 Hz, 1 H), 6.22 (s, 1 H), 4.67 (dd, J=12.3, 2.0 Hz, 1 H), 4.31 (dd, J=12.5, 4.4 Hz, 1 H), 3.82-3.73 (m, 2 H), 3.00 (dd, J= 14.6, 7.7 Hz, 1 H), 2.60 (s, 3 H), 2.14 (m, 1 H), 1.14-1.07 (m, 1 H), 1.02 (d, J= 6.6 Hz, 3 H), 0.85 (d, J=6.6 Hz, 3 H), 0.64-0.55 (m, 2 H), 0.37-0.23 (m, 2 H); LCMS (MH⁺, 415). |
| (I-2a-35) | iso-propyl | n-propyl | 7.90 (d, J=8.1 Hz, 1 H), 7.53 (d, J= 1.8 Hz, 1 H), 7.36 (dd, J=8.4, 2.1 Hz, 1 H), 6.15 (s, 1 H), 4.64 (dd, J=12.6, 1.8 Hz, 1 H), 4.28 (dd, J=12.6, 4.5 Hz, 1 H), 3.77-3.68 (m, 1 H), 3.57-3.52 (m, 1 H), 3.24-3.14 (m, 1 H), 2.59 (s, 3 H), 2.17-2.10 (m, 1 H), 1.76-1.64 (m, 2 H), 1.03 (d, J=6.9 Hz, 3 H), 0.98 (t, J= 7.4 Hz, 3 H), 0.88 (d, J=6.9 Hz, 3 H); LCMS (MH⁺, 403). |
| (I-2a-36) | iso-propyl | isobutyl | LC/MS 417 (MH+) |
| (I-2a-37) | ethyl | 2-ethylbutyl | LC/MS 432 (MH+) |

TABLE 2-continued

Analytical Data for Representative Compounds

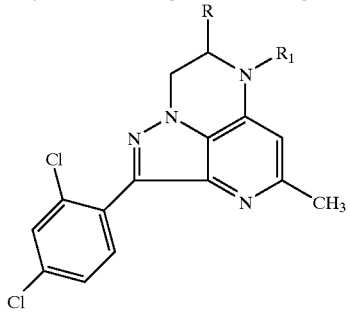

| Cpd. No. | R | R₁ | Analytical Data |
|---|---|---|---|
| (I-2a-38) | ethyl(S) | 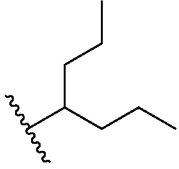 | LC/MS 445 (MH+) |

Example 6

Further Representative Compounds of Structure (I-2A)

The representative compounds of Table 3 were made by the procedures set forth above in Example 5.

TABLE 3

Analytical Data for Representative Compounds

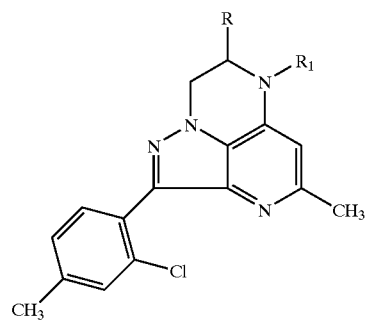

| Cpd. No. | R | R₁ | Analytical Data |
|---|---|---|---|
| (I-2a-39) | ethyl(S) | 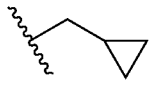 | 7.82 (d, J=8.1 Hz, 1 H), 7.29-7.25 (m, 2 H), 6.18 (s, 1 H), 4.55 (dd, J=12.3, 2.0 Hz, 1 H), 4.32 (dd, J=12.3, 3.6 Hz, 1 H), 3.94-3.89 (m, 1 H), 3.59 (dd, J=14.4, 5.7 Hz, 1 H), 3.06 (dd, J=14.4, 7.2 Hz, 1 H), 2.59 (s, 3 H), 2.53 (s, 3 H), 1.83-1.71 (m, 1 H), 1.67-1.57 (m, 1 H), 1.15-1.10 (m, 1 H), 1.02 (t, J=7.5 Hz, 3 H), 0.7-0.61 (m, 2 H), 0.39-0.28 (m, 2 H); LCMS (MH+, 381). |

TABLE 3-continued

Analytical Data for Representative Compounds

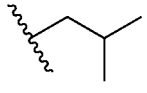

| Cpd. No. | R | R₁ | Analytical Data |
|---|---|---|---|
| (I-2a-40) | ethyl(S) | 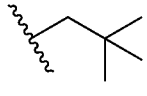 | 7.83 (d, J=8.1 Hz, 1 H), 7.30-7.25 (m, 2 H), 6.11 (s, 1 H), 4.53 (dd, J=12.3, 1.2 Hz, 1 H), 4.33 (dd, J=12.5, 4.1 Hz, 1 H), 3.68-3.63 (m, 1 H), 3.49 (dd, J= 14.1, 6.3 Hz, 1 H), 2.91 (dd, J=14.1, 8.7 Hz, 1 H), 2.59 (s, 3 H), 2.54 (s, 3 H), 2.16-2.05 (m, 1 H). 1.77-1.57 (m, 2 H), 1.04-0.98 (m, 9 H); LCMS (MH⁺, 383). |
| (I-2a-41) | ethyl(S) | 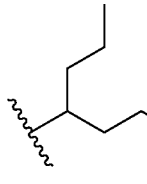 | 7.82 (d, J=8.7 Hz, 1 H), 7.30-7.25 (m, 2 H), 6.17 (s, 1 H), 4.56 (dd, J=12.3, 0.9 Hz, 1 H), 4.42 (dd, J=12.3, 3.3 Hz, 1 H), 3.64-3.60 (m, 1 H), 3.47 (d, J=14.4 Hz, 1 H), 2.91 (d, J=15.0 Hz, 1 H), 2.58 (s, 3 H), 2.54 (s, 3 H), 1.77-1.63 (m, 1 H), 1.61-1.53 (m, 1 H), 1.02 (s, 9 H), 1.07-0.98 (m, 3 H); LCMS (MH⁺, 397). |
| (I-2a-42) | ethyl(S) |  | 7.82 (d, J=8.4 Hz, 1 H), 7.29-7.25 (m, 2 H), 6.17 (s, 1 H), 4.60 (dd, J=12.3, 1.2 Hz, 1 H), 4.06 (dd, J=11.9, 3.5 Hz, 1 H), 3.75-3.68 (m, 2 H), 2.59 (s, 3 H), 2.54 (s, 3 H), 1.78-1.44 (m, 7 H), 1.36-1.21 (m, 3 H), 1.05-0.96 (m, 6 H), 0.90 (t, J=7.2 Hz, 3 H); LCMS (MH⁺, 425). |
| (I-2a-43) | ethyl(S) | 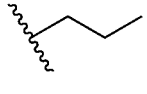 | LC/MS 365 (MH+) |
| (I-2a-44) | iso-butyl(S) |  | LC/MS 397 (MH+) |
| (I-2a-45) | iso-butyl(S) | 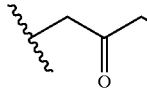 | LC/MS 409 (MH+) |
| (I-2a-46) | ethyl(S) |  | LC/MS 397 (MH+) |

TABLE 3-continued

Analytical Data for Representative Compounds

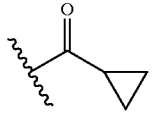

| Cpd. No. | R | R₁ | Analytical Data |
|---|---|---|---|
| (I-2a-47) | ethyl(S) | 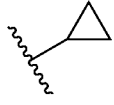 | 7.90 (d, J=8.4 Hz, 1 H), 7.33-7.28 (m, 3 H), 5.30-5.20 (m, 1 H), 4.59 (dd, J= 13.2, 1.2 Hz, 1 H), 4.50 (dd, J=12.6, 3.6 Hz, 1 H), 2.71 (s, 3 H), 2.54 (s, 3 H), 2.30-2.21 (m, 1 H), 1.74-1.41 (m, 4 H), 1.25-0.97 (m, 2 H), 0.97 (t, J=7.5 Hz, 3 H); LCMS (MH⁺, 395). |
| (I-2a-48) | ethyl(S) | 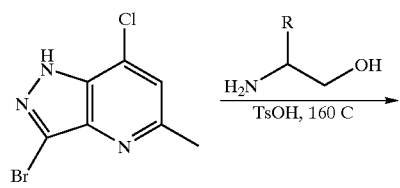 | 7.82 (d, J=7.8 Hz, 1 H), 7.29-7.24 (m, 2 H), 6.46 (s, 1 H), 4.54 (dd, J=12.2, 0.8 Hz, 1 H), 4.27 (dd, J=12.3, 4.2 Hz, 1 H), 3.80-3.74 (m, 1 H), 2.73-2.68 (m, 1 H), 2.62 (s, 3 H), 2.52 (s, 3 H), 1.93-1.82 (m, 2 H), 1.64-1.54 (m, 1 H), 1.05 (t, J= 7.5 Hz, 3 H), 0.90-0.67 (m, 3 H); LCMS (MH⁺, 367). |

Example 7

Synthesis of Further Representative Compounds of Structure (I-2A)

The representative compounds of Table 4 were made by the following procedure (R=ethyl or hyrogen):

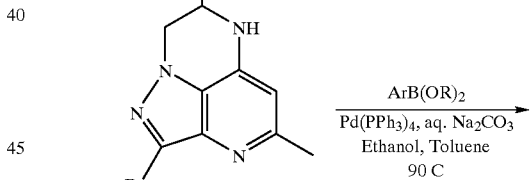

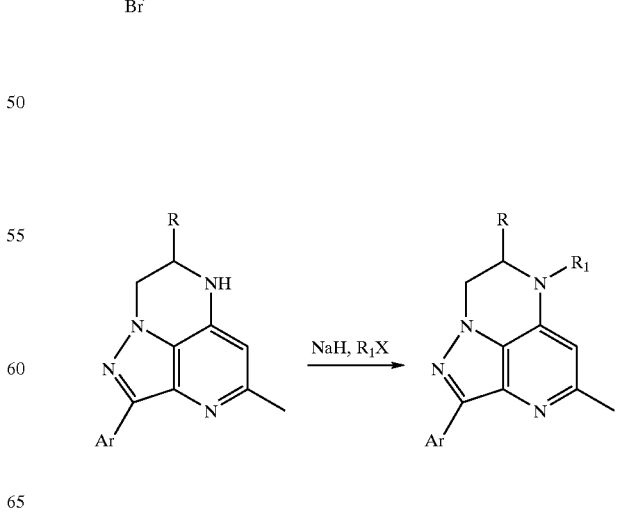

TABLE 4

Analytical Data for Representative Compounds

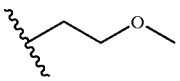

| Cpd. No. | Ar | R | R₁ | Analytical Data |
|---|---|---|---|---|
| (I-2a-49) | 2-trifluoromethyl-4-chlorophenyl | ethyl(S) | 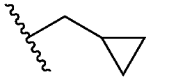 | LC/MS 439 (MH+) |
| (I-2a-50) | 2-trifluoromethyl-4-chlorophenyl | ethyl(S) | 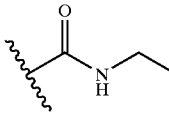 | LC/MS 435 (MH+) |
| (I-2a-51) | 2-trifluoromethyl-4-chlorophenyl | ethyl(S) | 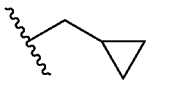 | LC/MS 514 (MH+) |
| (I-2a-52) | 2-methoxy-4-trifluromethyl-phenyl | ethyl(S) | 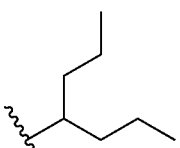 | 7.77(d, J=8.4Hz, 1H), 7.32 (d, J=2.7Hz, 1H), 7.15(dd, J= 8.4, 2.7Hz, 1H), 6.18(s, 1 H), 4.54(dd, J=12.3, 1.8Hz, 1H); 4.33(dd, J=11.9, 4.1 Hz, 1H), 3.95–3.90 (m, 1H); 3.89(s, 3H), 3.58(dd, J= 14.4, 6.0 Hz, 1H), 3.05(dd, J=14.4, 7.2Hz, 1H); 2.57(s, 3 H); 1.86–1.73(m, 1H), 1.67–1.57(m, 1H), 1.57–1.06(m, 1 H), 1.01(t, J=7.4Hz, 3H), 0.70–0.61(m, 2H); 0.37–0.28 (m, 2H); LCMS(MH⁺, 431). |
| (I-2a-53) | 2-trifluoromethyl-4-chlorophenyl | H | 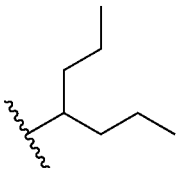 | LC/MS 451 (MH+) |
| (I-2a-54) | 2,5-dimethoxy-4-chlorophenyl | H | 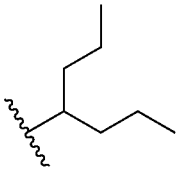 | 7.60(s, 1H); 7.07(s, 1H); 6.27(s, 1 H); 4.49(t, 2H); 3.93(s, 3H); 3.91(s, 3H); 3.86(m, 1H); 3.73(t, 2H); 2.73(s, 3H); 1.60–1.75(m, 4H); 1.20–1.40(m, 4H); 0.95(t, 6H). LC/MS m+1(443, 445). |
| (I-2a-55) | 2-methoxy-4-trifluoromethyl-phenyl | H | | 7.75(d, J=8.4 Hz, 1H); 7.32 (d, J=2.7Hz, 1H); 7.15 (dd, J= 8.7, 2.7Hz, 1H); 6.21 (s, 1 H); 4.42(t, J=5.3Hz, 2H); 3.89 (s, 3 H); 3.86–3.80(m, 1 H); 3.65 (t, J=5.3Hz, 2H); 2.56(s, 3H); 1.76–1.58 (m, 4 H); 1.41–1.24(m, 4H); 0.94(t, J=7.2Hz, 6H); LCMS (MH⁺, 447 |

TABLE 4-continued

Analytical Data for Representative Compounds

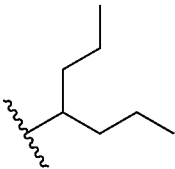

| Cpd. No. | Ar | R | R₁ | Analytical Data |
|---|---|---|---|---|
| (I-2a-56) | 2-methoxy-4-methylphenyl | H | 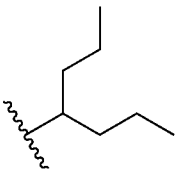 | 7.79 (d, J=7.5Hz, 1H); 6.89 (d, J=7.5Hz, 1H); 6.86(br s, 1H); 6.21(s, 1H); 4.46(t, J= 5.3Hz, 2H); 3.92 (s, 3H); 3.88–3.83(m, 1H); 3.66(t, J= 5.3Hz, 2H); 2.66(s, 3H); 2.41(s, 3H); 1.71–1.53(m, 4H); 1.41–1.25(m, 4H); 0.93(t, J=7.4Hz, 6H); LCMS (MH⁺, 393). |
| (I-2a-57) | 4-methyl-6-dimethylamino-pyridin-3-yl | H | 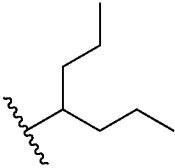 | 8.58(s, 1H); 6.46(s, 1H); 6.20(s, 1H); 4.41(t, 2H); 3.86(m, 1H); 3.66(t, 2H); 3.12(s, 6H); 2.58(s, 3H); 2.48(s, 3H); 1.50–1.72(m, 4H); 1.28–1.44(m, 4H); 0.96(t, 6H). LC/MS m+1(407). |
| (I-2a-58) | 2-methoxy-4-isopropylphenyl | H | 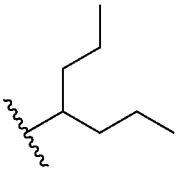 | LC/MS 421(MH+) |
| (I-2a-59) | 2-methoxy-4-methylphenyl | H | 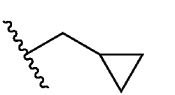 | LC/MS 393 (MH+) |
| (I-2a-60) | 2,4-dimethyl-phenyl | ethyl(S) | 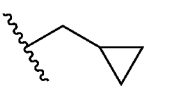 | LC/MS 361 (MH+) |
| (I-2a-61) | 2-methoxy-4-isopropylphenyl | ethyl(S) | 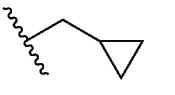 | LC/MS 405 (MH+) |
| (I-2a-62) | 2-formyl-4-methoxyphenyl | ethyl(S) | 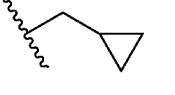 | LC/MS 391 (MH+) |
| (I-2a-63) | 2,4,6-trimethyl-phenyl | ethyl(S) | | LC/MS 375 (MH+) |

TABLE 4-continued

Analytical Data for Representative Compounds

| Cpd. No. | Ar | R | R₁ | Analytical Data |
|---|---|---|---|---|
| (I-2a-64) | 2,4,6-trimethyl-phenyl | H | (3-propylhexyl group) | LC/MS 391 (MH+) |
| (I-2a-65) | 2-chloro-4-(C(=O)OCH₃)-phenyl | ethyl(S) | (cyclopropylmethyl) | LC/MS 425 (MH+) |
| (I-2a-66) | 2-chloro-4-C(OH)(CH₃)₂-phenyl | ethyl(S) | (cyclopropylmethyl) | LC/MS 425 (MH+) |
| (I-2a-67) | 2-trifluoromethyl-4-isopropyl-phenyl | ethyl(S) | (cyclopropylmethyl) | LC/MS 443 (MH+) |
| (I-2a-68) | 2-chloro-4,6-dimethylphenyl | ethyl(S) | (cyclopropylmethyl) | LC/MS 395 (MH+) |
| (I-2a-69) | 2-methoxy-4-trifluoromethyl-phenyl | ethyl(S) | (isobutyl) | 1.00(9 H, t), 1.66(2H, m), 2.10(1H, m), 2.55(3H, s), 2.90(1H, q), 3.48(1H, q), 3.65 (1H, m), 3.89(3H, s), 4.33 (1H, m), 4.53 (1H, d), 6.12 (1H,s), 7.15(1H, m), 7.32 (1H, d), 7.78(1H, d). |
| (I-2a-70) | 2,4,6-trimethyl-phenyl | ethyl(S) | (isobutyl) | 1.01(9H, t)1.65(2H, m), 2.12 (7H, m), 2.30(3H, s),2.52 (3H, s), 2.90(1H, m), 3.47 (1H, m), 3.64(1H, m), 4.32 (1H, d), 4.50(1H, d), 6.07 (1H, s), 6.91(2H, s). |
| (I-2a-71) | 2,4-dimethyl-phenyl | ethyl(S) | (isobutyl) | 1.00(9H, m), 1.65(2H, m), 2.09(1H, m), 2.35(3H, s), 2.51(3H, s), 2.57(3H, s), 2.90 (1H, m), 3.48(1H, m), 3.63 (1H, m), 4.31(1H, m), 5.51 (1H, d), 6.09(1H, s), 7.09 (2H, m), 7.72(1H, d). |
| (I-2a-72) | 2-methoxy-4-trifluoromethyl-methyl | ethyl(S) | (3-pyridylmethyl) | LC/MS 468 (MH+) |
| (I-2a-73) | 2-methoxy-4-trifluoromethyl-phenyl | ethyl(S) | (allyl/but-3-enyl) | LC/MS 417 (MH+) |

TABLE 4-continued

Analytical Data for Representative Compounds

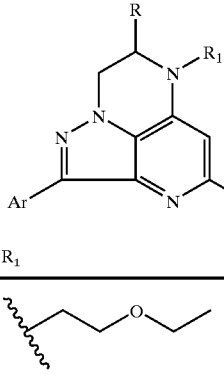

| Cpd. No. | Ar | R | R₁ | Analytical Data |
|---|---|---|---|---|
| (I-2a-74) | 2-methoxy-4-trifluoromethyl-phenyl | ethyl(S) | 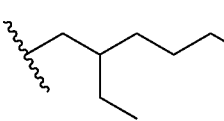 | LC/MS 449 (MH+) |
| (I-2a-75) | 2-methoxy-4-trifluoromethyl-phenyl | ethyl(S) | 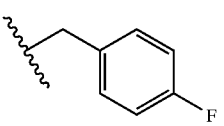 | LC/MS 489 (MH+) |
| (I-2a-76) | 2-methoxy-4-trifluoromethyl-phenyl | ethyl(S) | 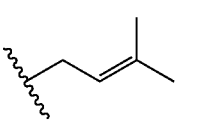 | LC/MS 485 (MH+) |
| (I-2a-77) | 2-methoxy-4-trifluoromethyl-phenyl | ethyl(S) | 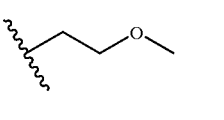 | LC/MS 445 (MH+) |
| (I-2a-78) | 2-methoxy-4-trifluoromethyl-phenyl | ethyl(S) | 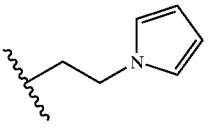 | LC/MS 435 (MH+) |
| (I-2a-79) | 2-methoxy-4-trifluoromethyl-phenyl | ethyl(S) | 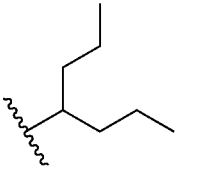 | LC/MS 470 (MH+) |
| (I-2a-80) | 2-methoxy-4-trifluoromethyl-phenyl | methyl(S) | 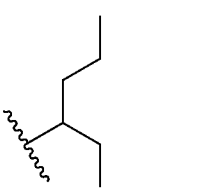 | — |
| (I-2a-81) | 2-methoxy-4-trifluoromethyl-phenyl | methyl(S) | | — |
| (I-2a-82) | 2-methoxy-4-trifluoromethyl-phenyl | methyl(S) | 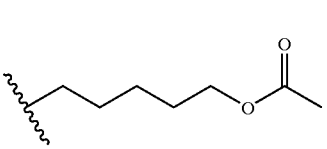 | — |

TABLE 4-continued

Analytical Data for Representative Compounds

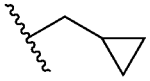

| Cpd. No. | Ar | R | R₁ | Analytical Data |
|---|---|---|---|---|
| (I-2a-83) | 2-methoxy-4-trifluoromethyl-phenyl | methyl(S) | 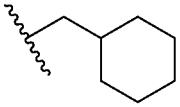 | — |
| (I-2a-84) | 2-methoxy-4-trifluoromethyl-phenyl | methyl(S) | 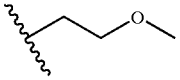 | — |
| (I-2a-85) | 2-methoxy-4-trifluoromethyl-phenyl | methyl(S) | 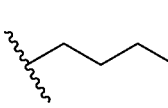 | — |
| (I-2a-86) | 2-methoxy-4-trifluoromethyl-phenyl | methyl(S) | 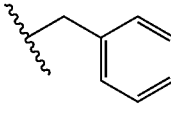 | — |
| (I-2a-87) | 2-methoxy-4-trifluoromethyl-phenyl | methyl(S) |  | — |
| (I-2a-88) | 2-methoxy-4-trifluoromethyl-phenyl | methyl(S) | 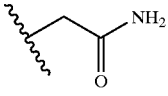 | — |
| (I-2a-89) | 2-methoxy-4-trifluoromethyl-phenyl | methyl(S) | 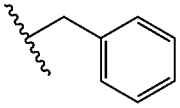 | — |
| (I-2a-90) | 2-methoxy-4-trifluoromethyl-phenyl | methyl(S) |  | — |
| (I-2a-91) | 2-methoxy-4-trifluoromethyl-phenyl | methyl(S) | 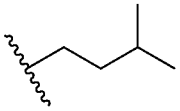 | — |
| (I-2a-92) | 2-methoxy-4-trifluoromethyl-phenyl | methyl(S) | 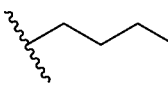 | — |
| (I-2a-93) | 2-methoxy-4-trifluoromethyl-phenyl | methyl(S) |  | — |

TABLE 4-continued

Analytical Data for Representative Compounds

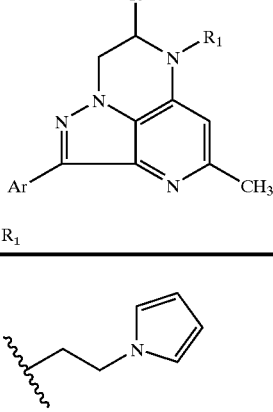

| Cpd. No. | Ar | R | R₁ | | Analytical Data |
|---|---|---|---|---|---|
| (I-2a-94) | 2-methoxy-4-trifluoromethyl-phenyl | methyl(S) | 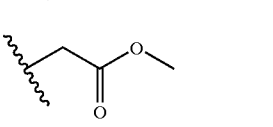 | | — |
| (I-2a-95) | 2-methoxy-4-trifluoromethyl-phenyl | methyl(S) | 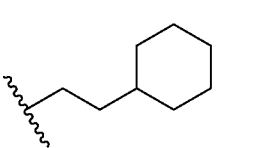 | | — |
| (I-2a-96) | 2-methoxy-4-trifluoromethyl-phenyl | methyl(S) | 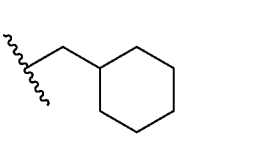 | | — |
| (I-2a-97) | 2-methoxy-4-trifluoromethyl-phenyl | methyl(S) | 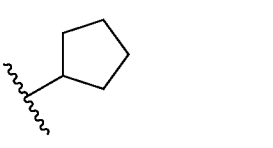 | | — |
| (I-2a-98) | 2-methoxy-4-trifluoromethyl-phenyl | methyl(S) | 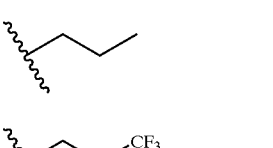 | | — |
| (I-2a-99) | 2-methoxy-4-trifluoromethyl-phenyl | methyl(S) | 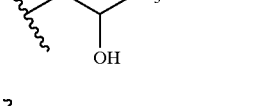 | | — |
| (I-2a-100) | 2-methoxy-4-trifluoromethyl-phenyl | ethyl | 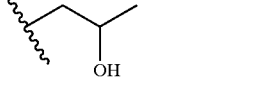 | | — |
| (I-2a-101) | 2-methoxy-4-trifluoromethyl-phenyl | ethyl | 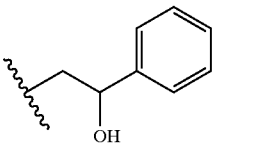 | | — |
| (I-2a-102) | 2-methoxy-4-trifluoromethyl-phenyl | ethyl | 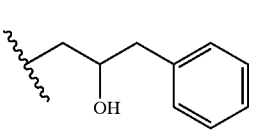 | | — |
| (I-2a-103) | 2-methoxy-4-trifluoromethyl-phenyl | ethyl | | | — |

TABLE 4-continued

Analytical Data for Representative Compounds

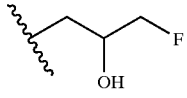

| Cpd. No. | Ar | R | R₁ | Analytical Data |
|---|---|---|---|---|
| (I-2a-104) | 2-methoxy-4-trifluoromethyl-phenyl | ethyl |  | — |
| (I-2a-105) | 2-methoxy-4-trifluoromethyl-methyl | ethyl(S) | 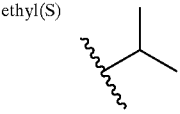 | LC/MS 405 (MH+) |
| (I-2a-106) | 2-methoxy-4-trifluoromethyl-phenyl | ethyl(S) | 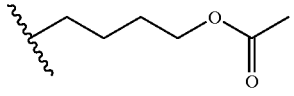 | LC/MS 419 (MH+) |
| (I-2a-107) | 2-methoxy-4-trifluoromethyl-phenyl | ethyl(S) | 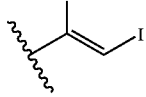 | LC/MS 491 (MH+) |
| (I-2a-108) | 2-methoxy-4-trifluoromethyl-phenyl | ethyl(S) | 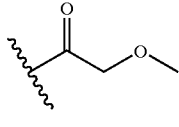 | LC/MS 547 (MH+) |
| (I-2a-109) | 2-methoxy-4-trifluoromethyl-phenyl | ethyl | 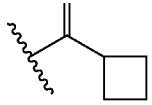 | LC/MS 449 (MH+) |
| (I-2a-110) | 2-methoxy-4-trifluoromethyl-phenyl | ethyl | 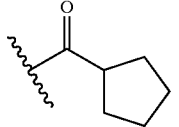 | LC/MS 459 (MH+) |
| (I-2a-111) | 2-methoxy-4-trifluoromethyl-phenyl | ethyl | 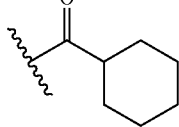 | LC/MS 473 (MH+) |
| (I-2a-112) | 2-methoxy-4-trifluoromethyl-phenyl | ethyl | 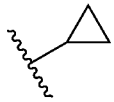 | LC/MS 487 (MH+) |
| (I-2a-113) | 2-methoxy-4-trifluoromethyl-methyl | ethyl | | LC/MS 417 (MH+) |

TABLE 4-continued

Analytical Data for Representative Compounds

| Cpd. No. | Ar | R | R₁ | Analytical Data |
|---|---|---|---|---|
| (I-2a-114) | 2-methoxy-4-trifluoromethyl-phenyl | ethyl | cyclobutylmethyl | LC/MS 430 (MH+) |
| (I-2a-115) | 2-methoxy-4-trifluoromethyl-phenyl | ethyl | 2-methylbutyl | LC/MS 447 (MH+) |
| (I-2a-116) | 2-methoxy-4-trifluoromethyl-phenyl | ethyl | 2-(phenylthio)ethyl | LC/MS 513 (MH+) |
| (I-2a-117) | 2-methoxy-4-trifluoromethyl-phenyl | ethyl | cinnamyl | LC/MS 493 (MH+) |
| (I-2a-118) | 2-methoxy-4-trifluoromethyl-phenyl | ethyl | 2-(trifluoromethoxy)benzyl | LC/MS 551 (MH+) |
| (I-2a-119) | 2-methoxy-4-trifluoromethyl-phenyl | ethyl | 4-(methylsulfonyl)benzyl | LC/MS 545 (MH+) |
| (I-2a-120) | 2-methoxy-4-trifluoromethyl-phenyl | methyl(S) | cyclopropylcarbonyl | LC/MS 431 (MH+) |
| (I-2a-121) | 2-methoxy-4-trifluoromethyl-methyl | methyl(S) | cyclopentylcarbonyl | LC/MS 459 (MH+) |
| (I-2a-122) | 2-methoxy-4-trifluoromethyl-phenyl | methyl(S) | propanoyl | LC/MS 419 (MH+) |
| (I-2a-123) | 2-methoxy-4-trifluoromethyl-phenyl | methyl(S) | butanoyl | LC/MS 433 (MH+) |

TABLE 4-continued

Analytical Data for Representative Compounds

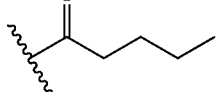

| Cpd. No. | Ar | R | R₁ | | Analytical Data |
|---|---|---|---|---|---|
| (I-2a-124) | 2-methoxy-4-trifluoromethyl-phenyl | methyl(S) | 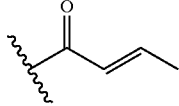 | | LC/MS 447 (MH+) |
| (I-2a-125) | 2-methoxy-4-trifluoromethyl-phenyl | methyl(S) | 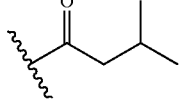 | | LC/MS 431 (MH+) |
| (I-2a-126) | 2-methoxy-4-trifluoromethyl-phenyl | methyl(S) | 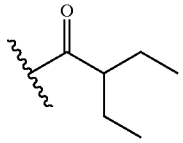 | | LC/MS 447 (MH+) |
| (I-2a-127) | 2-methoxy-4-trifluoromethyl-phenyl | methyl(S) | 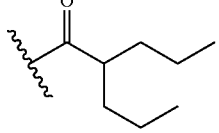 | | LC/MS 461 (MH+) |
| (I-2a-128) | 2-methoxy-4-trifluoromethyl-phenyl | methyl(S) | 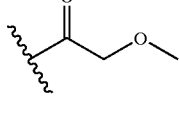 | | LC/MS 489 (MH+) |
| (I-2a-129) | 2-methoxy-4-trifluoromethyl-methyl | methyl(S) | 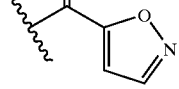 | | LC/MS 435 (MH+) |
| (I-2a-130) | 2-methoxy-4-trifluoromethyl-phenyl | methyl(S) |  | | LC/MS 458 (MH+) |
| (I-2a-131) | 2-methoxy-4-trifluoromethyl-phenyl | methyl(S) |  | | LC/MS 391 (MH+) |
| (I-2a-132) | 2-methoxy-4-trifluoromethyl-phenyl | methyl(S) | 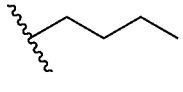 | | LC/MS 403 (MH+) |
| (I-2a-133) | 2-methoxy-4-trifluoromethyl-phenyl | methyl(S) | | | LC/MS 419 (MH+) |

TABLE 4-continued

Analytical Data for Representative Compounds

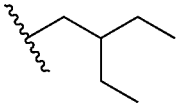

| Cpd. No. | Ar | R | R₁ | Analytical Data |
|---|---|---|---|---|
| (I-2a-134) | 2-methoxy-4-trifluoromethyl-phenyl | methyl(S) |  | LC/MS 447 (MH+) |
| (I-2a-135) | 2-methoxy-4-trifluoromethyl-phenyl | methyl(S) |  | LC/MS 417 (MH+) |
| (I-2a-136) | 2-methoxy-4-trifluoromethyl-phenyl | methyl(S) | 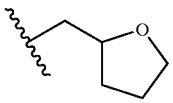 | LC/MS 431 (MH+) |
| (I-2a-137) | 2-methoxy-4-trifluoromethyl-methyl | methyl(S) | 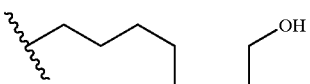 | LC/MS 447 (MH+) |
| (I-2a-138) | 2-methoxy-4-trifluoromethyl-phenyl | methyl(S) | 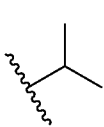 | LC/MS 491 (MH+) |
| (I-2a-139) | 2-methoxy-4-trifluoromethyl-phenyl | methyl(S) | 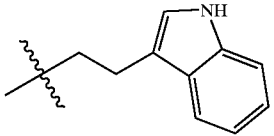 | LC/MS 405 (MH+) |
| (I-2a-140) | 2-methoxy-4-trifluoromethyl-phenyl | methyl(S) | 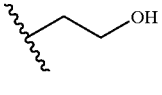 | LC/MS 506 (MH+) |
| (I-2a-141) | 2-methoxy-4-trifluoromethyl-phenyl | ethyl(S) | 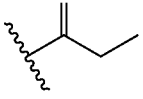 | LC/MS 421 (MH+) |
| (I-2a-142) | 2-methoxy-4-trifluoromethyl-phenyl | ethyl(S) | 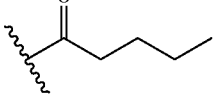 | LC/MS 433 (MH+) |
| (I-2a-143) | 2-methoxy-4-trifluoromethyl-phenyl | ethyl(S) |  | LC/MS 461 (MH+) |

TABLE 4-continued

Analytical Data for Representative Compounds

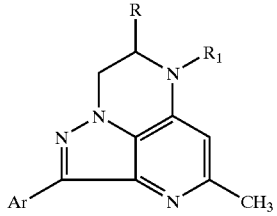

| Cpd. No. | Ar | R | R₁ | Analytical Data |
|---|---|---|---|---|
| (I-2a-144) | 2-methoxy-4-trifluoromethyl-phenyl | ethyl(S) | 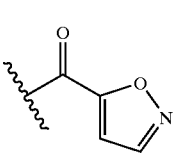 | LC/MS 503 (MH+) |
| (I-2a-145) | 2-methoxy-4-trifluoromethyl-methyl | ethyl(S) | 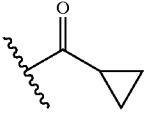 | LC/MS 472 (MH+) |
| (I-2a-146) | 2-methoxy-4-trifluoromethyl-phenyl | ethyl(S) | 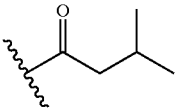 | LC/MS 445 (MH+) |
| (I-2a-147) | 2-methoxy-4-trifluoromethyl-phenyl | ethyl(S) | 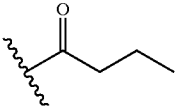 | LC/MS 461 (MH+) |
| (I-2a-148) | 2-methoxy-4-trifluoromethyl-phenyl | ethyl(S) | 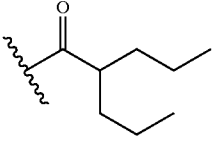 | LC/MS 447 (MH+) |
| (I-2a-149) | 2-trifluoromethyl-4-methoxy-phenyl | H | 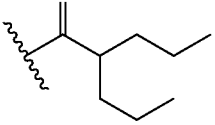 | — |
| (I-2a-150) | 2-trifluoromethyl-4-methoxy-phenyl | ethyl(S) | 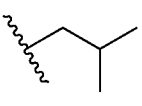 | — |
| (I-2a-151) | 2-trifluoromethyl-4-methoxy-phenyl | ethyl(S) | 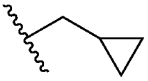 | — |
| (I-2a-152) | 2-trifluoromethyl-4-methoxy-phenyl | ethyl(S) | 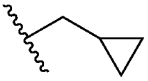 | — |

TABLE 4-continued

Analytical Data for Representative Compounds

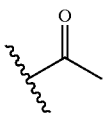

| Cpd. No. | Ar | R | R₁ | Analytical Data |
|---|---|---|---|---|
| (I-2a-153) | 2-methoxy-4-trifluoromethyl-phenyl | ethyl | 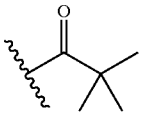 | LC/MS 419 (MH+) |
| (I-2a-154) | 2-methoxy-4-trifluoromethyl-methyl | ethyl | 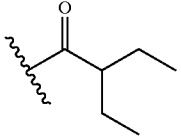 | LC/MS 461 (MH+) |
| (I-2a-155) | 2-methoxy-4-trifluoromethyl-phenyl | ethyl | 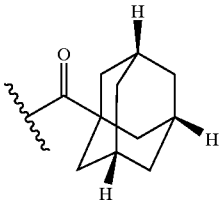 | LC/MS 475 (MH+) |
| (I-2a-156) | 2-methoxy-4-trifluoromethyl-phenyl | ethyl | 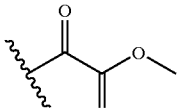 | LC/MS 539 (MH+) |
| (I-2a-157) | 2-methoxy-4-trifluoromethyl-phenyl | ethyl | 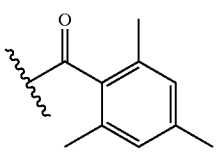 | LC/MS 463 (MH+) |
| (I-2a-158) | 2-methoxy-4-trifluoromethyl-phenyl | ethyl | 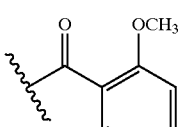 | LC/MS 523 (MH+) |
| (I-2a-159) | 2-methoxy-4-trifluoromethyl-methyl | ethyl | 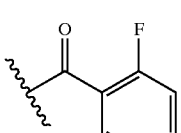 | LC/MS 511 (MH+) |
| (I-2a-160) | 2-methoxy-4-trifluoromethyl-phenyl | ethyl |  | LC/MS 517 (MH+) |

TABLE 4-continued

Analytical Data for Representative Compounds

| Cpd. No. | Ar | R | R₁ | Analytical Data |
|---|---|---|---|---|
| (I-2a-161) | 2-methoxy-4-trifluoromethyl-phenyl | ethyl | 2-(trifluoromethyl)benzoyl | LC/MS 549 (MH+) |
| (I-2a-162) | 2-methoxy-4-trifluoromethyl-phenyl | ethyl | 1-naphthoyl | LC/MS 531 (MH+) |
| (I-2a-163) | 2-methoxy-4-trifluoromethyl-phenyl | ethyl | 2-naphthoyl | LC/MS 531 (MH+) |
| (I-2a-164) | 2-methoxy-4-trifluoromethyl-methyl | ethyl | 2-thienylacetyl | LC/MS 501 (MH+) |
| (I-2a-165) | 2-methoxy-4-trifluoromethyl-phenyl | ethyl | 4-methyl-1,2,3-thiadiazol-5-ylcarbonyl | LC/MS 503 (MH+) |
| (I-2a-166) | 2-chloro-4-methoxyphenyl | ethyl(S) | cyclopropylmethyl | 7.81(d, J=8.7Hz, 1H), 7.07 (d, J=3.0Hz, 1H), 6.93(dd, J= 8.7, 3.0Hz, 1H), 6.17(s, 1H), 4.57 (12.3, 1.8Hz, 1H), 4.34(dd, J=12.3, 4.2Hz, 1 H), 3.93–3.88(m, 1H), 3.84(s, 3H), 3.58(dd, J=14.1, 6.0 Hz, 1H), 3.05(dd, J=14.6, 7.1Hz, __H); LC/MS 397 (MH+) |
| (I-2a-167) | 2-methyl-4-chlorophenyl | ethyl(S) | cyclopropylmethyl | 7.79(d, J=8.4Hz, 1H), 7.29– 7.27 (m, 2H), 6.19(s, 1H), 4.56 (dd, J=12.3, 1.8Hz, 1 H), 4.33(dd,J=12.3, 4.2Hz, 1H), 3.97–3.91(m, 1H), 3.63 (dd, J=14.1, 5.7Hz, 1H), 3.08(dd, J=14.4, 7.5Hz, 1 H), 2.62(s, 3H), 2.52(s. 3H), 1.88–1; LC/MS 381(MH+) |

TABLE 4-continued

Analytical Data for Representative Compounds

| Cpd. No. | Ar | R | R₁ | Analytical Data |
|---|---|---|---|---|
| (I-2a-168) | 2-methyl-4-chlorophenyl | H | 2-ethylpentyl | 7.75(d, J=8.4Hz, 1H), 7.28–7.21(m, 2H), 6.21(s, 1H), 4.42 (dd, J=5.4, 5.1Hz, 2H 3.89–3.81(m, 1H), 3.65(dd, J=5.4, 5.1Hz, 2H), 2.57(s, 3H), 2.51(s, 3H), 1.74–1.53(m, 4H), 1.43–1.24(m, 4H), 0.94 (t, J=7.4Hz, 6H); LC/MS 397(MH+) |
| (I-2a-169) | 2,4-dimethyl-phenyl | H | 2-ethylpentyl | 7.66(d, J=7.5Hz, 1H), 7.11–7.08(m, 2H), 6.20(s, 1H), 4.42(dd, J=5.5, 4.8Hz, 2H 3.89–3.81(m, 1H), 3.65(dd, J=5.4, 5.1Hz, 2H), 2.58(s, 3H), 2.48(s, 3H), 2.35(s, 3H), 1.72–1.53(m, 4H), 1.43–1.30 (m, 4H), 0.94(t, J=7.2Hz, 6H); LC/MS 377(MH+) |
| (I-2a-170) | 2,4-dimethyl-6-chlorophenyl | H | 2-ethylpentyl | 7.15(s, 1H), 7.01(s, 1H), 6.20(s, 1H), 4.50–4.39(m, 2H), 3.89–3.81(m, 1H), 3.67 (dd, t, J=5.3Hz, 2H), 2.56(s, 3H), 2.33(s, 3H), 2.17(s, 3H), 1.72–1.54(m, 4H), 1.44–1.32(m, 4H), 0.95(t, J=7.5 Hz, 6H); LC/MS 411(MH+) |
| (I-2a-171) | 2-chloro-4-trifluoromethyl-phenyl | ethyl(S) | cyclopropylmethyl | 8.13(d, J=8.4Hz, 1H), 7.79 (s, 1H), 7.62(d, J=8.1Hz, 1H), 6.21(s, 1H), 4.61(dd, J=12.6, 1.8Hz, 1H), 4.39(dd, J=12.5, 3.8Hz, 1H), 3.95–3.93 (m, 1H), 3.60(dd, J=14.4, 5.7Hz, 1H), 3.06(dd, J=14.1, 7.2Hz, 1H), 2.60(s, 3H H); LC/MS 435(MH+) |
| (I-2a-172) | 2-chloro-4-trifluoromethyl-phenyl | H | 2-ethylpentyl | 8.10(d, J=8.4Hz, 1H), 7.78 (s, 1H), 7.62(d, J=8.4Hz, 1H) 6.24(s, 1H), 4.48(dd, J=6.0, 4.8Hz, 2H), 3.91–3.82 (m, 1H), 3.67(dd, J=5.4, 5.1 Hz, 2H), 2.59(s, 3H), 1.74–1.54,(m, 4H), 1.43–1.31(m, 4H), 0.94(t, J=7.2Hz, 6H); LC/MS 451 (MH+) |
| (I-2a-173) | 2-trifluoromethyl-4-isopropylphenyl | ethyl(S) | isobutyl | 1.01(9H, t), 1.28(6H, d), 1.63 (2H, m), 2.15(1H, m), 2.56 (3H, s), 2.95 (2H, m), 3.49 (1H, m), 3.65(1H, m), 4.36 (1H, m), 4.53(1H, m), 6.51 (1H, s), 7.48(1H, d), 7.63(1H, s), 7.76(1H, d) |
| (I-2a-174) | 2-methyl-4-methoxyphenyl | ethyl(S) | cyclopropylmethyl | 0.31(2H, m), 0.64(2H, m), 1.02(3H, t). 1.10(1H, m), 1.63(1H, m), 1.75(1H, m), 2.06(1H, s), 2.53(3H, s), 2.58 (3H, s), 3.04(1H, q), 3.57(1H, q), 3.83(3H, s), 4.29(1H, m), 4.53(1H, d), 6.16(lH, s), 6.84 (2H, m), 7.78(1H, d) |

TABLE 4-continued

Analytical Data for Representative Compounds

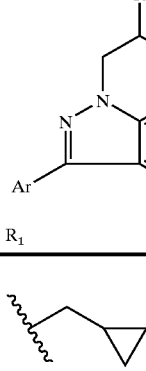

| Cpd. No. | Ar | R | R₁ | Analytical Data |
|---|---|---|---|---|
| (I-2a-175) | 2-chloro-4-fluorophenyl | ethyl(S) | 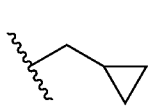 | 0.32(2H, m), 0.65(2H, m), 1.02(3H, t), 1.10(1H, m), 1.67(2H, m), 2.58(3H, s), 3.05(1H, q), 3.59(1H, q), 3.92 (1H, m), 4.35(1H, m), 4.57 (1H, d), 6.19(1H, s), 7.10(1H, m), 7.27(1H, m), 7.90(1H, m) |
| (I-2a-176) | 2-(2-chloro-4-fluorophenyl)-4-fluorophenyl | ethyl(S) | | LC/MS 379(MH+) |
| (I-2a-177) | 4-fluorophenyl | ethyl(S) | 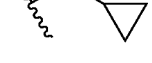 | 0.31(2H, m), 0.64(2H, m), 1.01(3H, t), 1.10(1H, m), 1.65(2H, m), 2.62(3H, s), 3.04(1H, q), 3.57(1H, q), 3.89 1H, m), 4.28(1H, m), 4.53 (1H, d), 6.18(1H, s), 7.16(2H, t), 8.45(2H, m) |
| (I-2a-178) | 2-methoxy-4-chlorophenyl | ethyl(S) | 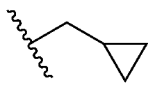 | 0.31(2H, m), 0.63(2H, m), 1.01(3H, t), 1.10(1H, m), 1.70(2H, m), 2.58(3H, s), 3.04(1H, q), 3.57(1H, q), 3.87 (1H, m), 3.90(3H, s), 4.32 (1H, m), 4.58(1H, d), 6.16 (1H, s), 7.02(1H, d), 7.08(1H, d), 8.06(1H, d) |
| (I-2a-179) | 2-methyl-4-methoxyphenyl | ethyl(S) | 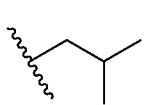 | 1.00(9H, q), 1.68(2H, m), 2.09(1H, m), 2.53(3H, s), 2.57(3H, s), 2.90(1H, q), 3.48 (1H, q), 3.63(1H, m), 3.83 (3H, s), 4.30(1H, m), 4.51 (1H, d), 6.08(1H, s), 6.84(2H, m), 7.77(1H, d) |
| (I-2a-180) | 2,4-dimethoxyphenyl | ethyl(S) | 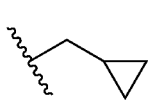 | 0.30(2H, m), 0.63(2H, m), 1.01(3H, t), 1.09(1H, m), 1.70(2H, m), 2.09(1H, s), 2.58(3H, s), 3.03(1H, q), 3.57 (1H, q), 3.86(3H, s), 3.88(3H, s) 4.30(1H, m), 4.57(1H, d), 6.15(1H, s), 6.62(2H, m), 8.03(1H, d) |
| (I-2a-181) | 2-methoxy-4-chlorophenyl | H | 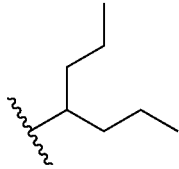 | 0.93(6H, t), 1.34(4H, m), 1.63(4H, m), 2.58(3H, s), 3.62(2H, d), 3.84(1H, m), 3.90(3H, s), 4.45(2H, t), 6.20 (1H, s), 7.04(2H, m), 8.00 (1H, d) |
| (1-2a-182) | 2-chloro-4-methoxyphenyl | H | 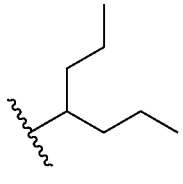 | 0.94(6H, t), 1.36(4H, m), 1.63(4H, m), 2.58(3H, s), 3.65(2H, t), 3.84(4H, m), 4.44(2H, t), 6.21(1H, s), 6.32 (1H, d), 7.07(1H, d), 7.79 (1H, d) |

TABLE 4-continued

Analytical Data for Representative Compounds

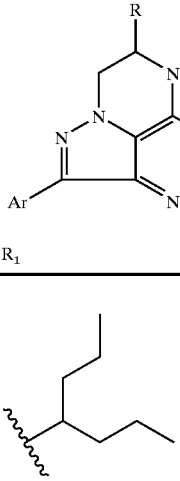

| Cpd. No. | Ar | R | R₁ | | Analytical Data |
|---|---|---|---|---|---|
| (1-2a-183) | 2-chloro-4-carboxyphenyl | H | 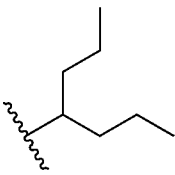 | | 0.78(6H, t), 1.20(5H, m), 1.43(3H, m), 2.33(3H, s), 3.43(2H, m), 3.67(1H, m), 4.25(2H, m), 6.01(1H, s), 7.45 (1H, d), 7.86(1H, d), 7.97 (1H, s) |
| (1-2a-184) | 2,6-dimethyl-4-methoxyphenyl | H | 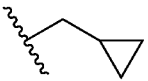 | | 0.95(6H, t), 1.40(4H, m), 1.64(4H, m), 2.16(6H, s), 2.54(3H, s), 3.66(2H, t), 2.81 (4H, m), 4.41(2H, t), 6.18 (1H, s), 6.67(2H, s) |
| (1-2a-185) | 2,6-dimethyl-4-methoxyphenyl | ethyl(S) | 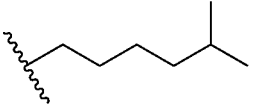 | | 0.34(2H, m), 0.66(2H, m), 1.02(3H,t), 1.13(1H, m), 1.74(4H, m), 2.15(5H, s), 2.54(3H, s), 3.05(1H, q), 3.58 (1H, m), 3.81(3H, s), 3.92 (1H, m), 4.32(1H, m), 4.52 (1H d), 6.16(1H, s), 6.67 (2H, s) |
| (I-2a-186) | 2-methoxy-4-trifluoromethyl-phenyl | ethyl(S) | 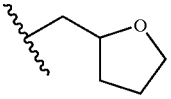 | | — |
| (I-2a-187) | 2-methoxy-4-trifluoromethyl-phenyl | ethyl(S) | 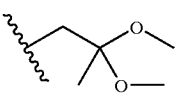 | | — |
| (I-2a-188) | 2-methoxy-4-trifluoromethyl-phenyl | ethyl(S) | 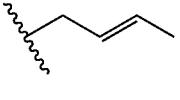 | | — |
| (I-2a-189) | 2-methoxy-4-trifluoromethyl-phenyl | ethyl(S) | 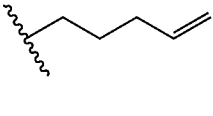 | | — |
| (I-2a-190) | 2-methoxy-4-trifluoromethyl-phenyl | ethyl(S) | 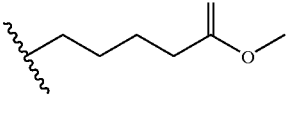 | | — |
| (I-2a-191) | 2-methoxy-4-trifluoromethyl-phenyl | ethyl(S) | | | — |

TABLE 4-continued

Analytical Data for Representative Compounds

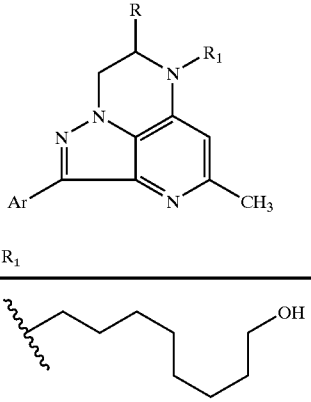

| Cpd. No. | Ar | R | R₁ | Analytical Data |
|---|---|---|---|---|
| (I-2a-192) | 2-methoxy-4-trifluoromethyl-phenyl | ethyl(S) | 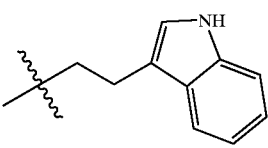 | — |
| (I-2a-193) | 2-methoxy-4-trifluoromethyl-phenyl | ethyl(S) | 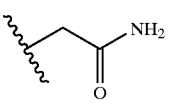 | — |
| (I-2a-194) | 2-methoxy-4-trifluoromethyl-phenyl | ethyl(S) | 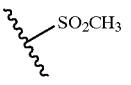 | — |
| (I-2a-195) | 2-methoxy-4-trifluoromethyl-phenyl | ethyl(S) | 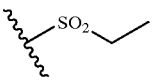 | — |
| (I-2a-196) | 2-methoxy-4-trifluoromethyl-phenyl | ethyl(S) | 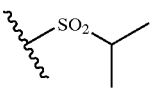 | — |
| (I-2a-197) | 2-methoxy-4-trifluoromethyl-phenyl | ethyl(S) | 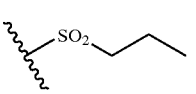 | — |
| (I-2a-198) | 2-methoxy-4-trifluoromethyl-phenyl | ethyl(S) | 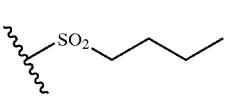 | — |
| (I-2a-199) | 2-methoxy-4-trifluoromethyl-phenyl | ethyl(S) | 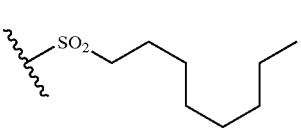 | — |
| (I-2a-200) | 2-methoxy-4-trifluoromethyl-phenyl | ethyl(S) | 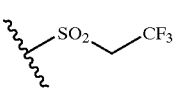 | — |
| (I-2a-201) | 2-methoxy-4-trifluoromethyl-phenyl | ethyl(S) | 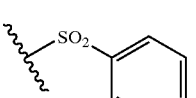 | — |
| (I-2a-202) | 2-methoxy-4-trifluoromethyl-phenyl | ethyl(S) |  | — |

TABLE 4-continued

Analytical Data for Representative Compounds

| Cpd. No. | Ar | R | R₁ | Analytical Data |
|---|---|---|---|---|
| (I-2a-203) | 2-methoxy-4-trifluoromethyl-phenyl | ethyl(S) | -SO₂-CH₂-phenyl | — |
| (I-2a-204) | 2-methoxy-4-trifluoromethyl-phenyl | ethyl(S) | -SO₂-CH=CH-phenyl | — |
| (I-2a-205) | 2-methoxy-4-trifluoromethyl-phenyl | ethyl(S) | -SO₂-(4-methylphenyl) | — |
| (I-2a-206) | 2-methoxy-4-trifluoromethyl-phenyl | ethyl(S) | -SO₂-(4-chlorophenyl) | — |
| (I-2a-207) | 2-methoxy-4-trifluoromethyl-phenyl | ethyl(S) | -SO₂-(4-fluorophenyl) | — |
| (I-2a-208) | 2-methoxy-4-trifluoromethyl-phenyl | ethyl(S) | -SO₂-(4-methoxyphenyl) | — |
| (I-2a-209) | 2-methoxy-4-trifluoromethyl-phenyl | ethyl(S) | -SO₂-(4-bromophenyl) | — |
| (I-2a-210) | 2-methoxy-4-trifluoromethyl-phenyl | ethyl(S) | -SO₂-(4-propylphenyl) | — |
| (I-2a-211) | 2-methoxy-4-trifluoromethyl-phenyl | ethyl(S) | -SO₂-(4-ethylphenyl) | — |
| (I-2a-212) | 2-methoxy-4-trifluoromethyl-phenyl | ethyl(S) | -SO₂-(4-trifluoromethylphenyl) | — |

TABLE 4-continued

Analytical Data for Representative Compounds

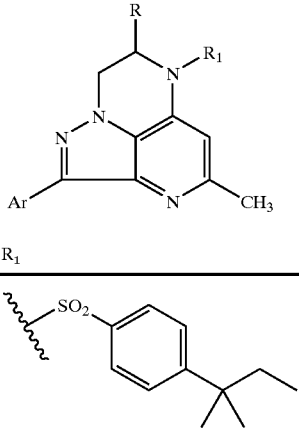

| Cpd. No. | Ar | R | R₁ | Analytical Data |
|---|---|---|---|---|
| (I-2a-213) | 2-methoxy-4-trifluoromethyl-phenyl | ethyl(S) | 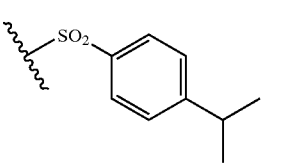 | — |
| (I-2a-214) | 2-methoxy-4-trifluoromethyl-phenyl | ethyl(S) | 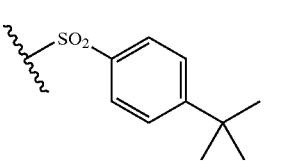 | — |
| (I-2a-215) | 2-methoxy-4-trifluoromethyl-phenyl | ethyl(S) | 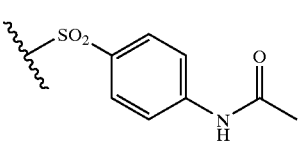 | — |
| (I-2a-216) | 2-methoxy-4-trifluoromethyl-phenyl | ethyl(S) | 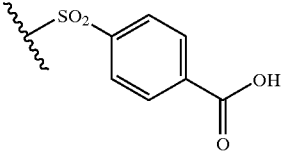 | — |
| (I-2a-217) | 2-methoxy-4-trifluoromethyl-phenyl | ethyl(S) | 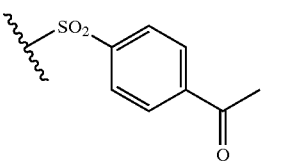 | — |
| (I-2a-218) | 2-methoxy-4-trifluoromethyl-phenyl | ethyl(S) | 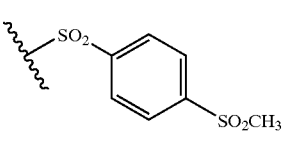 | — |
| (I-2a-219) | 2-methoxy-4-trifluoromethyl-phenyl | ethyl(S) | 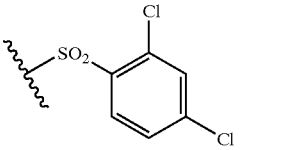 | — |
| (I-2a-220) | 2-methoxy-4-trifluoromethyl-phenyl | ethyl(S) |  | — |

TABLE 4-continued

Analytical Data for Representative Compounds

| Cpd. No. | Ar | R | R₁ | Analytical Data |
|---|---|---|---|---|
| (I-2a-221) | 2-methoxy-4-trifluoromethyl-phenyl | ethyl(S) | -SO₂-(2,4-difluorophenyl) | — |
| (I-2a-222) | 2-methoxy-4-trifluoromethyl-phenyl | ethyl(S) | -SO₂-(2,3,4,5-tetramethylphenyl) | — |
| (I-2a-223) | 2-methoxy-4-trifluoromethyl-phenyl | ethyl(S) | -SO₂-(1-naphthyl) | — |
| (I-2a-224) | 2-methoxy-4-trifluoromethyl-phenyl | ethyl(S) | -SO₂-(quinolin-8-yl) | — |
| (I-2a-225) | 2-methoxy-4-trifluoromethyl-phenyl | ethyl(S) | -SO₂-(isoquinolin-7-yl) | — |
| (I-2a-226) | 2-methoxy-4-trifluoromethyl-phenyl | ethyl(S) | -SO₂-(4,5-dichlorothien-2-yl) | — |
| (I-2a-227) | 2-methoxy-4-trifluoromethyl-phenyl | ethyl(S) | -SO₂-(2,5-dichlorothien-3-yl) | — |

TABLE 4-continued

Analytical Data for Representative Compounds

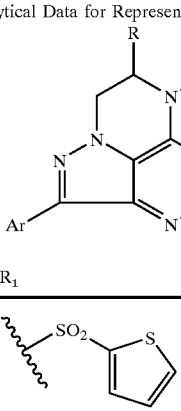

| Cpd. No. | Ar | R | R₁ | Analytical Data |
|---|---|---|---|---|
| (I-2a-228) | 2-methoxy-4-trifluoromethyl-phenyl | ethyl(S) | 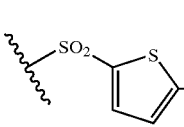 | — |
| (I-2a-229) | 2-methoxy-4-trifluoromethyl-phenyl | ethyl(S) | 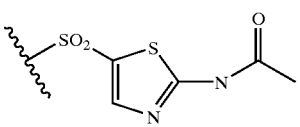 | — |
| (I-2a-230) | 2-methoxy-4-trifluoromethyl-phenyl | ethyl(S) | 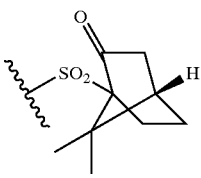 | — |
| (I-2a-231) | 2-methoxy-4-trifluoromethyl-phenyl | ethyl(S) | 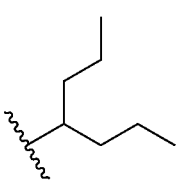 | — |
| (I-2a-232) | 2-trifluoromethyl-4-isopropylphenyl | ethyl(S) | 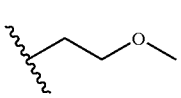 | — |
| (I-2a-233) | 2-trifluoromethyl-4-isopropylphenyl | ethyl(S) | 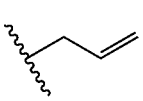 | — |
| (I-2a-234) | 2-trifluoromethyl-4-isopropylphenyl | ethyl(S) | 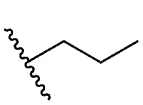 | — |
| (I-2a-235) | 2-trifluoromethyl-4-isopropylphenyl | ethyl(S) | 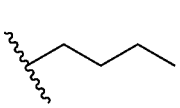 | — |
| (I-2a-236) | 2-trifluoromethyl-4-isopropylphenyl | ethyl(S) | 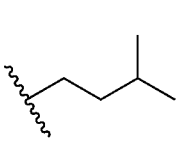 | — |
| (I-2a-237) | 2-trifluoromethyl-4-isopropylphenyl | ethyl(S) |  | — |

TABLE 4-continued

Analytical Data for Representative Compounds

| Cpd. No. | Ar | R | R₁ | Analytical Data |
|---|---|---|---|---|
| (I-2a-238) | 2-trifluoromethyl-4-isopropylphenyl | ethyl(S) | (hexyl chain) | — |

Example 8

Synthesis of Further Representative Compounds of Structure (I-2A)

The representative compounds of Table 5 were made by the following procedure:

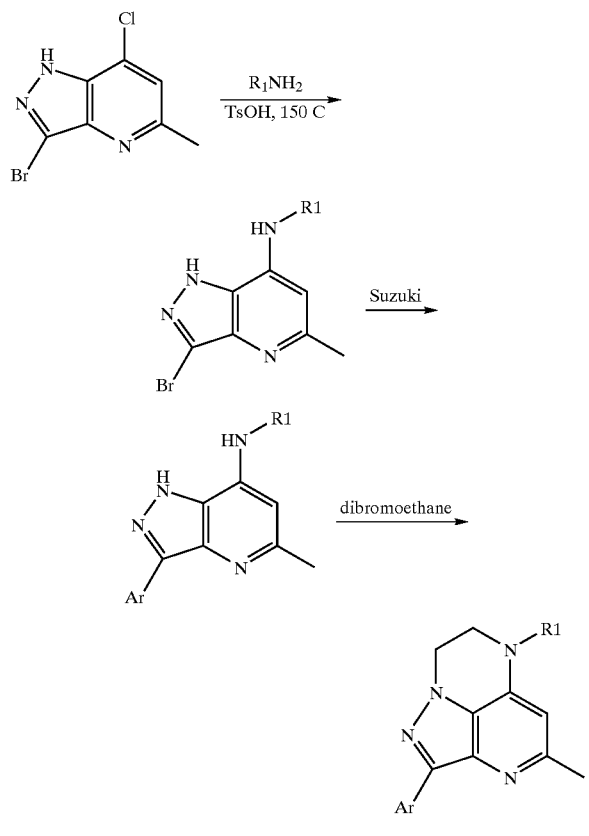

TABLE 5

Analytical Data for Representative Compounds

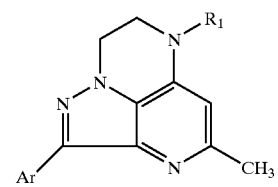

| Cpd. No. | Ar | R₁ | Analytical Data |
|---|---|---|---|
| (I-2a-239) | 2-methyl-4-methoxyphenyl | (branched alkyl) | LC/MS 421 (MH+) |
| (I-2a-240) | 2-methyl-4-methoxyphenyl | (branched alkyl) | LC/MS 365 (MH+) |
| (I-2a-241) | 2-methyl-4-methoxyphenyl | (branched alkyl) | LC/MS 393 (MH+) |
| (I-2a-242) | 2,4-dimethoxyphenyl | (branched alkyl) | LC/MS 409 (MH+) |

TABLE 5-continued
Analytical Data for Representative Compounds
| Cpd. No. | Ar | R$_1$ | Analytical Data |
|---|---|---|---|
| (I-2a-243) | 2-methyl-4-methoxyphenyl | | LC/MS 393 (MH+) |
Example 9
Synthesis of Further Representative Compounds of Structure (I-2A)
The representative compounds of Table 6 were made by the following procedure:
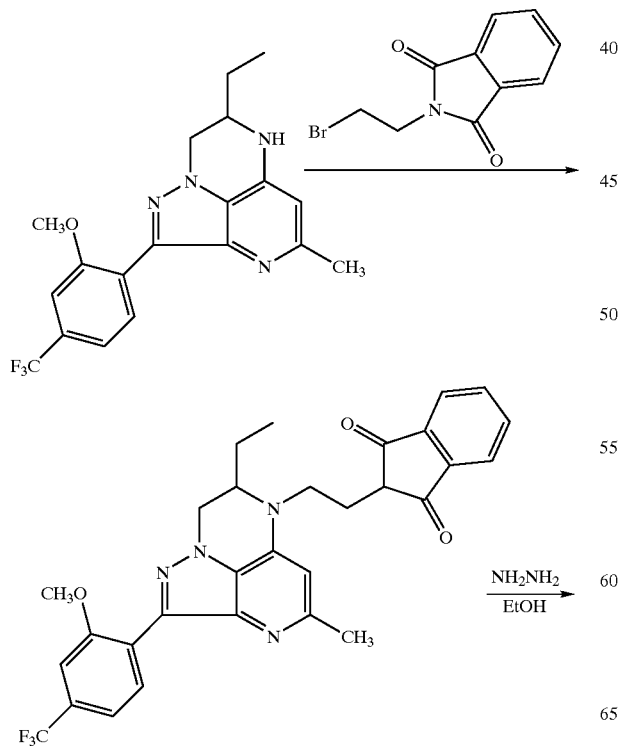
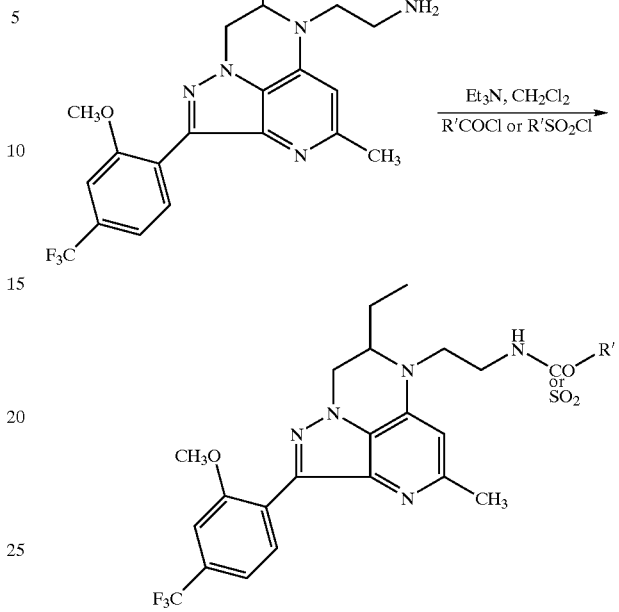
TABLE 6
Analytical Data for Representative Compounds
| Cpd. No. | COR'/SO$_2$R' |
|---|---|
| (I-2a-244) | |
| (I-2a-245) | |
| (I-2a-246) | |

TABLE 6-continued
Analytical Data for Representative Compounds
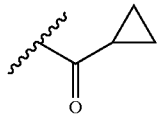
| Cpd. No. | COR'/SO₂R' |
|---|---|
| (I-2a-247) | 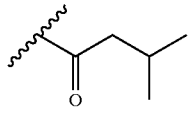 |
| (I-2a-248) | 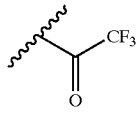 |
| (I-2a-249) | 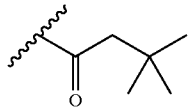 |
| (I-2a-250) | 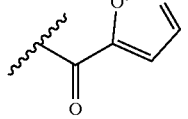 |
| (I-2a-251) | 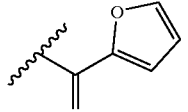 |
| (I-2a-252) | 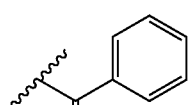 |
| (I-2a-253) | 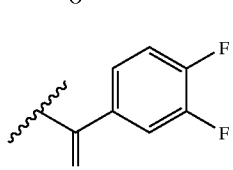 |
| (I-2a-254) | 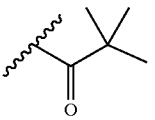 |
TABLE 6-continued
Analytical Data for Representative Compounds
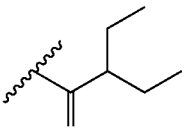
| Cpd. No. | COR'/SO₂R' |
|---|---|
| (I-2a-255) | 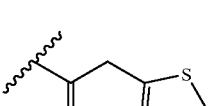 |
| (I-2a-256) | 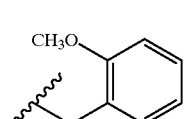 |
| (I-2a-257) | 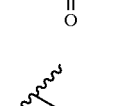 |
| (I-2a-258) | 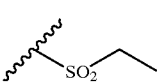 |
| (I-2a-259) |  |
| (I-2a-260) | 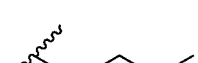 |
| (I-2a-261) | |
| (I-2a-262) | |
| (I-2a-263) | 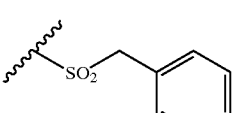 |

TABLE 6-continued

Analytical Data for Representative Compounds

| Cpd. No. | COR'/SO₂R' |
|---|---|
| (I-2a-264) | -SO₂-C₆H₄-CH₃ (para) |
| (I-2a-265) | -SO₂-C₆H₄-OCH₃ (para) |
| (I-2a-266) | -SO₂-C₆H₄-CF₃ (para) |
| (I-2a-267) | -SO₂-C₆H₄-iPr (para) |
| (I-2a-268) | -SO₂-C₆H₄-NHC(O)CH₃ (para) |
| (I-2a-269) | -SO₂-(thiazol-5-yl)-2-NHC(O)CH₃ |

Example 10

Synthesis of Further Representative Compounds of Structure (I-2A)

The representative compounds of Table 7 were made by the following procedure:

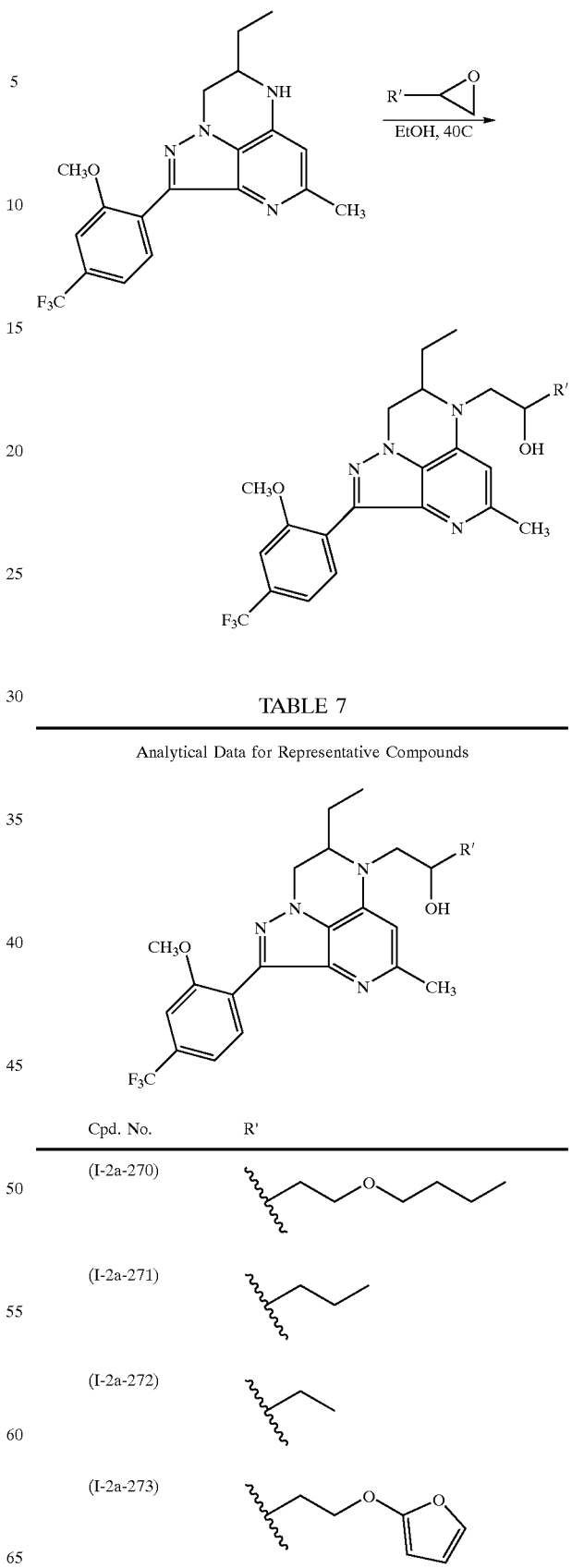

TABLE 7

Analytical Data for Representative Compounds

| Cpd. No. | R' |
|---|---|
| (I-2a-270) | -CH₂CH₂-O-CH₂CH₂CH₂CH₃ |
| (I-2a-271) | -CH₂CH₂CH₃ |
| (I-2a-272) | -CH(CH₃)₂ |
| (I-2a-273) | -CH₂CH₂-O-(furan-2-yl) |

TABLE 7-continued
Analytical Data for Representative Compounds
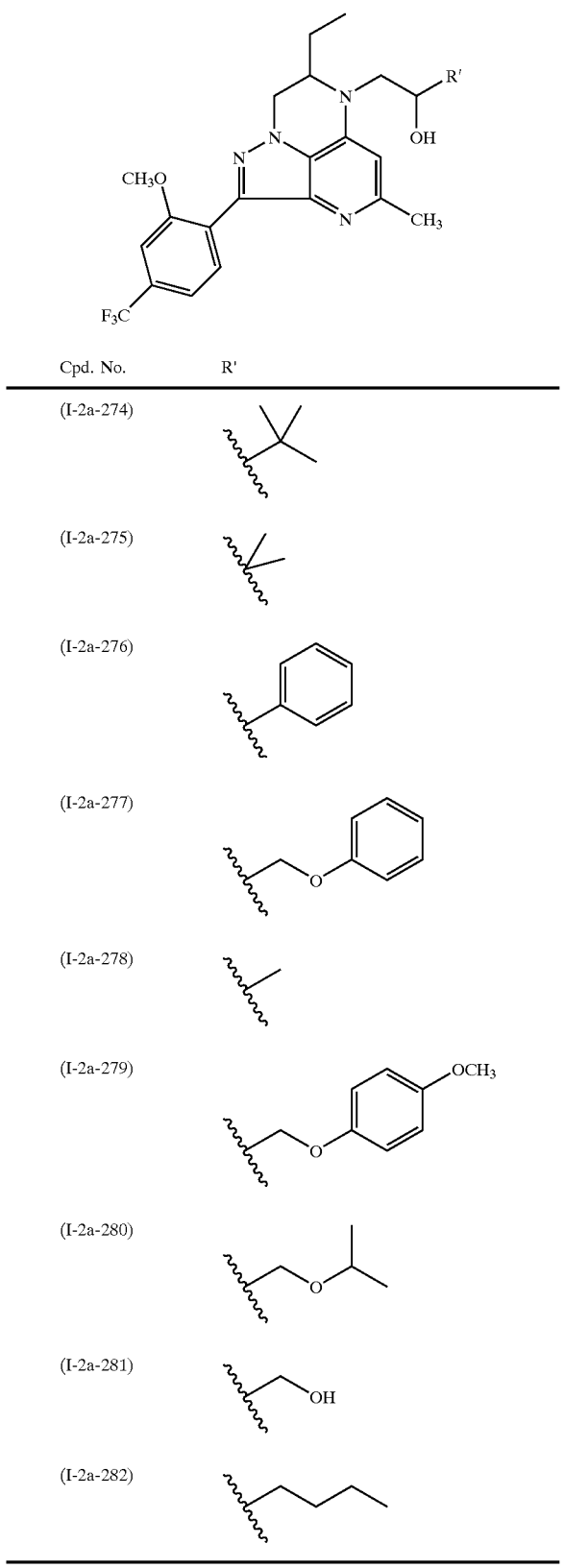
| Cpd. No. | R' |
|---|---|
| (I-2a-274) | *tert*-butyl-CH2- |
| (I-2a-275) | *tert*-butyl |
| (I-2a-276) | phenyl |
| (I-2a-277) | -CH2-O-phenyl |
| (I-2a-278) | isopropyl |
| (I-2a-279) | -CH2-O-C6H4-OCH3 |
| (I-2a-280) | -CH2-O-isopropyl |
| (I-2a-281) | -CH2-OH |
| (I-2a-282) | n-butyl |
Example 11
Synthesis of Further Representative Compounds of Structure (I-2A)
The representative compounds of Table 8 were made by the following procedure:
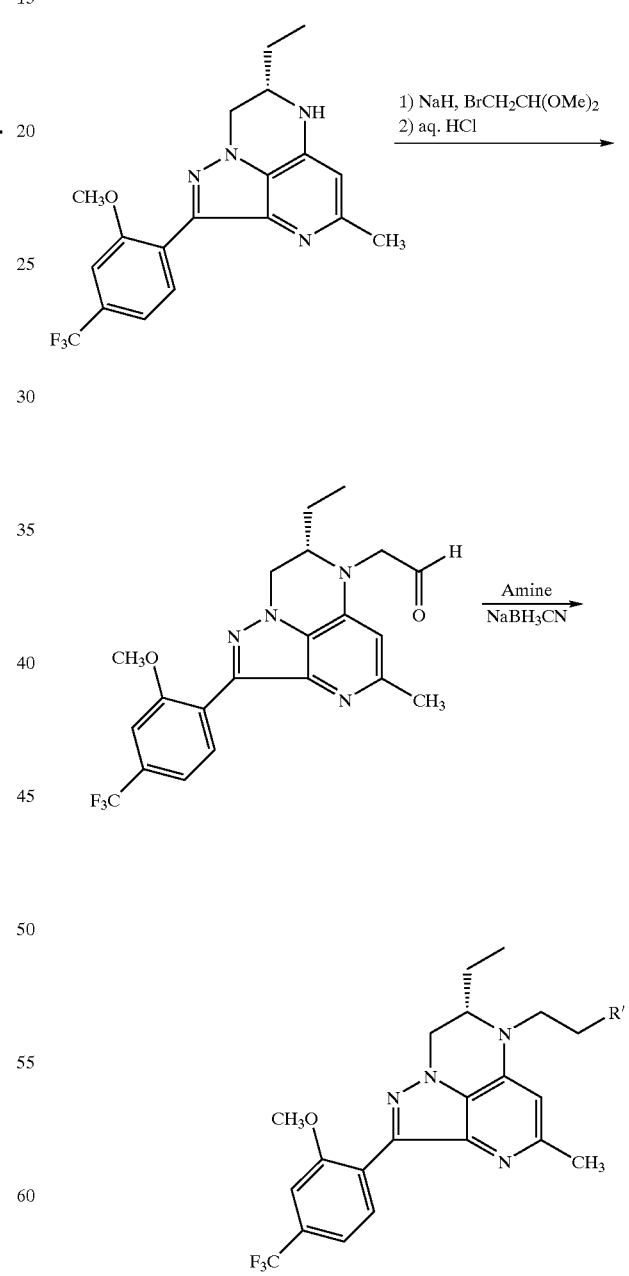

TABLE 8

Analytical Data for Representative Compounds

| Cpd. No. | R' |
|---|---|
| (I-2a-283) | N-propyl-CH2-cyclopropyl |
| (I-2a-284) | N(CH3)-CH2CH2-CN |
| (I-2a-285) | N(CH2Ph)-CH2CH2-CN |
| (I-2a-286) | N(CH2Ph)-CH2CH2-OH |
| (I-2a-287) | N(CH2CH2OH)2 |
| (I-2a-288) | N(propyl)-CH2CH2-OH |
| (I-2a-289) | N(cyclohexyl)-ethyl |
| (I-2a-290) | N(CH3)-CH2-COOH |
| (I-2a-291) | N(CH3)-CH2-CH(OH)-Ph |
| (I-2a-292) | N(CH2Ph)2 |
| (I-2a-293) | tetrahydro-β-carboline-like (indeno-pyridine) |
| (I-2a-294) | 2-methylaziridinyl |
| (I-2a-295) | thiazolidine-4-carboxylic acid |

TABLE 8-continued

Analytical Data for Representative Compounds

| Cpd. No. | R' |
|---|---|
| (I-2a-296) | 2,5-dihydro-1H-pyrrol-1-yl |
| (I-2a-297) | pyrrolidin-1-yl |
| (I-2a-298) | 2-carboxypyrrolidin-1-yl |
| (I-2a-299) | 2-(hydroxymethyl)pyrrolidin-1-yl |
| (I-2a-300) | 3-hydroxypyrrolidin-1-yl |
| (I-2a-301) | 3,6-dihydro-2H-pyridin-1-yl |
| (I-2a-302) | 4-phenylpiperazin-1-yl |
| (I-2a-303) | 4-(4-fluorophenyl)piperazin-1-yl |
| (I-2a-304) | 4-formylpiperazin-1-yl |
| (I-2a-305) | 4-methylpiperazin-1-yl |
| (I-2a-306) | 4-benzylpiperazin-1-yl |
| (I-2a-307) | 4-(2-hydroxyethyl)piperazin-1-yl |
| (I-2a-308) | morpholin-4-yl |
| (I-2a-309) | 2,6-dimethylmorpholin-4-yl |

TABLE 8-continued
Analytical Data for Representative Compounds
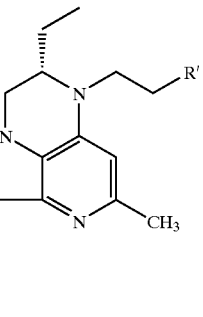
| Cpd. No. | R' |
|---|---|
| (I-2a-310) | 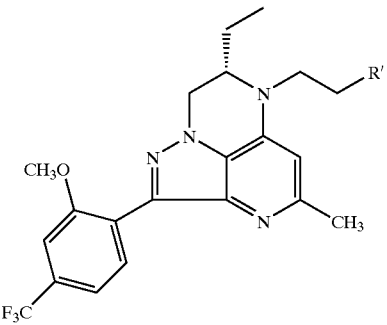 |
| (I-2a-311) | 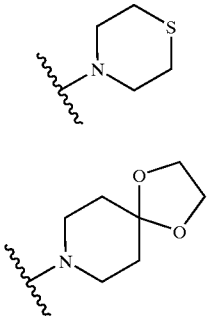 |
| (I-2a-312) | 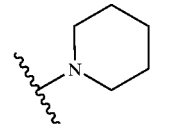 |
| (I-2a-313) | 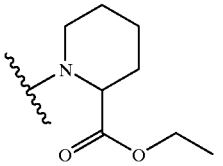 |
| (I-2a-314) | 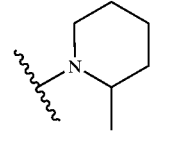 |
| (I-2a-315) | 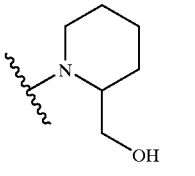 |
| (I-2a-316) | 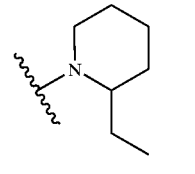 |
TABLE 8-continued
Analytical Data for Representative Compounds
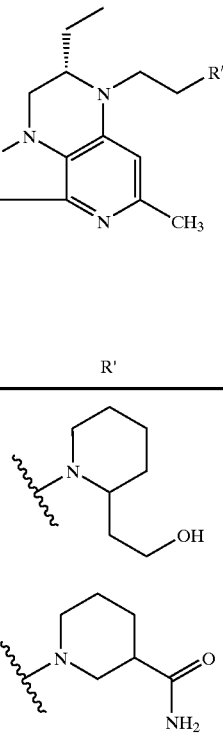
| Cpd. No. | R' |
|---|---|
| (I-2a-317) | 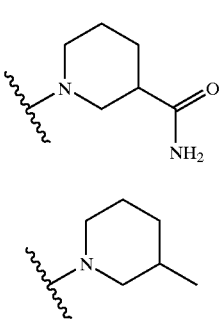 |
| (I-2a-318) | 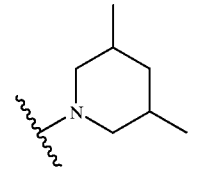 |
| (I-2a-319) | 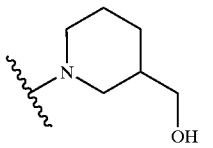 |
| (I-2a-320) | 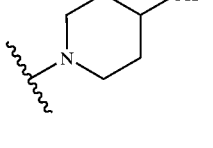 |
| (I-2a-321) | 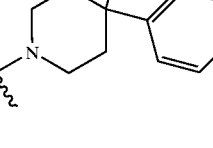 |
| (I-2a-322) | 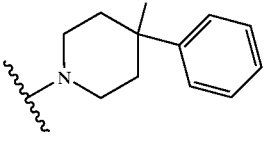 |
| (I-2a-323) | |

TABLE 8-continued
Analytical Data for Representative Compounds
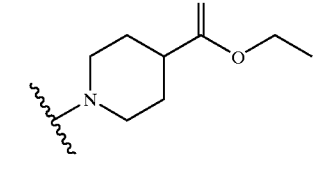
| Cpd. No. | R' |
|---|---|
| (I-2a-324) | 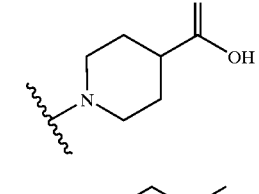 |
| (I-2a-325) | 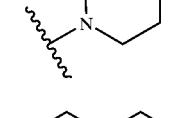 |
| (I-2a-326) | 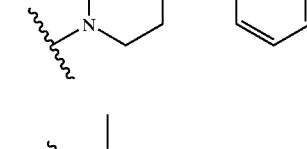 |
| (I-2a-327) | 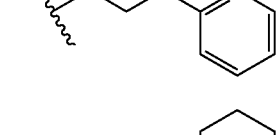 |
| (I-2a-328) | 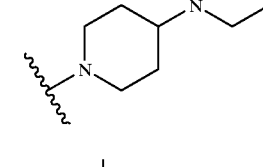 |
| (I-2a-329) | 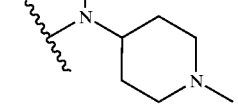 |
| (I-2a-330) | |
TABLE 8-continued
Analytical Data for Representative Compounds
| Cpd. No. | R' |
|---|---|
| (I-2a-331) | |
| (I-2a-332) | |
| (I-2a-333) | |
| (I-2a-334) | |
| (I-2a-335) | |
| (I-2a-336) | |
| (I-2a-337) | |

TABLE 8-continued

Analytical Data for Representative Compounds

| Cpd. No. | R' |
|---|---|
| (I-2a-338) | N(CH₃)CH₂CH(OCH₃)₂ |
| (I-2a-339) | N(CH₃)CH₂CH=CH₂ |
| (I-2a-340) | N(iPr)₂ |
| (I-2a-341) | N(iPr)(CH₂Ph) |
| (I-2a-342) | N(iBu)₂ |
| (I-2a-343) | N(CH₃)(Et) |
| (I-2a-344) | N(Et)(CH₂Ph) |
| (I-2a-345) | N(Et)₂ |
| (I-2a-346) | N(Et)CH₂CH₂N(CH₃)₂ |
| (I-2a-347) | N(CH₃)CH₂CH₂N(Et)₂ |
| (I-2a-348) | N(CH₂Ph)C(O)OEt |
| (I-2a-349) | N(CH₃)(nPr) |
| (I-2a-350) | N(nPr)₂ |
| (I-2a-351) | N(Et)(nBu) |
| (I-2a-352) | N(nBu)₂ |

TABLE 8-continued

Analytical Data for Representative Compounds

| Cpd. No. | R' |
|---|---|
| (I-2a-353) | N,N-dipentyl |
| (I-2a-354) | N,N-dihexyl |
| (I-2a-355) | N-methyl-N-(1,3-dioxolan-2-ylmethyl) |
| (I-2a-356) | N-ethyl-N-(2-methylallyl) |
| (I-2a-357) | N-methyl-N-(2-chlorobenzyl) |
| (I-2a-358) | 2-methylpyrrolidin-1-yl |
| (I-2a-359) | N-methyl-N-(2-(dimethylamino)ethyl) |
| (I-2a-360) | N-propyl-N-(2,5-cyclohexadien-1-ylmethyl) |
| (I-2a-361) | N-ethyl-N-propyl |
| (I-2a-362) | N-methyl-N-[1-(4-chlorophenoxy)ethyl] |
| (I-2a-363) | N-cyclohexyl-N-(2-hydroxyethyl) |
| (I-2a-364) | 4-(3,4-dimethylphenyl)piperazin-1-yl |

TABLE 8-continued

Analytical Data for Representative Compounds

| Cpd. No. | R' |
|---|---|
| (I-2a-365) | 2-methyl-5-ethyl-piperidin-1-yl |
| (I-2a-366) | 4-(4-fluorophenyl)-4-hydroxy-piperidin-1-yl |
| (I-2a-367) | 4-benzyl-4-hydroxy-piperidin-1-yl |
| (I-2a-368) | N-ethyl-N-(2-(pyridin-2-yl)ethyl)amino |
| (I-2a-369) | N-propyl-N-(2-(pyridin-2-yl)ethyl)amino |
| (I-2a-370) | N-ethyl-N-(pyridin-4-ylmethyl)amino |
| (I-2a-371) | N,N-bis(2-methoxyethyl)amino |
| (I-2a-372) | 2-(tert-butoxycarbonyl)pyrrolidin-1-yl |
| (I-2a-373) | 4-(pyrrolidin-1-yl)piperidin-1-yl |
| (I-2a-374) | 4-(2,5-dimethylphenyl)piperazin-1-yl |
| (I-2a-375) | 4-(2-fluorophenyl)piperidin-1-yl |
| (I-2a-376) | 4-(2,3-dimethylphenyl)piperazin-1-yl |

141
TABLE 8-continued
Analytical Data for Representative Compounds
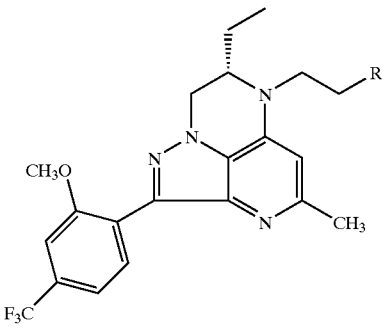
| Cpd. No. | R' |
|---|---|
| (I-2a-377) | 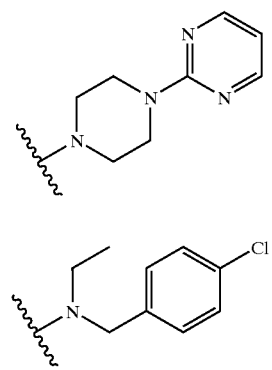 |
| (I-2a-378) | 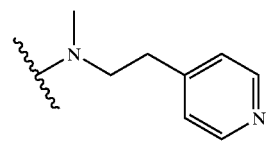 |
| (I-2a-379) | 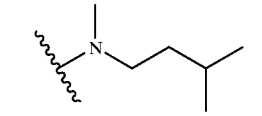 |
| (I-2a-380) | 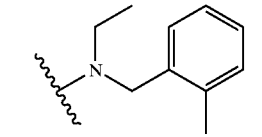 |
| (I-2a-381) | 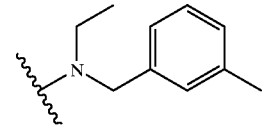 |
| (I-2a-382) | 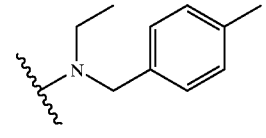 |
| (I-2a-383) | 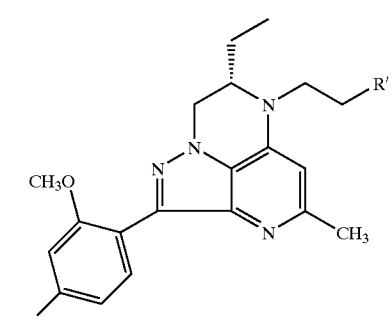 |
142
TABLE 8-continued
Analytical Data for Representative Compounds
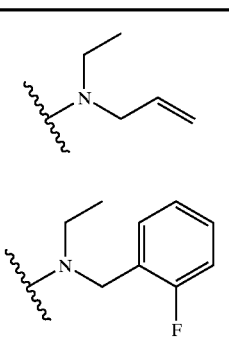
| Cpd. No. | R' |
|---|---|
| (I-2a-384) | 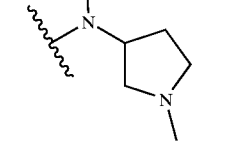 |
| (I-2a-385) | 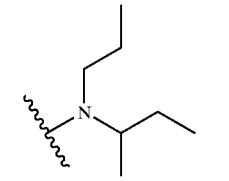 |
| (I-2a-386) | 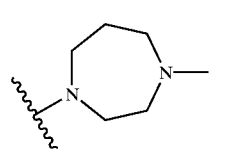 |
| (I-2a-387) | 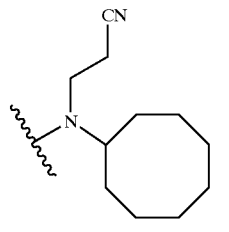 |
| (I-2a-388) | |
| (I-2a-389) | |

TABLE 8-continued

Analytical Data for Representative Compounds

| Cpd. No. | R' |
|---|---|
| (I-2a-390) | pyrrolidine-N-yl with 2-COOH |
| (I-2a-391) | pyrrolidine-N-yl with 2-CH₂OH |
| (I-2a-392) | piperidine-N-yl with 2-COOH |
| (I-2a-393) | 4-(4-hydroxyphenyl)piperazin-1-yl |
| (I-2a-394) | 4-(4-methylphenyl)-2-methylpiperazin-1-yl |
| (I-2a-395) | N-methyl-N-[2-(3,4-dimethoxyphenyl)ethyl]amino |

TABLE 8-continued

Analytical Data for Representative Compounds

| Cpd. No. | R' |
|---|---|
| (I-2a-396) | 2,5-dimethylpiperazin-1-yl |
| (I-2a-397) | 4-(tert-butoxycarbonyl)piperazin-1-yl |
| (I-2a-398) | 2-[(1-methylpyrrolidin-2-yl)methyl]piperidin-1-yl |
| (I-2a-399) | pyrrolidine-N-yl with 4-methyl and 2-COOCH₃ |
| (I-2a-400) | 3-(acetylamino)pyrrolidin-1-yl |

TABLE 8-continued
Analytical Data for Representative Compounds
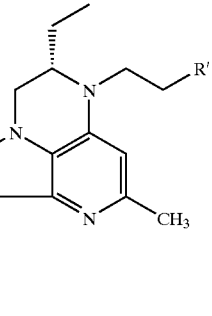
| Cpd. No. | R' |
|---|---|
| (I-2a-401) | 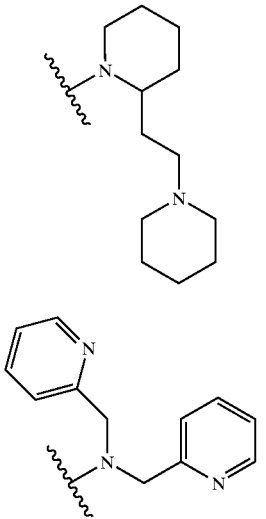 |
| (I-2a-402) | 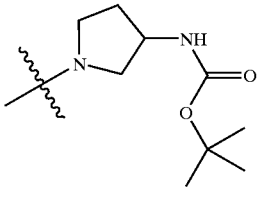 |
| (I-2a-403) | 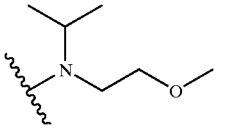 |
| (I-2a-404) | 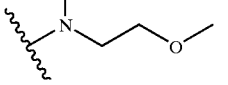 |
| (I-2a-405) | 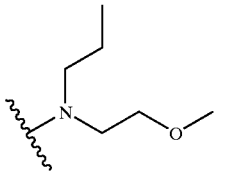 |
| (I-2a-406) | 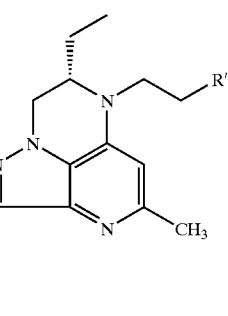 |
TABLE 8-continued
Analytical Data for Representative Compounds
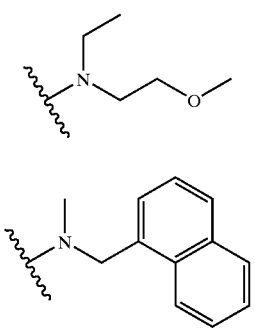
| Cpd. No. | R' |
|---|---|
| (I-2a-407) | 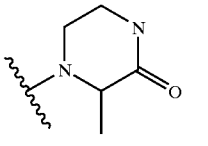 |
| (I-2a-408) | 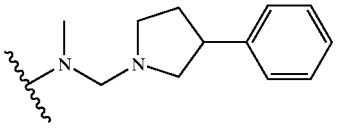 |
| (I-2a-409) | 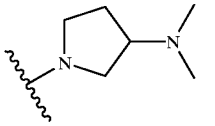 |
| (I-2a-410) | 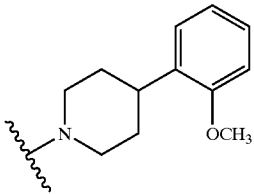 |
| (I-2a-411) | 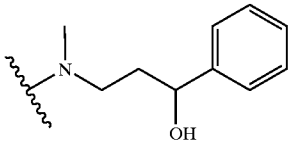 |
| (I-2a-412) | |
| (I-2a-413) | |

Example 12
Synthesis of Further Representative Compounds of Structure (I-2A)
The representative compounds of Table 9 were made by the following procedure:
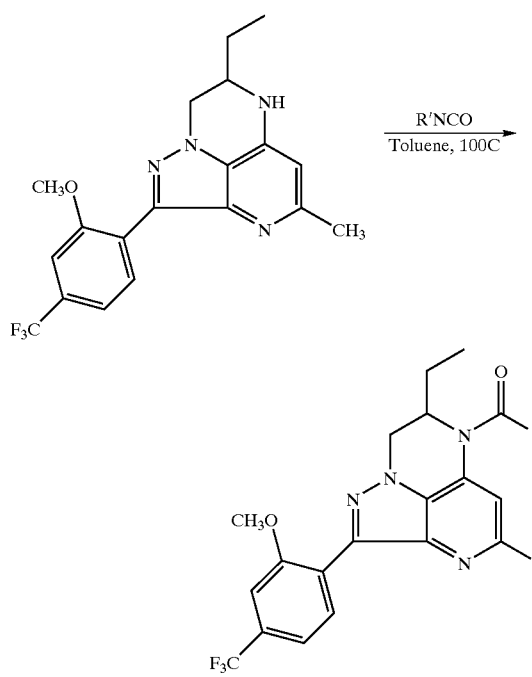
TABLE 9
Analytical Data for Representative Compounds
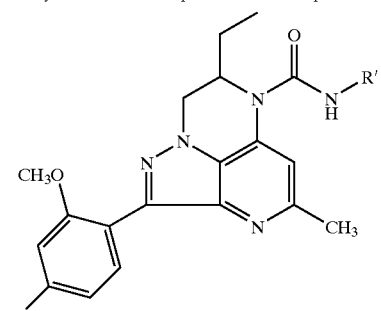
| Cpd. No. | R' |
|---|---|
| (I-2a-414) | 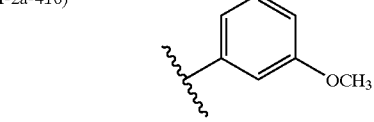 |
| (I-2a-415) | |
TABLE 9-continued
Analytical Data for Representative Compounds
| Cpd. No. | R' |
|---|---|
| (I-2a-416) | 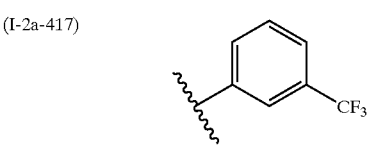 |
| (I-2a-417) | 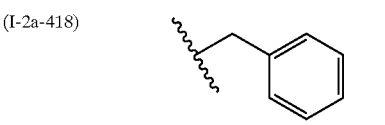 |
| (I-2a-418) | 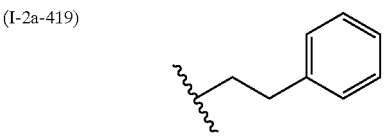 |
| (I-2a-419) | |
| (I-2a-420) | 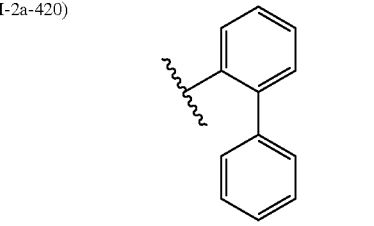 |
| (I-2a-421) |  |
| (I-2a-422) | 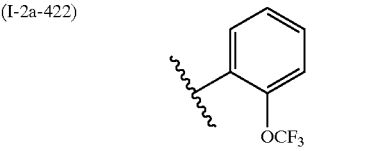 |

TABLE 9-continued

Analytical Data for Representative Compounds

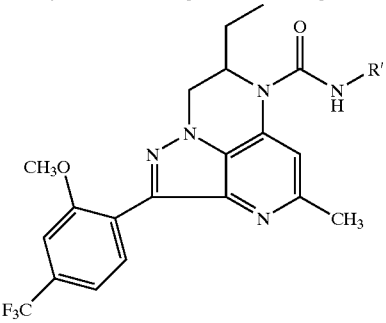

| Cpd. No. | R' |
|---|---|
| (I-2a-423) | 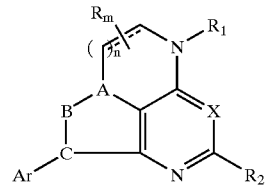 |

Example 13

Representative Compounds Having CRF Receptor Binding Activity

The compounds of this invention may be evaluated for binding activity to the CRF receptor by a standard radioligand binding assay as generally described by DeSouza et al. (*J. Neurosci.* 7:88–100, 1987). By utilizing various radiolabeled CRF ligands, the assay may be used to evaluate the binding activity of the compounds of the present invention with any CRF receptor subtype. Briefly, the binding assay involves the displacement of a radiolabeled CRF ligand from the CRF receptor.

More specifically, the binding assay is performed in 1.5 ml Eppendorf tubes using approximately $1 \times 10^6$ cells per tube stably transfected with human CRF receptors. Each tube receives about 0.1 ml of assay buffer (e.g., Dulbecco's phosphate buffered saline, 10 mM magnesium chloride, 20 $\mu$M bacitracin) with or without unlabeled sauvagine, urotensin I or CRF (final concentration, 1 $\mu$M) to determine nonspecific binding, 0.1 ml of [$^{125}$I] tyrosine-ovine CRF (final concentration ~200 pM or approximately the $K_D$ as determined by Scatchard analysis) and 0.1 ml of a membrane suspension of cells containing the CRF receptor. The mixture is incubated for 2 hours at 22° C. followed by the separation of the bound and free radioligand by centrifugation. Following two washes of the pellets, the tubes are cut just above the pellet and monitored in a gamma counter for radioactivity at approximately 80% efficiency. All radioligand binding data may be analyzed using the non-linear least-square curve-fitting program LIGAND of Munson and Rodbard (*Anal. Biochem.* 107:220, 1990).

Example 14

CRF-stimulated Adenylate Cyclase Activity

The compounds of the present invention may also be evaluated by various functional testing. For example, the compounds of the present invention may be screened for CRF-stimulated adenylate cyclase activity. An assay for the determination of CRF-stimulated adenylate cyclase activity may be performed as generally described by Battaglia et al. (*Synapse* 1:572, 1987), with modifications to adapt the assay to whole cell preparations.

More specifically, the standard assay mixture may contain the following in a final volume of 0.5 ml: 2 mM L-glutamine, 20 mM HEPES, and 1 mM IMBX in DMEM buffer. In stimulation studies, whole cells with the transfected CRF receptors are plated in 24-well plates and incubated for 1 h at 37° C. with various concentrations of CRF-related and unrelated peptides in order to establish the pharmacological rank-order profile of the particular receptor subtype. Following the incubation, the media is aspirated, the wells rinsed once gently with fresh media, and the media aspirated. To determine the amount of intracellular cAMP, 300 $\mu$l of a solution of 95% ethanol and 20 mM aqueous hydrochloric acid is added to each well and the resulting suspensions are incubated at -20° C. for 16 to 18 hours. The solution is removed into 1.5 ml Eppendorf tubes and the wells washed with an additional 200 $\mu$l of ethanol/aqueous hydrochloric acid and pooled with the first fraction. The samples are lyophilized and then resuspended with 500 $\mu$l sodium acetate buffer. The measurement of cAMP in the samples is performed using a single antibody kit from Biomedical Technologies Inc. (Stoughton, Mass.). For the functional assessment of the compounds, a single concentration of CRF or related peptides causing 80% stimulation of cAMP production is incubated along with various concentrations of competing compounds ($10^{-12}$ to $10^{-6}$ M).

It will be appreciated that, although specific embodiments of the invention have been described herein for purposes of illustration, various modifications may be made without departing from the spirit and scope of the invention. Accordingly, the invention is not limited except as by the appended claims.

What is claimed is:
1. A compound having the following structure:

$$\begin{array}{c}
\text{structure with } R_m, R_1, A, B, C, X, R_2, \text{Ar}
\end{array}$$

or a stereoisomer or pharmaceutically acceptable salt thereof, wherein:

n is 1;

A is carbon or CH;

B is nitrogen or $CR_3$;

C is nitrogen, carbon or CH;

with the provisos that at least one of B and C is nitrogen, and either A—B or B—C is a double bond;

X is nitrogen or CH;

Ar is substituted aryl or substituted heteroaryl;

R is an optional substituent which, at each occurrence, is independently alkyl, alkylidenyl, arylalkyl or heteroarylalkyl, wherein m is 0, 1, 2 or 3 and represents the number of R substituents;

$R_1$ is $-C(H)_{0,1}(R_4)(R_5)$ or $-SO_2R_5$;

$R_2$ is hydrogen or alkyl;

$R_3$ is hydrogen, alkyl or haloalkyl;

$R_4$ is hydrogen, keto, alkyl, alkylidenyl, or halo; and $R_5$ is a radical of the formula $-Y-Z-R_6$, wherein Y is an alkanediyl, substituted alkanediyl, or a direct bond, Z is NH, —N(R$_7$), O, S, SO$_2$, C(=O), C(=O)O, OC(=O), NHC(=O), C(=O)NH, NH(SO$_2$), (SO$_2$)NH, NR$_8$C(=O)O, or a direct bond;

R$_6$ is hydrogen, alkyl, substituted alkyl, aryl, substituted aryl, arylalkyl, substituted arylalkyl, heterocycle, substituted heterocycle, heterocyclealkyl, or substituted heterocyclealkyl;

R$_7$ and R$_8$ are the same or different and independently alkyl, substituted alkyl, aryl, substituted aryl, arylalkyl, substituted arylalkyl, heterocycle, substituted heterocycle, heterocyclealkyl, or substituted heterocyclealkyl; or R$_6$ and R$_7$ taken together with the nitrogen atom to which they are attached form a heterocycle ring or substituted heterocycle ring;

or R$_4$ and R$_5$ taken together form cycloalkyl, substituted cycloalkyl, cycloalkylcycloalkyl, substituted cycloalkylcycloalkyl, cycloalkylaryl, substituted cycloalkylaryl, cycloalkylheterocycle, or substituted cycloalkylheterocycle; and wherein:

heterocycle is, at each occurrence, independently heteroaryl, morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydrothienyl, tetrahydropyrimidinyl or tetrahydrothiopyranyl; and heteroaryl is, at each occurrence, independently furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl or quinazolinyl.

2. The compound of claim 1 having one of the following structures:

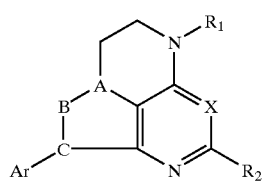
(Ia)

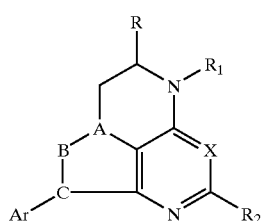
(Ib)

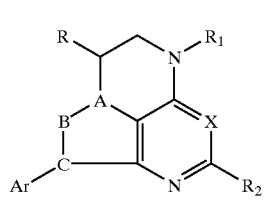
(Ic)

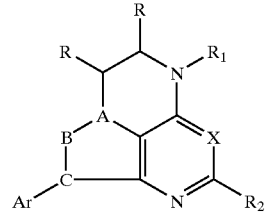
(Id)

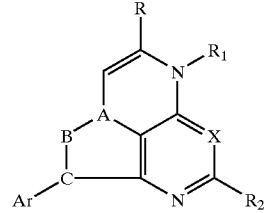
(Ie)

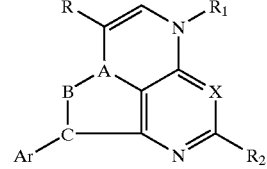
(If)

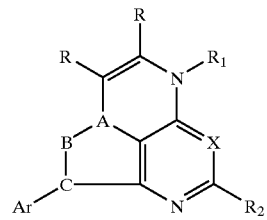
(Ig)

3. The compound of claim 1 having one of the following structures:

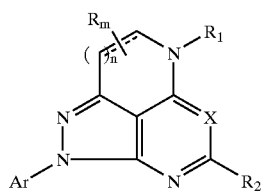
(I-1)

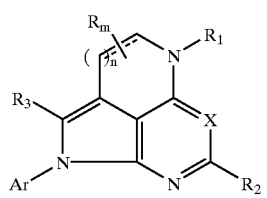
(I-4)

4. The compound of claim 3 wherein X is CH and having one of the following structures:

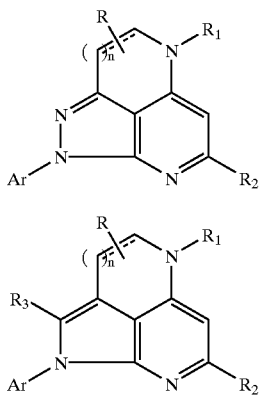

(I-1a)

(I-4a)

5. The compound of claim 3 wherein X is nitrogen and having one of the following structures:

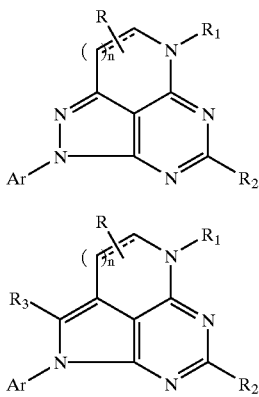

(I-1b)

(I-4b)

6. The compound of claim 1 wherein Ar is substituted phenyl.

7. The compound of claim 6 wherein substituted phenyl is 2,4-dichlorophenyl, 2-chloro-4-methyl-phenyl, 2-methyl-4-chloro-phenyl, 2,4,6-trimethyl-phenyl, 2-chloro-4-methoxy-phenyl, 2-methyl-4-methoxy-phenyl, or 2,4-dimethoxy-phenyl.

8. The compound of claim 1 wherein Ar is substituted heteroaryl.

9. The compound of claim 8 wherein substituted heteroaryl is substituted pyridinyl.

10. The compound of claim 8 wherein substituted heteroaryl is 4-methyl-6-dimethylamino-pyridin-3-yl, 4-dimethylamino-6-methyl-pyridin-3-yl or 6-dimethylamino-pyridin-3-yl.

11. The compound of claim 1 wherein R is hydrogen.

12. The compound of claim 1 wherein R is alkyl.

13. The compound of claim 1 wherein R is arylalkyl.

14. The compound of claim 1 wherein $R_1$ is —CH(n-propyl)$_2$, —CH(n-propyl)(CH$_2$OCH$_3$), —CH(phenyl)(CH$_2$OCH$_3$), —CH(CH$_2$OR')$_2$, —CH(CH$_2$OR')(ethyl), —CH(CH$_2$OR')(n-butyl), —CH(CH$_2$OR')(tert-butyl), —CH(CH$_2$OR')(4-chloro-phenyl), —CH(CH$_2$OR)(CH$_2$CH$_2$SCH$_3$), —CH(CH$_2$CH$_3$)(CH$_2$Ophenyl), where each occurrence of R' is independently selected from $C_{1-6}$alkyl.

15. The compound of claim 1 wherein $R_1$ is —SO$_2$R$_5$.

16. The compound of claim 1 wherein $R_1$ is —C(H)$_{0,1}$(R$_4$)(R$_5$).

17. The compound of claim 16 wherein $R_1$ is —CH$_2$R$_5$.

18. The compound of claim 16 wherein $R_1$ is —C(=O)R$_5$.

19. The compound of claim 16 wherein $R_1$ is —CH(R$_4$)(R$_5$).

20. The compound of claim 1 wherein $R_4$ is hydrogen.

21. The compound of claim 1 wherein $R_4$ is alkyl.

22. The compound of claim 1 wherein $R_4$ is keto.

23. The compound of claim 1 wherein Y is alkanediyl or substituted alkanediyl.

24. The compound of claim 1 wherein Y is a direct bond.

25. The compound of claim 1 wherein Z is NH, —N(R$_7$), O, S, SO$_2$, C(=O), C(=O)O, OC(=O), NHC(=O), C(=O)NH, NH(SO$_2$), (SO$_2$)NH or NR$_8$C(=O)O.

26. The compound of claim 1 wherein Z is a direct bond.

27. The compound of claim 1 wherein $R_6$ is hydrogen, alkyl or substituted alkyl.

28. The compound of claim 1 wherein $R_6$ is aryl, substituted aryl, arylalkyl or substituted arylalkyl.

29. The compound of claim 1 wherein $R_6$ is heterocyle, substituted heterocycle, heterocyclealkyl or substituted heterocylcealkyl.

30. The compound of claim 1 wherein $R_2$ is methyl.

31. The compound of claim 1 wherein $R_2$ is ethyl.

32. A pharmaceutical composition comprising a compound of claim 1 in combination with a pharmaceutically acceptable carrier or diluent.

* * * * *